(12) United States Patent  
Rousso et al.

(10) Patent No.: US 8,894,974 B2  
(45) Date of Patent: Nov. 25, 2014

(54) RADIOPHARMACEUTICALS FOR DIAGNOSIS AND THERAPY

(75) Inventors: Benny Rousso, Rishon-LeZion (IL); Chalom Bruno Sayada, Luxembourg ville (LU)

(73) Assignee: Spectrum Dynamics LLC, Orangeburg, NY (US)

( * ) Notice: Subject to any disclaimer, the term of this patent is extended or adjusted under 35 U.S.C. 154(b) by 1296 days.

(21) Appl. No.: 11/747,378

(22) Filed: May 11, 2007

(65) Prior Publication Data

US 2007/0265230 A1    Nov. 15, 2007

Related U.S. Application Data

(60) Provisional application No. 60/799,688, filed on May 11, 2006.

(51) Int. Cl.
*A61K 51/00* (2006.01)
*A61K 49/00* (2006.01)
*A61K 31/66* (2006.01)

(52) U.S. Cl.
CPC ............ *A61K 31/66* (2013.01); *A61K 49/0004* (2013.01); *A61K 51/00* (2013.01)
USPC ........................................ 424/9.2

(58) Field of Classification Search
None
See application file for complete search history.

(56) References Cited

U.S. PATENT DOCUMENTS

| | | | |
|---|---|---|---|
| 630,611 A | 8/1899 | Knapp et al. |
| 2,776,377 A | 1/1957 | Anger |
| 3,340,866 A | 9/1967 | Noeller |
| 3,446,965 A | 5/1969 | Ogier et al. |
| 3,535,085 A | 10/1970 | Shumate et al. |
| 3,684,887 A | 8/1972 | Hugonin |
| 3,690,309 A | 9/1972 | Pluzhnikov et al. |
| 3,719,183 A | 3/1973 | Schwartz |
| 3,739,279 A | 6/1973 | Hollis |
| 3,971,362 A | 7/1976 | Pope et al. |
| 3,978,337 A | 8/1976 | Nickles et al. |
| 3,988,585 A | 10/1976 | O'Neill et al. |
| 4,000,502 A | 12/1976 | Butler et al. |
| 4,015,592 A | 4/1977 | Bradley-Moore |
| 4,055,765 A | 10/1977 | Gerber et al. |
| 4,061,919 A | 12/1977 | Miller et al. |
| 4,095,107 A | 6/1978 | Genna et al. |
| 4,165,462 A | 8/1979 | Macovski et al. |
| 4,181,856 A | 1/1980 | Bone |
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |
| 4,364,377 A | 12/1982 | Smith |
| 4,383,327 A | 5/1983 | Kruger |
| 4,476,381 A | 10/1984 | Rubin |
| 4,503,331 A | 3/1985 | Kovacs, Jr. et al. |
| 4,521,688 A | 6/1985 | Yin |
| H12 H | 1/1986 | Bennett et al. |
| 4,580,054 A | 4/1986 | Shimoni |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A | 12/1988 | Brunnett |
| 4,801,803 A | 1/1989 | Denen et al. |
| 4,828,841 A | 5/1989 | Porter et al. |
| 4,834,112 A | 5/1989 | Machek et al. |

(Continued)

FOREIGN PATENT DOCUMENTS

| | | |
|---|---|---|
| EP | 0273257 | 7/1988 |
| EP | 0525954 | 2/1993 |

(Continued)

OTHER PUBLICATIONS

Dillman RO. Radiolabeled anti-CD20 monoclonal antibodies for the treatment of B-cell lymphoma. 2002 J. Clin. Oncol. 20: 3545-3557.*

Tedder TF, Klejman G, Schlossman SF, Saito H. Structure of the gene encoding the human B lymphocyte differentiation antigen CD20 (B1). 1989 J. Immunol. 142: 2560-2568.*

Sands H, Jones PL. Methods for the study of the metabolism of radiolabeled monoclonal antibodies by liver and tumor. 1987 J. Nucl. Med. 28: 390-398.*

(Continued)

*Primary Examiner* — Michael G Hartley
*Assistant Examiner* — Jennifer Lamberski
(74) *Attorney, Agent, or Firm* — William H. Dippert; Eckert Seamans Cherin & Mellott, LLC

(57) ABSTRACT

A method for treating a human patient is provided, including administering a radiolabeled form of a therapeutic agent to the patient at a first substantially non-therapeutically-effective dose, wherein pharmacological activity of the therapeutic agent is not due to radioactivity of the therapeutic agent. The method also includes determining information related to a biodistribution of the radiolabeled form of the therapeutic agent in the patient by performing a radioimaging procedure on the patient. Responsively to the information, a decision is made whether or not to treat the patient by administering the therapeutic agent to the patient. If the decision is made to treat the patient, the patient is treated by administering the therapeutic agent to the patient at a second therapeutically-effective dose. If the decision is made not to treat the patient, treatment of the patient with the therapeutic agent is withheld. Other embodiments are also described.

21 Claims, 2 Drawing Sheets

(56) References Cited

U.S. PATENT DOCUMENTS

| | | |
|---|---|---|
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,867,962 A * | 9/1989 | Abrams ............... 424/1.49 |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledly |
| 4,938,230 A | 7/1990 | Machek et al. |
| 4,951,653 A | 8/1990 | Fry et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,863 A | 8/1991 | Matsuno et al. |
| 5,042,056 A | 8/1991 | Hellmick et al. |
| 5,070,877 A | 12/1991 | Mohiuddin et al. |
| 5,070,878 A | 12/1991 | Denen |
| 5,088,492 A | 2/1992 | Takayama et al. |
| 5,115,137 A | 5/1992 | Andersson-Engels et al. |
| 5,119,818 A | 6/1992 | Carroll et al. |
| 5,132,542 A | 7/1992 | Bassalleck et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,179,983 A | 1/1993 | Cordner, Jr. et al. |
| 5,196,796 A | 3/1993 | Misic et al. |
| 5,207,642 A | 5/1993 | Orkin et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A | 3/1994 | Wessels |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,349,190 A | 9/1994 | Hines et al. |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A | 1/1995 | Drane |
| 5,381,791 A | 1/1995 | Qian |
| 5,383,456 A | 1/1995 | Arnold et al. |
| 5,383,858 A | 1/1995 | Reilly et al. |
| 5,386,446 A | 1/1995 | Fujimoto et al. |
| 5,387,409 A | 2/1995 | Nunn et al. |
| 5,391,877 A | 2/1995 | Marks |
| 5,395,366 A | 3/1995 | D'Andrea |
| 5,399,868 A | 3/1995 | Jones et al. |
| 5,404,293 A | 4/1995 | Weng et al. |
| 5,415,181 A | 5/1995 | Hofgrefe et al. |
| 5,431,161 A | 7/1995 | Ryals et al. |
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Cornacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,507,412 A | 4/1996 | Ebert et al. |
| 5,517,120 A | 5/1996 | Misik et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,536,945 A | 7/1996 | Reich |
| 5,545,899 A | 8/1996 | Tran et al. |
| 5,547,470 A | 8/1996 | Johnson et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A | 12/1997 | Taylor et al. |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,739,508 A | 4/1998 | Uber, III |
| 5,741,232 A | 4/1998 | Reilly et al. |
| 5,742,060 A | 4/1998 | Ashburn |
| 5,744,805 A | 4/1998 | Raylman et al. |
| 5,757,006 A | 5/1998 | De Vito et al. |
| 5,779,675 A | 7/1998 | Reilly et al. |
| 5,780,855 A | 7/1998 | Pare et al. |
| 5,781,442 A | 7/1998 | Engleson et al. |
| 5,784,432 A | 7/1998 | Kurtz et al. |
| 5,786,597 A | 7/1998 | Lingren et al. |
| 5,795,333 A | 8/1998 | Reilly et al. |
| 5,799,111 A | 8/1998 | Guissin |
| 5,800,355 A | 9/1998 | Hasegawa |
| 5,803,914 A | 9/1998 | Ryals et al. |
| 5,806,519 A | 9/1998 | Evans, III et al. |
| 5,808,203 A | 9/1998 | Nolan, Jr. et al. |
| 5,810,742 A | 9/1998 | Pearlman |
| 5,811,814 A | 9/1998 | Leone et al. |
| 5,813,985 A | 9/1998 | Carroll |
| 5,814,015 A | 9/1998 | Gargano et al. |
| 5,818,050 A | 10/1998 | Dilmanian et al. |
| 5,821,541 A | 10/1998 | Tuemer |
| 5,825,031 A | 10/1998 | Wong et al. |

(56) References Cited

U.S. PATENT DOCUMENTS

| | | |
|---|---|---|
| 5,827,219 A | 10/1998 | Uber, III et al. |
| 5,828,073 A | 10/1998 | Zhu et al. |
| 5,833,603 A | 11/1998 | Kovacs et al. |
| 5,838,009 A | 11/1998 | Plummer et al. |
| 5,840,026 A | 11/1998 | Uber, III et al. |
| 5,841,141 A | 11/1998 | Gullberg et al. |
| 5,842,977 A | 12/1998 | Lesho et al. |
| 5,843,037 A | 12/1998 | Uber, III |
| 5,846,513 A | 12/1998 | Carroll et al. |
| 5,847,396 A | 12/1998 | Lingren et al. |
| 5,857,463 A | 1/1999 | Thurston et al. |
| 5,871,013 A | 2/1999 | Wainer et al. |
| 5,873,861 A | 2/1999 | Hitchins et al. |
| 5,880,475 A | 3/1999 | Oka et al. |
| 5,882,338 A | 3/1999 | Gray |
| 5,884,457 A | 3/1999 | Ortiz et al. |
| 5,885,216 A | 3/1999 | Evans, III et al. |
| 5,891,030 A | 4/1999 | Johnson et al. |
| 5,893,397 A | 4/1999 | Peterson et al. |
| 5,899,885 A | 5/1999 | Reilly et al. |
| 5,900,533 A | 5/1999 | Chou |
| 5,903,008 A | 5/1999 | Li |
| 5,910,112 A | 6/1999 | Judd et al. |
| 5,911,252 A | 6/1999 | Cassel |
| 5,916,167 A | 6/1999 | Kramer et al. |
| 5,916,197 A | 6/1999 | Reilly et al. |
| 5,920,054 A | 7/1999 | Uber, III |
| 5,927,351 A | 7/1999 | Zhu et al. |
| 5,928,150 A | 7/1999 | Call |
| 5,932,879 A | 8/1999 | Raylman et al. |
| 5,938,639 A | 8/1999 | Reilly et al. |
| 5,939,724 A | 8/1999 | Eisen et al. |
| 5,944,190 A | 8/1999 | Edelen |
| 5,944,694 A | 8/1999 | Hitchins et al. |
| 5,947,935 A | 9/1999 | Rhinehart et al. |
| 5,953,884 A | 9/1999 | Lawecki et al. |
| 5,954,668 A | 9/1999 | Uber, III et al. |
| 5,961,457 A | 10/1999 | Raylman et al. |
| 5,967,983 A | 10/1999 | Ashburn |
| 5,973,598 A | 10/1999 | Beigel |
| 5,974,165 A | 10/1999 | Giger et al. |
| 5,984,860 A | 11/1999 | Shan |
| 5,987,350 A | 11/1999 | Thurston |
| 5,993,378 A | 11/1999 | Lemelson |
| 5,997,502 A | 12/1999 | Reilly et al. |
| 6,002,134 A | 12/1999 | Lingren |
| 6,002,480 A | 12/1999 | Izatt et al. |
| 6,017,330 A | 1/2000 | Hitchins et al. |
| 6,019,745 A | 2/2000 | Gray |
| 6,021,341 A | 2/2000 | Scibilia et al. |
| 6,026,317 A | 2/2000 | Verani |
| 6,032,155 A | 2/2000 | de la Huerga |
| 6,037,595 A | 3/2000 | Lingren |
| 6,040,697 A | 3/2000 | Misic |
| 6,042,565 A | 3/2000 | Hirschman et al. |
| RE36,648 E | 4/2000 | Uber, III et al. |
| 6,046,454 A | 4/2000 | Lingren et al. |
| 6,048,334 A | 4/2000 | Hirschman et al. |
| 6,052,618 A | 4/2000 | Dahlke et al. |
| 6,055,450 A | 4/2000 | Ashburn |
| 6,055,452 A | 4/2000 | Pearlman |
| RE36,693 E | 5/2000 | Reich |
| 6,063,052 A | 5/2000 | Uber et al. |
| D426,891 S | 6/2000 | Beale et al. |
| D426,892 S | 6/2000 | Beale et al. |
| 6,072,177 A | 6/2000 | McCroskey et al. |
| 6,076,009 A | 6/2000 | Raylman et al. |
| 6,080,984 A | 6/2000 | Friesenhahn |
| D428,491 S | 7/2000 | Beale et al. |
| 6,082,366 A | 7/2000 | Andra et al. |
| 6,090,064 A | 7/2000 | Reilly et al. |
| 6,091,070 A | 7/2000 | Lingren et al. |
| 6,096,011 A | 8/2000 | Trombley, III et al. |
| 6,107,102 A | 8/2000 | Ferrari |
| 6,115,635 A | 9/2000 | Bourgeois |
| 6,116,461 A | 9/2000 | Broadfield et al. |
| 6,129,670 A | 10/2000 | Burdette et al. |
| 6,132,372 A | 10/2000 | Essen-Moller |
| 6,135,955 A | 10/2000 | Madden et al. |
| 6,135,968 A | 10/2000 | Brounstein |
| 6,137,109 A | 10/2000 | Hayes |
| 6,145,277 A | 11/2000 | Lawecki et al. |
| 6,147,352 A | 11/2000 | Ashburn |
| 6,147,353 A | 11/2000 | Gagnon et al. |
| 6,148,229 A | 11/2000 | Morris, Sr. et al. |
| 6,149,574 A | 11/2000 | Trauthen et al. |
| 6,149,627 A | 11/2000 | Uber, III |
| 6,155,485 A | 12/2000 | Coughlin et al. |
| 6,160,398 A | 12/2000 | Walsh |
| 6,162,198 A | 12/2000 | Coffey et al. |
| 6,167,294 A | 12/2000 | Busch |
| 6,172,362 B1 | 1/2001 | Lingren et al. |
| 6,173,201 B1 | 1/2001 | Front |
| 6,184,530 B1 | 2/2001 | Hines et al. |
| 6,189,195 B1 | 2/2001 | Reilly et al. |
| 6,194,715 B1 | 2/2001 | Lingren et al. |
| 6,194,725 B1 | 2/2001 | Colsher et al. |
| 6,194,726 B1 | 2/2001 | Pi et al. |
| 6,197,000 B1 | 3/2001 | Reilly et al. |
| 6,202,923 B1 | 3/2001 | Boyer et al. |
| 6,203,775 B1 * | 3/2001 | Torchilin et al. ............ 424/1.69 |
| 6,205,347 B1 | 3/2001 | Morgan et al. |
| 6,212,423 B1 | 4/2001 | Krakovitz |
| 6,223,065 B1 | 4/2001 | Misic et al. |
| 6,224,577 B1 | 5/2001 | Dedola et al. |
| 6,226,350 B1 | 5/2001 | Hsieh |
| 6,229,145 B1 | 5/2001 | Weinberg |
| 6,232,605 B1 | 5/2001 | Soluri et al. |
| 6,233,304 B1 | 5/2001 | Hu et al. |
| 6,236,050 B1 | 5/2001 | Tumer |
| 6,236,878 B1 | 5/2001 | Taylor et al. |
| 6,236,880 B1 | 5/2001 | Raylman et al. |
| 6,239,438 B1 | 5/2001 | Schubert |
| 6,240,312 B1 | 5/2001 | Alfano et al. |
| 6,241,708 B1 | 6/2001 | Reilly et al. |
| 6,242,743 B1 | 6/2001 | DeVito et al. |
| 6,242,744 B1 | 6/2001 | Soluri et al. |
| 6,242,745 B1 | 6/2001 | Berlad et al. |
| 6,246,901 B1 | 6/2001 | Benaron |
| 6,252,924 B1 | 6/2001 | Davantes et al. |
| 6,258,576 B1 | 7/2001 | Richards-Kortum et al. |
| 6,259,095 B1 | 7/2001 | Bouton et al. |
| 6,261,562 B1 | 7/2001 | Xu et al. |
| 6,263,229 B1 | 7/2001 | Atalar et al. |
| 6,269,340 B1 | 7/2001 | Ford et al. |
| 6,270,463 B1 | 8/2001 | Morris, Sr. et al. |
| 6,271,524 B1 | 8/2001 | Wainer et al. |
| 6,271,525 B1 | 8/2001 | Majewski et al. |
| 6,280,704 B1 | 8/2001 | Schutt et al. |
| 6,281,505 B1 | 8/2001 | Hines et al. |
| 6,308,097 B1 | 10/2001 | Pearlman |
| 6,310,968 B1 | 10/2001 | Hawkins et al. |
| 6,315,981 B1 | 11/2001 | Unger |
| 6,317,623 B1 | 11/2001 | Griffiths et al. |
| 6,317,648 B1 | 11/2001 | Sleep et al. |
| 6,318,630 B1 | 11/2001 | Coughlin et al. |
| 6,322,535 B1 | 11/2001 | Hitchins et al. |
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,338,007 B1 | 1/2002 | Broadfield et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,355,024 B1 | 3/2002 | Small et al. |
| 6,356,081 B1 | 3/2002 | Misic |
| 6,368,331 B1 | 4/2002 | Front et al. |
| 6,371,938 B1 | 4/2002 | Reilly et al. |

(56) References Cited

U.S. PATENT DOCUMENTS

| | | |
|---|---|---|
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,244 B1 | 5/2002 | Gagnon |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,401,071 B1 | 6/2002 | Hogan |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,415,046 B1 | 7/2002 | Kerut, Sr. |
| 6,420,711 B2 | 7/2002 | Tuemer |
| 6,425,174 B1 | 7/2002 | Riech |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,475,192 B1 | 11/2002 | Reilly et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,575,930 B1 | 6/2003 | Trombley, III et al. |
| 6,576,918 B1 | 6/2003 | Fu et al. |
| 6,583,420 B1 | 6/2003 | Nelson et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,633,658 B1 | 10/2003 | Dabney et al. |
| 6,635,879 B2 | 10/2003 | Jimbo et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engelson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 | 1/2004 | Tournier et al. |
| 6,685,678 B2 | 2/2004 | Evans et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,767,319 B2 | 7/2004 | Reilly et al. |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,809,321 B2 | 10/2004 | Rempel |
| 6,813,868 B2 | 11/2004 | Baldwin et al. |
| 6,821,013 B2 | 11/2004 | Reilly et al. |
| 6,822,237 B2 | 11/2004 | Inoue et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,861,954 B2 | 3/2005 | Levin |
| 6,866,654 B2 | 3/2005 | Callan et al. |
| 6,870,175 B2 | 3/2005 | Dell et al. |
| 6,881,043 B2 | 4/2005 | Barak |
| 6,888,351 B2 | 5/2005 | Belt et al. |
| 6,889,074 B2 | 5/2005 | Uber, III et al. |
| 6,897,658 B2 | 5/2005 | Belt et al. |
| 6,901,283 B2 | 5/2005 | Evans, III et al. |
| 6,906,330 B2 | 6/2005 | Blevis et al. |
| D507,832 S | 7/2005 | Yanniello et al. |
| 6,915,170 B2 | 7/2005 | Engleson et al. |
| 6,915,619 B2 | 7/2005 | Baldwin |

(56) References Cited

U.S. PATENT DOCUMENTS

| | | |
|---|---|---|
| 6,915,823 B2 | 7/2005 | Osborne et al. |
| 6,917,828 B2 | 7/2005 | Fukuda |
| 6,921,384 B2 | 7/2005 | Reilly et al. |
| 6,928,142 B2 | 8/2005 | Shao et al. |
| 6,935,560 B2 | 8/2005 | Andreasson et al. |
| 6,936,030 B1 | 8/2005 | Pavlik et al. |
| 6,937,750 B2 | 8/2005 | Natanzon et al. |
| 6,939,302 B2 | 9/2005 | Griffiths et al. |
| 6,940,070 B2 | 9/2005 | Turner |
| 6,943,355 B2 | 9/2005 | Shwartz et al. |
| 6,957,522 B2 | 10/2005 | Baldwin et al. |
| 6,958,053 B1 | 10/2005 | Reilly |
| 6,963,770 B2 | 11/2005 | Scarantino et al. |
| 6,970,735 B2 | 11/2005 | Uber, III et al. |
| 6,972,001 B2 | 12/2005 | Emig et al. |
| 6,974,443 B2 | 12/2005 | Reilly et al. |
| 6,976,349 B2 | 12/2005 | Baldwin et al. |
| 6,984,222 B1 | 1/2006 | Hitchins et al. |
| 6,985,870 B2 | 1/2006 | Martucci et al. |
| 6,988,981 B2 | 1/2006 | Hamazaki |
| 6,994,249 B2 | 2/2006 | Peterka et al. |
| 7,009,183 B2 | 3/2006 | Wainer et al. |
| 7,011,814 B2 | 3/2006 | Suddarth et al. |
| 7,012,430 B2 | 3/2006 | Misic |
| 7,017,622 B2 | 3/2006 | Osborne et al. |
| 7,018,363 B2 | 3/2006 | Cowan et al. |
| 7,019,783 B2 | 3/2006 | Kindem et al. |
| 7,025,757 B2 | 4/2006 | Reilly et al. |
| 7,026,623 B2 | 4/2006 | Oaknin et al. |
| 7,043,063 B1 | 5/2006 | Noble et al. |
| 7,102,138 B2 | 9/2006 | Belvis et al. |
| 7,103,204 B1 | 9/2006 | Celler et al. |
| 7,127,026 B2 | 10/2006 | Amemiya et al. |
| 7,142,634 B2 | 11/2006 | Engler et al. |
| 7,145,986 B2 | 12/2006 | Wear et al. |
| 7,147,372 B2 | 12/2006 | Nelson et al. |
| 7,164,130 B2 | 1/2007 | Welsh et al. |
| 7,176,466 B2 | 2/2007 | Rousso et al. |
| 7,187,790 B2 | 3/2007 | Sabol et al. |
| 7,217,953 B2 | 5/2007 | Carlson |
| 7,256,386 B2 | 8/2007 | Carlson et al. |
| 7,291,841 B2 | 11/2007 | Nelson et al. |
| 7,327,822 B2 | 2/2008 | Sauer et al. |
| 7,359,535 B2 | 4/2008 | Salla et al. |
| 7,373,197 B2 | 5/2008 | Daighighian et al. |
| 7,394,923 B2 | 7/2008 | Zou et al. |
| 7,444,010 B2 | 10/2008 | De Man |
| 7,468,513 B2 | 12/2008 | Charron et al. |
| 7,470,896 B2 | 12/2008 | Pawlak et al. |
| 7,490,085 B2 | 2/2009 | Walker et al. |
| 7,495,225 B2 | 2/2009 | Hefetz et al. |
| 7,502,499 B2 | 3/2009 | Grady |
| 7,570,732 B2 | 8/2009 | Stanton et al. |
| 7,592,597 B2 | 9/2009 | Hefetz et al. |
| 7,620,444 B2 | 11/2009 | Le et al. |
| 7,627,084 B2 | 12/2009 | Jabri et al. |
| 7,652,259 B2 | 1/2010 | Kimchy et al. |
| 7,671,331 B2 | 3/2010 | Hefetz |
| 7,671,340 B2 | 3/2010 | Uribe et al. |
| 7,672,491 B2 | 3/2010 | Krishnan et al. |
| 7,680,240 B2 | 3/2010 | Manjeshwar et al. |
| 7,705,316 B2 | 4/2010 | Rousso et al. |
| 7,734,331 B2 | 6/2010 | Dhawale et al. |
| 7,826,889 B2 | 11/2010 | David et al. |
| 7,831,024 B2 | 11/2010 | Metzler et al. |
| 7,835,927 B2 | 11/2010 | Schlotterbeck et al. |
| 7,872,235 B2 | 1/2011 | Rousso et al. |
| 7,894,650 B2 | 2/2011 | Weng et al. |
| 7,968,851 B2 | 6/2011 | Rousso et al. |
| 8,013,308 B2 | 9/2011 | Guerin et al. |
| 8,055,329 B2 | 11/2011 | Kimchy et al. |
| 8,111,886 B2 | 2/2012 | Rousso et al. |
| 8,158,951 B2 | 4/2012 | Bal et al. |
| 8,163,661 B2 | 4/2012 | Akiyoshi et al. |
| 8,204,500 B2 | 6/2012 | Weintraub et al. |
| 8,338,788 B2 | 12/2012 | Zilberstein et al. |
| 8,440,168 B2 | 5/2013 | Yang et al. |
| 2001/0016029 A1 | 8/2001 | Turner |
| 2001/0020131 A1 | 9/2001 | Kawagishi et al. |
| 2001/0035902 A1 | 11/2001 | Iddan et al. |
| 2001/0049608 A1 | 12/2001 | Hochman |
| 2002/0068864 A1 | 6/2002 | Bishop et al. |
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0099310 A1 | 7/2002 | Kimchy et al. |
| 2002/0099334 A1 | 7/2002 | Hanson et al. |
| 2002/0103429 A1 | 8/2002 | DeCharms |
| 2002/0103431 A1 | 8/2002 | Toker et al. |
| 2002/0145114 A1 | 10/2002 | Inoue et al. |
| 2002/0148970 A1 | 10/2002 | Wong et al. |
| 2002/0165491 A1 | 11/2002 | Reilly |
| 2002/0168094 A1 | 11/2002 | Kaushikkar et al. |
| 2002/0168317 A1 | 11/2002 | Daighighian et al. |
| 2002/0172405 A1 | 11/2002 | Schultz |
| 2002/0179843 A1 | 12/2002 | Tanaka et al. |
| 2002/0183645 A1 | 12/2002 | Nachaliel |
| 2002/0188197 A1 | 12/2002 | Bishop et al. |
| 2002/0198738 A1 | 12/2002 | Osborne |
| 2003/0001098 A1 | 1/2003 | Stoddart et al. |
| 2003/0001837 A1 | 1/2003 | Baumberg |
| 2003/0006376 A1 | 1/2003 | Turner |
| 2003/0013950 A1 | 1/2003 | Rollo et al. |
| 2003/0013966 A1 | 1/2003 | Barnes et al. |
| 2003/0038240 A1 | 2/2003 | Weinberg |
| 2003/0055685 A1 | 3/2003 | Cobb et al. |
| 2003/0063787 A1 | 4/2003 | Natanzon et al. |
| 2003/0071219 A1 | 4/2003 | Motomura et al. |
| 2003/0081716 A1 | 5/2003 | Tumer |
| 2003/0135388 A1 | 7/2003 | Martucci et al. |
| 2003/0136912 A1 | 7/2003 | Juni |
| 2003/0144322 A1 | 7/2003 | Kozikowski et al. |
| 2003/0147887 A1* | 8/2003 | Wang et al. .............. 424/144.1 |
| 2003/0158481 A1 | 8/2003 | Stotzka et al. |
| 2003/0183226 A1 | 10/2003 | Brand et al. |
| 2003/0189174 A1 | 10/2003 | Tanaka et al. |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0215122 A1 | 11/2003 | Tanaka |
| 2003/0215124 A1 | 11/2003 | Li |
| 2003/0216631 A1 | 11/2003 | Bloch et al. |
| 2003/0219149 A1 | 11/2003 | Vailaya et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0021065 A1 | 2/2004 | Weber |
| 2004/0044282 A1 | 3/2004 | Mixon et al. |
| 2004/0051368 A1 | 3/2004 | Caputo et al. |
| 2004/0054248 A1 | 3/2004 | Kimchy et al. |
| 2004/0054278 A1 | 3/2004 | Kimchy et al. |
| 2004/0065838 A1 | 4/2004 | Tumer |
| 2004/0075058 A1 | 4/2004 | Blevis et al. |
| 2004/0081623 A1 | 4/2004 | Eriksen et al. |
| 2004/0082918 A1 | 4/2004 | Evans et al. |
| 2004/0084340 A1 | 5/2004 | Morelle et al. |
| 2004/0086437 A1 | 5/2004 | Jackson |
| 2004/0101176 A1 | 5/2004 | Mendonca et al. |
| 2004/0101177 A1 | 5/2004 | Zahlmann et al. |
| 2004/0116807 A1 | 6/2004 | Amrami et al. |
| 2004/0120557 A1 | 6/2004 | Sabol |
| 2004/0122311 A1 | 6/2004 | Cosman |
| 2004/0125918 A1 | 7/2004 | Shanmugavel et al. |
| 2004/0138557 A1 | 7/2004 | Le et al. |
| 2004/0143449 A1 | 7/2004 | Behrenbruch et al. |
| 2004/0144925 A1 | 7/2004 | Stoddart et al. |
| 2004/0153128 A1 | 8/2004 | Suresh et al. |
| 2004/0156081 A1 | 8/2004 | Bril et al. |
| 2004/0162492 A1 | 8/2004 | Kobayashi |
| 2004/0171924 A1 | 9/2004 | Mire et al. |
| 2004/0183022 A1 | 9/2004 | Weinberg |
| 2004/0184644 A1 | 9/2004 | Leichter et al. |
| 2004/0193453 A1 | 9/2004 | Butterfield et al. |

(56) References Cited

U.S. PATENT DOCUMENTS

| | | |
|---|---|---|
| 2004/0195512 A1 | 10/2004 | Crosetto |
| 2004/0204646 A1 | 10/2004 | Nagler et al. |
| 2004/0205343 A1 | 10/2004 | Forth et al. |
| 2004/0210126 A1 | 10/2004 | Hajaj et al. |
| 2004/0238743 A1 | 12/2004 | Gravrand et al. |
| 2004/0251419 A1 | 12/2004 | Nelson et al. |
| 2004/0253177 A1 | 12/2004 | Elmaleh et al. |
| 2004/0263865 A1 | 12/2004 | Pawlak et al. |
| 2005/0001170 A1 | 1/2005 | Juni |
| 2005/0006589 A1 | 1/2005 | Joung et al. |
| 2005/0020898 A1 | 1/2005 | Vosniak et al. |
| 2005/0020915 A1 | 1/2005 | Belardinelli et al. |
| 2005/0023474 A1 | 2/2005 | Persyk et al. |
| 2005/0029277 A1 | 2/2005 | Tachibana |
| 2005/0033157 A1 | 2/2005 | Klein et al. |
| 2005/0049487 A1 | 3/2005 | Johnson et al. |
| 2005/0055174 A1 | 3/2005 | David et al. |
| 2005/0056788 A1 | 3/2005 | Juni |
| 2005/0074402 A1 | 4/2005 | Cagnolini et al. |
| 2005/0088306 A1 | 4/2005 | Andreasson |
| 2005/0107698 A1 | 5/2005 | Powers et al. |
| 2005/0107914 A1 | 5/2005 | Engleson et al. |
| 2005/0108044 A1 | 5/2005 | Koster |
| 2005/0113945 A1 | 5/2005 | Engleson et al. |
| 2005/0121505 A1 | 6/2005 | Metz et al. |
| 2005/0131270 A1 | 6/2005 | Weil et al. |
| 2005/0131397 A1 | 6/2005 | Levin |
| 2005/0131579 A1 | 6/2005 | Andreasson |
| 2005/0145797 A1 | 7/2005 | Oaknin et al. |
| 2005/0148869 A1 | 7/2005 | Masuda |
| 2005/0149350 A1 | 7/2005 | Kerr et al. |
| 2005/0156115 A1 | 7/2005 | Kobayashi et al. |
| 2005/0171815 A1 | 8/2005 | Vanderveen |
| 2005/0173643 A1 | 8/2005 | Tumer |
| 2005/0187465 A1 | 8/2005 | Motomura et al. |
| 2005/0198800 A1 | 9/2005 | Reich |
| 2005/0203389 A1 | 9/2005 | Williams |
| 2005/0205792 A1 | 9/2005 | Rousso et al. |
| 2005/0205796 A1 | 9/2005 | Bryman |
| 2005/0207526 A1 | 9/2005 | Altman |
| 2005/0211909 A1 | 9/2005 | Smith |
| 2005/0215889 A1 | 9/2005 | Patterson, II |
| 2005/0234424 A1 | 10/2005 | Besing et al. |
| 2005/0240441 A1 | 10/2005 | Suzuki |
| 2005/0247893 A1 | 11/2005 | Fu et al. |
| 2005/0253073 A1 | 11/2005 | Joram et al. |
| 2005/0261936 A1 | 11/2005 | Silverbrook et al. |
| 2005/0261937 A1 | 11/2005 | Silverbrook et al. |
| 2005/0261938 A1 | 11/2005 | Silverbrook et al. |
| 2005/0266074 A1 | 12/2005 | Zilberstein et al. |
| 2005/0277833 A1 | 12/2005 | Williams, Jr. |
| 2005/0277911 A1 | 12/2005 | Stewart et al. |
| 2005/0278066 A1 | 12/2005 | Graves et al. |
| 2005/0288869 A1 | 12/2005 | Kroll et al. |
| 2006/0000983 A1 | 1/2006 | Charron et al. |
| 2006/0033028 A1 | 2/2006 | Juni |
| 2006/0036157 A1 | 2/2006 | Tumer |
| 2006/0072799 A1 | 4/2006 | McLain |
| 2006/0074290 A1 | 4/2006 | Chen et al. |
| 2006/0104519 A1 | 5/2006 | Stoeckel et al. |
| 2006/0109950 A1 | 5/2006 | Arenson et al. |
| 2006/0122503 A1 | 6/2006 | Burbank et al. |
| 2006/0145081 A1 | 7/2006 | Hawman |
| 2006/0160157 A1 | 7/2006 | Zuckerman |
| 2006/0188136 A1 | 8/2006 | Ritt et al. |
| 2006/0214097 A1 | 9/2006 | Wang et al. |
| 2006/0237652 A1 | 10/2006 | Kimchy et al. |
| 2006/0257012 A1 | 11/2006 | Kaufman et al. |
| 2007/0081700 A1 | 4/2007 | Blumenfeld et al. |
| 2007/0116170 A1 | 5/2007 | De Man et al. |
| 2007/0133852 A1 | 6/2007 | Collins et al. |
| 2007/0156047 A1 | 7/2007 | Nagler et al. |
| 2007/0166227 A1 | 7/2007 | Liu et al. |
| 2007/0189436 A1 | 8/2007 | Goto et al. |
| 2007/0194241 A1 | 8/2007 | Rousso et al. |
| 2007/0265230 A1 | 11/2007 | Rousso et al. |
| 2008/0001090 A1 | 1/2008 | Ben-Haim et al. |
| 2008/0029704 A1 | 2/2008 | Hefetz et al. |
| 2008/0033291 A1 | 2/2008 | Rousso et al. |
| 2008/0036882 A1 | 2/2008 | Uemura et al. |
| 2008/0039721 A1 | 2/2008 | Shai et al. |
| 2008/0042067 A1 | 2/2008 | Rousso et al. |
| 2008/0128626 A1 | 6/2008 | Rousso et al. |
| 2008/0137938 A1 | 6/2008 | Zahniser |
| 2008/0230702 A1 | 9/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260580 A1 | 10/2008 | Helle et al. |
| 2008/0260637 A1 | 10/2008 | Dickman |
| 2008/0277591 A1 | 11/2008 | Shahar et al. |
| 2009/0001273 A1 | 1/2009 | Hawman |
| 2009/0018412 A1 | 1/2009 | Schmitt |
| 2009/0078875 A1 | 3/2009 | Rousso et al. |
| 2009/0112086 A1 | 4/2009 | Melman |
| 2009/0152471 A1 | 6/2009 | Rousso et al. |
| 2009/0190807 A1 | 7/2009 | Rousso et al. |
| 2009/0201291 A1 | 8/2009 | Ziv et al. |
| 2009/0236532 A1 | 9/2009 | Frach et al. |
| 2009/0304582 A1 | 12/2009 | Rousso et al. |
| 2010/0006770 A1 | 1/2010 | Balakin |
| 2010/0021378 A1 | 1/2010 | Rousso et al. |
| 2010/0102242 A1 | 4/2010 | Burr et al. |
| 2010/0121184 A1 | 5/2010 | Dhawale et al. |
| 2010/0140483 A1 | 6/2010 | Rousso et al. |
| 2010/0202664 A1 | 8/2010 | Busch et al. |
| 2010/0245354 A1 | 9/2010 | Rousso et al. |
| 2012/0106820 A1 | 5/2012 | Rousso et al. |
| 2012/0172699 A1 | 7/2012 | Nagler et al. |
| 2012/0248320 A1 | 10/2012 | Wangerin et al. |
| 2012/0326034 A1 | 12/2012 | Sachs et al. |
| 2013/0114792 A1 | 5/2013 | Zilberstein et al. |
| 2013/0308749 A1 | 11/2013 | Zilberstein et al. |
| 2014/0151563 A1 | 6/2014 | Rousso et al. |
| 2014/0163368 A1 | 6/2014 | Rousso et al. |
| 2014/0187927 A1 | 7/2014 | Nagler et al. |
| 2014/0193336 A1 | 7/2014 | Rousso et al. |
| 2014/0200447 A1 | 7/2014 | Rousso et al. |

FOREIGN PATENT DOCUMENTS

| | | |
|---|---|---|
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 06-109848 | 4/1994 |
| JP | 07-059763 | 3/1995 |
| JP | 07-141523 | 6/1995 |
| JP | 08-292268 | 11/1996 |
| JP | 10-260258 | 9/1998 |
| JP | 11-072564 | 3/1999 |
| WO | WO 92/00402 | 1/1992 |
| WO | WO 98/16852 | 4/1998 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/25268 | 5/2000 |
| WO | WO 00/31522 | 6/2000 |
| WO | WO 00/38197 | 6/2000 |
| WO | WO 01/89384 | 11/2001 |
| WO | WO 02/16965 | 2/2002 |
| WO | WO 02/058531 | 8/2002 |

(56) References Cited

FOREIGN PATENT DOCUMENTS

| WO | WO 02/075357 | 9/2002 |
|---|---|---|
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Dewaraja YK, Wilderman SJ, Ljungberg M, Koral KF, Zasadny K, Kaminiski MS. Accurate dosimetry in 131I radionuclide therapy using patient-specific, 3-dimensional methods for SPECT reconstruction and absorbed dose calculation. 2005 J. Nucl. Med. May 1; 46: 840-849.*

Volkow ND, Rosen B, Farde L. Imaging the living human brain: magnetic resonance imaging and positron emission tomography. 1997 Proc. Natl. Acad. Sci. USA. 94: 2787-2788.*

Trikha M, Yan L, Nakada MT. Monoclonal antibodies as therapeutics in oncology. 2002 Curr. Opin. Biotechnol. 13: 609-614.*

Saltz LB, Lenz H, Kindler H, Hochster H, Wadler S, Hoff P, Kemeny N, Hollywood E, Gonen M, Chen H. Interim report of randomized phase II trial of cetuximab/bevacizumab/irinotecan (CBI) versus cetuximab/bevacizumab (CB) in irinotecan-refractory colorectal cancer. Jan. 27-29, 2005 Gastrointestinal Cancers Symposium: Abstract 169b, 4 p total.*

U.S. Appl. No. 60/625,971, filed Nov. 9, 2004.
U.S. Appl. No. 60/628,105, filed Nov. 17, 2004.
U.S. Appl. No. 60/630,561, filed Nov. 26, 2004.
U.S. Appl. No. 60/632,236, filed Dec. 2, 2004.
U.S. Appl. No. 60/635,630, filed Dec. 14, 2004.
U.S. Appl. No. 60/632,515, filed Dec. 3, 2004.
U.S. Appl. No. 60/675,892, filed Apr. 29, 2005.
U.S. Appl. No. 60/691,780, filed Jun. 20, 2005.
U.S. Appl. No. 60/700,318, filed Jul. 19, 2005.
U.S. Appl. No. 60/700,299, filed Jul. 19, 2005.
U.S. Appl. No. 60/636,088, filed Dec. 16, 2004.
U.S. Appl. No. 60/648,385, filed Jan. 2, 2005.
U.S. Appl. No. 60/640,215, filed Jan. 3, 2005.
U.S. Appl. No. 60/648,690, filed Feb. 2, 2005.
U.S. Appl. No. 60/700,317, filed Jul. 19, 2005.
U.S. Appl. No. 60/700,753, filed May 20, 2005.
U.S. Appl. No. 60/700,752, filed Jul. 20, 2005.
U.S. Appl. No. 60/702,979, filed Jul. 28, 2005.
U.S. Appl. No. 60/720,034, filed Sep. 9, 2005.
U.S. Appl. No. 60/720,652, filed Sep. 27, 2005.
U.S. Appl. No. 60/720,541, filed Sep. 27, 2005.
U.S. Appl. No. 60/750,287, filed Dec. 13, 2005.
U.S. Appl. No. 60/750,334, filed Dec. 13, 2005.
U.S. Appl. No. 60/750,597, filed Dec. 15, 2005.
U.S. Appl. No. 60/800,845, filed May 17, 2006.
U.S. Appl. No. 60/800,846 filed May 17, 2006.
U.S. Appl. No. 60/816,970, filed Jun. 6, 2006.

Bisset, et al—Reference Values for Peripheral Blood Lymphocyte Phenotypes Appicable to the Healthy Adult Population in Switzerland—European Journal of Hematology 72(3):203-212—Mar. 2004, Abstract only.

Ginaldi, et al—Levels of Expression of CD19 and CD20 in Chronic B-Cell Leukaemias—Journal of Clinical Pathology 51:364-369—1998.

Massoud, et al—Molecular Imaging in Living Subjects: Seeing Fundamental Biological Processes in a New Light—Genes & Dev. 17:545-580—2003.

Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.

Lange et al. "EM Reconstruction Algorithms for Emission and Transmission Tomography", Journal of Computer Assisted Tomography, 8(2): 306-316, Apr. 1984.

Ohrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.

Rockmore et al. "A Maximum Likelihood Approach to Emission Image Reconstruction From Projections", IEEE Transactions on Nuclear Science, 23(4): 1428-1432, Aug. 1976.

Shepp et al. "Maximum Likelihood Reconstruction for Emission Tomography", IEEE Transactions on Medical Imaging, MI-1: 113-122, Oct. 1982.

Sitek et al. "Reconstruction of Dynamic Renal Tomographic Data Acquired by Slow Rotation", The Journal of Nuclear Medicine, 42(11): 1704-1712, Nov. 2001.

Solanki "The Use of Automation in Radiopharmacy", Hospital Pharmacist, 7(4): 94-98, Apr. 2000.

Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.

Applicant-Initiated Interview Summary Dated May 1, 2013 From the US Patent and Trademark Office Re. U.S. Appl. No. 10/343,792.

Applicant-Initiated Interview Summary Dated May 1, 2013 From the US Patent and Trademark Office Re. U.S. Appl. No. 11/980,653.

Official Action Dated Nov. 15, 2013 From the US Patent and Trademark Office Re. U.S. Appl. No. 13/345,773.

Communication Pursuant to Article 94(3) EPC Dated Nov. 25, 2013 From the European Patent Office Re. Application No. 06756258.7.

Notice of Allowance Dated Dec. 17, 2013 From the US Patent and Trademark Office Re. U.S. Appl. No. 13/913,804.

Official Action Dated Dec. 16, 2013 From the US Patent and Trademark Office Re. U.S. Appl. No. 12/087,150.

Applicant-Initiated Interview Summary Dated Jan. 29, 2014 From the US Patent and Trademark Office Re. U.S. Appl. No. 13/345,773.

Official Action Dated Aug. 5, 2013 From the US Patent and Trademark Office Re. U.S. Appl. No. 12/309,479.

Official Action Dated Aug. 14, 2013 From the US Patent and Trademark Office Re. U.S. Appl. No. 12/448,473.

Berman et al. "D-SPECT: A Novel Camera for High Speed Quantitative Molecular Imaging: Initial Clinical Results", The Journal of Nuclear Medicine, 47(Suppl.1): 131P, 2006.

Berman et al. "Myocardial Perfusion Imaging With Technetium-99m-Sestamibi: Comparative Analysis of Available Imaging Protocols", The Journal of Nuclear Medicine, 35: 681-688, 1994.

Borges-Neto et al. "Perfusion and Function at Rest and Treadmill Exercise Using Technetium-99m-Sestamibi: Comparison of One- and Two-Day Protocols in Normal Volunteers", The Journal of Nuclear Medicine, 31(7): 1128-1132, Jul. 1990.

Kwok et al. "Feasability of Simultaneous Dual-Isotope Myocardial Perfusion Acquisition Using a Lower Dose of Sestamibi", European Journal of Nuclear Medicine, 24(3): 281-285, Mar. 1997.

Patton et al. "D-SPECT: A New Solid State Camera for High Speed Molecular Imaging", The Journal of Nuclear Medicine, 47(Suppl.1): 189P, 2006.

Communication Pursuant to Article 94(3) EPC Dated Sep. 16, 2013 From the European Patent Office Re.: Application No. 06832278.3.

Official Action Dated Sep. 5, 2013 From the US Patent and Trademark Office Re. U.S. Appl. No. 13/947,198.

(56) References Cited

OTHER PUBLICATIONS

Official Action Dated Dec. 19, 2012 Re. U.S. Appl. No. 12/448,473.
Advisory Action Before the Filing of an Appeal Brief Dated Feb. 26, 2013 From the US Patent and Trademark Office Re. U.S. Appl. No. 12/514,785.
Notice of Allowance Dated Feb. 21, 2013 From the US Patent and Trademark Office Re. U.S. Appl. No. 11/798,017.
Notice of Allowance Dated Mar. 14, 2013 From the US Patent and Trademark Office Re.: U.S. Appl. No. 11/798,017.
Official Action Dated Mar. 11, 2013 From the US Patent and Trademark Office Re. U.S. Appl. No. 13/345,719.
Advisory Action before the Filing of an Appeal Brief Dated May 21, 2013 From the US Patent and Trademark Office Re. U.S. Appl. No. 11/980,653.
Applicant-Initiated Interview Summary Dated May 9, 2013 From the US Patent and Trademark Office Re. U.S. Appl. No. 12/448,473.
Advisory Action Before the Filing of an Appeal Brief Dated Feb. 26, 2013 From the US Patent and Trademark Office Re. U.S. Appl. No. 11/989,223.
Official Action Dated Nov. 30, 2012 From the US Patent and Trademark Office Re. U.S. Appl. No. 11/989,223.
Notice of Allowance Dated Jun. 21, 2013 From the US Patent and Trademark Office Re. U.S. Appl. No. 11/980,653.
Notice of Allowance Dated Jun. 14, 2013 From the US Patent and Trademark Office Re. U.S. Appl. No. 10/616,307.
Official Action Dated Jun. 12, 2013 From the US Patent and Trademark Office Re. U.S. Appl. No. 12/087,150.
Bacharach et al. "Attenuation Correction in Cardiac Positron Emission Tomography and Single-Photon Emission Computed Tomography", Journal of Nucelar Cardiology, 2(3): 246-255, 1995.
Uni Magdeburg "Attenuation Map", University of Magdeburg, Germany, Retrieved From the Internet, Archived on Jul. 31, 2002.
Zaidi et al. "Determination of the Attenuation Map in Emission Tomography", Journal of Nuclear Medicine, 44(2): 291-315, 2003.
Notice of Allowance Dated Jul. 15, 2013 From the US Patent and Trademark Office Re. U.S. Appl. No. 11/932,987.
Official Action Dated Jul. 5, 2013 From the US Patent and Trademark Office Re.: U.S. Appl. No. 11/656,548.
Official Action Dated Oct. 11, 2012 From the US Patent and Trademark Office Re. U.S. Appl. No. 11/976,852.
Communication Pursuant to Article 94(3) EPC Dated Sep. 17, 2012 From the European Patent Office Re. Application No. 06832278.3.
Ouyang et al. "Incorporation of Correlated Structural Images in PET Image Reconstruction", IEEE Transactions of Medical Imaging, 13(4): 627-640, Dec. 1994.
Official Action Dated Oct. 10, 2012 From the US Patent and Trademark Office Re. U.S. Appl. No. 11/798,017.
Communication Under Rule 71(3) EPC Dated Feb. 26, 2013 From the European Patent Office Re. Application No. 06756259.5.
Official Action Dated Feb. 22, 2013 From the US Patent and Trademark Office Re.: U.S. Appl. No. 10/616,307.
Van Den Bossche B et al., "Receptor Imaging in Oncology by Means of Nuclear Medicine: Current Status", Journal of Clinical Oncology 22(17): 3593-3607, 2004 (an abstract).
Yao D et al., "The utility of monoclonal antibodies in the imaging of prostate cancer", Semin Urol Oncol 20(3):211-8, 2002 (an abstract).
Van der Laken CJ et al., "Technetium-99m-labeled chemotactic peptides in acute infection and sterile inflammation", J Nucl Med 38(8):1310-5, 1997 (an abstract).
Babich JW et al., "Localization of radiolabeled chemotactic peptide at focal sites of *Escherichia coli* infection in rabbits: evidence for a receptor-specific mechanism", J Nucl Med 38(8):1316-22, 1997 (an abstract).
Rao PS et al., "99mTc-peptide-peptide nucleic acid probes for imaging oncogene mRNAs in tumours", Nuclear Medicine Communications 24(8):857-863, 2003 (an abstract).
Fischman AJ et al., "Infection imaging with technetium-99m-labeled chemotactic peptide analogs", Semin Nucl Med 24(2) :154-68, 1994 (an abstract).

Massoud TF et al., "Molecular imaging in living subjects: seeing fundamental biological processes in a new light", Genes & development 17:545-580, 2003.
Gambhir SS, "Molecular imaging of cancer with positron emission tomography", Nature Reviews 2:683-693, 2002.
"Keeping Pace with Targeted Therapies in Lung Cancer" Highlights from the ASCO 2006 Annual Meeting, 2006.
Notice of Allowance Dated Dec. 26, 2012 From the US Patent and Trademark Office Re.: U.S. Appl. No. 11/980,690.
Official Action Dated Dec. 28, 2012 From the US Patent and Trademark Office Re.: U.S. Appl. No. 10/343,792.
Charland et al. "The Use of Deconvolution and Total Least Squares in Recovering a Radiation Detector Line Spread Function", Medical Physics, 25(2): 152-160, Feb. 1998. Abstract Only!
Applicant-Initiated Interview Summary Dated Jan. 28, 2013 Re.: U.S. Appl. No. 11/798,017.
Official Action Dated Feb. 7, 2013 Re. U.S. Appl. No. 11/980,653.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Jan et al. "Preliminary Results From the AROPET", IEEE Nuclear Science Symposium Conference Record, Nov. 4-10, 2001, 3: 1607-1610, 2001.
Ohno et al. "Selection of Optimum Projection Angles in Three Dimensional Myocardial SPECT", IEEE Nuclear Science Symposium Conference Record 2001, 4: 2166-2169, 2001.
Seret et al. "Intrinsic Uniforufity Requirements for Pinhole SPECT", Journal of Nuclear Medicine Technology, 34(1): 43-47, Mar. 2006.
Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.
Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.
Communication Pursuant to Article 94(3) EPC Dated Oct. 26, 2012 From the European Patent Office Re. Application No. 05803689.8.
Official Action Dated Feb. 10, 2014 From the US Patent and Trademark Office Re. U.S. Appl. No. 11/667,793.
Applicant-Initiated Interview Summary Dated Mar. 20, 2014 From the US Patent and Trademark Office Re. U.S. Appl. No. 12/087,150.
Official Action Dated Apr. 11, 2014 From the US Patent and Trademark Office Re. U.S. Appl. No. 12/309,479.
Sharir et al. "D-SPECT: High Speed Myocardial Perfusion Imaging: A Comparison With Dual Detector Anger Camera (A-SPECT)", The Journal of Nuclear Medicine, 48(Suppl.2): 51P, # 169, 2007.
Notice of Allowance Dated May 28, 2014 From the US Patent and Trademark Office Re. U.S. Appl. No. 13/345,773.
Official Action Dated May 13, 2014 From the US Patent and Trademark Office Re. U.S. Appl. No. 12/448,473.
Communication Pursuant to Article 94(3) EPC Dated May 8, 2014 From the European Patent Office Re. Application No. 05803689.8.
Official Action Dated Jun. 17, 2014 From the US Patent and Trademark Office Re. U.S. Appl. No. 12/087,150.
Restriction Official Action Dated Aug. 16, 2012 From the US Patent and Trademark Office Re. U.S. Appl. No. 12/448,473.
USPTO Office Action issued Feb. 4, 2011 in U.S. Appl. No. 11/750,057.
USPTO Office Action issued Feb. 17, 2011 in U.S. Appl. No. 11/932,987.
USPTO Office Action issued Feb. 18, 2011 in U.S. Appl. No. 11/932,872.
USPTO Office Action issued Oct. 7, 2011 in U.S. Appl. No. 11/750,057.
USPTO Office Action issued Oct. 7, 2011 in U.S. Appl. No. 11/932,872.
USPTO Office Action issued Dec. 22, 2011 in U.S. Appl. No. 12/514,785.
Official Action Dated Aug. 31, 2012 From the US Patent and Trademark Office Re. U.S. Appl. No. 11/980,653.

(56) References Cited

OTHER PUBLICATIONS

Advisory Action Before the Filing of an Appeal Brief Dated Jul. 12, 2012 From the US Patent and Trademark Office Re. U.S. Appl. No. 11/667,793.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 2, 2011 From the European Patent Office Re.: Application No. 06756259.5.
Communication Pursuant to Article 94(3) EPC Dated Mar. 8, 2010 From the European Patent Office Re.: Application No. 06832278.3.
Communication Pursuant to Article 94(3) EPC Dated Jun. 11, 2012 From the European Patent Office Re.: Application No. 06756259.5.
Communication Pursuant to Article 94(3) EPC Dated May 12, 2010 From the European Patent Office Re. Application No. 06809851.6.
Communication Pursuant to Article 94(3) EPC Dated May 12, 2010 From the European Patent Office Re.: Application No. 06809851.6.
Communication Pursuant to Article 94(3) EPC Dated Apr. 16, 2010 From the European Patent Office Re. Application No. 01951883.6.
Communication Pursuant to Article 94(3) EPC Dated Nov. 18, 2011 From the European Patent Office Re. Application No. 05803689.8.
Communication Pursuant to Article 94(3) EPC Dated Oct. 21, 2009 From the European Patent Office Re.: Application No. 02716285.8.
Communication Pursuant to Article 94(3) EPC Dated Jul. 22, 2009 From the European Patent Office Re.: Application No. 06809851.6.
Communication Pursuant to Article 94(3) EPC Dated Sep. 22, 2011 From the European Patent Office Re. Application No. 06756258.7.
Communication Pursuant to Article 94(3) EPC Dated Sep. 23, 2011 From the European Patent Office Re.: Application No. 06832278.3.
Communication Pursuant to Article 94(3) EPC Dated May 29, 2012 From the European Patent Office Re. Application No. 05803689.8.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Pursuant to Rules 70(2) and 70a(2) EPC Dated Apr. 4, 2011 From the European Patent Office Re. Application No. 05803689.8.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
Communication Under Rule 71(3) EPC Dated May 30, 2012 From the European Patent Office Re.: Application No. 02716285.8.
Examination Report Dated Jun. 22, 2011 From the Government of India, Patent Office, Intellectual Property Building Re. Application No. 2963/CHENP/2006.
International Preliminary Report on Patentability Dated Apr. 7, 2009 From the International Bureau of WIPO Re. Application No. PCT/IL2007/000918.
International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 10, 2006 From the International Searching Authority of the Patent Cooperation Treaty Re.: Application No. PCT/IL06/00059.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 1, 2008 From the International Searching Authority Re. Application No. PCT/IL2006/000834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
International Search Report Dated Jul. 2, 2007 From the International Searching Authority Re. Application No. PCT/IL2006/001291.
International Search Report Dated Aug. 3, 2006 From the International Searching Authority of the Patent Cooperation Treaty Re.: Application No. PCT/IL05/001173.
International Search Report Dated Aug. 3, 2006 From the International Searching Authority Re. Application No. PCT/IL2005/001173.
International Search Report Dated Jul. 11, 2008 From the International Searching Authority of the Patent Cooperation Treaty Re.: Application No. PCT/IL06/01511.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Sep. 12, 2002 From the International Searching Authority of the Patent Cooperation Treaty Re: Application No. PCT/IL02/00057.
International Search Report Dated Oct. 15, 2008 From the International Searching Authority Re. Application No. PCT/2007/000918.
International Search Report Dated Oct. 15, 2008 From the International Searching Authority Re.: Application No. PCT/IL07/00918.
International Search Report Dated Mar. 18, 2004 From the International Searching Authority of the Patent Cooperation Treaty Re.: Application No. PCT/IL03/00917.

(56) References Cited

OTHER PUBLICATIONS

International Search Report Dated Mar. 23, 2006 From the International Searching Authority of the Patent Cooperation Treaty Re.: Application No. PCT/IL05/00572.
International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Interview Summary Dated Mar. 25, 2011 From the US Patent and Trademark Office Re.: U.S. Appl. No. 10/836,223.
Interview Summary Dated May 31, 2011 From the US Patent and Trademark Office Re. U.S. Appl. No. 10/616,301.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Notice of Allowance Dated Feb. 2, 2012 From the US Patent and Trademark Office Re. U.S. Appl. No. 11/628,074.
Notice of Allowance Dated May 5, 2011 From the US Patent and Trademark Office Re.: U.S. Appl. No. 10/240,239.
Notice of Allowance Dated May 6, 2011 From the US Patent and Trademark Office Re. U.S. Appl. No. 11/980,617.
Notice of Allowance Dated Oct. 11, 2011 From the US Patent and Trademark Office Re. U.S. Appl. No. 11/988,926.
Notice of Allowance Dated Nov. 15, 2010 From the US Patent and Trademark Office Re. U.S. Appl. No. 10/616,301.
Notice of Allowance Dated Jul. 16, 2009 From the US Patent and Trademark Office Re.: U.S. Appl. No. 12/084,559.
Notice of Allowance Dated Sep. 16, 2011 From the US Patent and Trademark Office Re.: U.S. Appl. No. 11/607,075.
Notice of Allowance Dated Dec. 17, 2010 From the US Patent and Trademark Office Re. U.S. Appl. No. 11/980,617.
Notice of Allowance Dated Sep. 17, 2009 From the US Patent and Trademark Office Re.: U.S. Appl. No. 10/533,568. Suppl. IDS VIII in 25855.
Notice of Allowance Dated Jul. 22, 2010 From the US Patent and Trademark Office Re.: U.S. Appl. No. 11/794,799.
Notice of Allowance Dated Feb. 23, 2011 From the US Patent and Trademark Office Re.: U.S. Appl. No. 12/728,383.
Notice of Allowance Dated Jun. 23, 2011 From the US Patent and Trademark Office Re.: U.S. Appl. No. 10/616,301.
Notice of Allowance Dated Nov. 23, 2009 From the US Patent and Trademark Office Re.: U.S. Appl. No. 12/084,559.
Notice of Allowance Dated Aug. 25, 2010 From the US Patent and Trademark Office Re. U.S. Appl. No. 11/980,617.
Notice of Allowance Dated Jun. 30, 2010 From the US Patent and Trademark Office Re.: U.S. Appl. No. 09/727,464.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Notice of Non-Compliant Amendment Dated Feb. 14, 2011 From the US Patent and Trademark Office Re.: U.S. Appl. No. 10/616,307.
Notice of Panel Decision From Pre-Appeal Brief Review Dated Feb. 29, 2012 From the US Patent and Trademark Office Re.: U.S. Appl. No. 10/836,223.
Office Action Dated Dec. 2, 2007 From the Israeli Patent Office Re.: Application No. 158442.
Office Action Dated Jan. 2, 2006 From the Israeli Patent Office Re.: Application No. 154323.
Office Action Dated Sep. 4, 2007 From the Israeli Patent Office Re.: Application No. 157007.
Office Action Dated Jul. 17, 2007 From the Israeli Patent Office Re.: Application No. 154323 and Its Translation Into English.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Mar. 1, 2010 From the US Patent and Trademark Office Re.: U.S. Appl. No. 11/794,799.
Official Action Dated Mar. 1, 2012 From the US Patent and Trademark Office Re.: U.S. Appl. No. 10/616,307.
Official Action Dated Nov. 1, 2010 From the US Patent and Trademark Office Re. U.S. Appl. No. 12/728,383.
Official Action Dated Nov. 1, 2010 From the US Patent and Trademark Office Re.: U.S. Appl. No. 12/728,383.
Official Action Dated Sep. 1, 2009 From the US Patent and Trademark Office Re.: U.S. Appl. No. 11/794,799.
Official Action Dated Aug. 2, 2012 From the US Patent and Trademark Office Re. U.S. Appl. No. 12/087,150.
Official Action Dated Jul. 2, 2004 From the US Patent and Trademark Office Re.: U.S. Appl. No. 09/641,973.
Official Action Dated Mar. 2, 2010 From the US Patent and Trademark Office Re. U.S. Appl. No. 11/980,617.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Sep. 2, 2009 From the US Patent and Trademark Office Re.: U.S. Appl. No. 10/343,792.
Official Action Dated Aug. 3, 2010 From the US Patent and Trademark Office Re.: U.S. Appl. No. 11/980,690.
Official Action Dated May 3, 2007 From the US Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the US Patent and Trademark Office Re.: U.S. Appl. No. 12/084,559.
Official Action Dated Mar. 6, 2012 From the US Patent and Trademark Office Re. U.S. Appl. No. 12/792,856.
Official Action Dated Jan. 7, 2009 From the US Patent and Trademark Office Re.: U.S. Appl. No. 10/616,307.
Official Action Dated Jul. 7, 2009 From the US Patent and Trademark Office Re.: U.S. Appl. No. 10/533,568.
Official Action Dated Oct. 7, 2008 From the US Patent and Trademark Office Re.: U.S. Appl. No. 10/616,301.
Official Action Dated Apr. 8, 2010 From the US Patent and Trademark Office Re.: U.S. Appl. No. 11/980,690.
Official Action Dated Dec. 8, 2009 From the US Patent and Trademark Office Re.: U.S. Appl. No. 11/132,320.
Official Action Dated Dec. 8, 2010 From the US Patent and Trademark Office Re. U.S. Appl. No. 11/980,690.
Official Action Dated Dec. 8, 2010 From the US Patent and Trademark Office Re.: U.S. Appl. No. 09/641,973.
Official Action Dated Dec. 8, 2010 From the US Patent and Trademark Office Re.: U.S. Appl. No. 11/980,690.
Official Action Dated Jan. 8, 2010 From the US Patent and Trademark Office Re.: U.S. Appl. No. 11/656,548.
Official Action Dated Apr. 9, 2010 From the US Patent and Trademark Office Re. U.S. Appl. No. 11/798,017.
Official Action Dated Apr. 9, 2010 From the US Patent and Trademark Office Re.: U.S. Appl. No. 11/798,017.
Official Action Dated Mar. 9, 2011 From the US Patent and Trademark Office Re.: U.S. Appl. No. 10/616,301.
Official Action Dated Aug. 10, 2007 From the US Patent and Trademark Office Re.: U.S. Appl. No. 10/836,223.
Official Action Dated Nov. 10, 2010 From the US Patent and Trademark Office Re.: U.S. Appl. No. 10/616,307.
Official Action Dated Nov. 10, 2010 From the US Patent and Trademark Office Re.: U.S. Appl. No. 10/836,223.
Official Action Dated Aug. 11, 2009 From the US Patent and Trademark Office Re.: U.S. Appl. No. 09/641,973.
Official Action Dated Jul. 11, 2011 From the US Patent and Trademark Office Re.: U.S. Appl. No. 11/980,683.
Official Action Dated Mar. 11, 2010 From the US Patent and Trademark Office Re.: U.S. Appl. No. 11/607,075.

(56) References Cited

OTHER PUBLICATIONS

Official Action Dated Jul. 12, 2007 From the US Patent and Trademark Office Re.: U.S. Appl. No. 10/616,301.
Official Action Dated Jul. 12, 2011 From the US Patent and Trademark Office Re.: U.S. Appl. No. 09/641,973.
Official Action Dated Sep. 12, 2011 From the US Patent and Trademark Office Re. U.S. Appl. No. 12/087,150.
Official Action Dated Aug. 13, 2008 From the US Patent and Trademark Office Re. U.S. Appl. No. 11/769,826.
Official Action Dated Dec. 13, 2007 From the US Patent and Trademark Office Re.: U.S. Appl. No. 10/616,301.
Official Action Dated May 13, 2009 From the US Patent and Trademark Office Re.: U.S. Appl. No. 11/798,017.
Official Action Dated Sep. 13, 2011 From the US Patent and Trademark Office Re. U.S. Appl. No. 11/976,852.
Official Action Dated May 14, 2009 From the US Patent and Trademark Office Re.: U.S. Appl. No. 11/656,548.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Dec. 15, 2011 From the US Patent and Trademark Office Re.: U.S. Appl. No. 10/343,792.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Jul. 15, 2009 From the US Patent and Trademark Office Re.: U.S. Appl. No. 10/616,301.
Official Action Dated Mar. 15, 2004 From the US Patent and Trademark Office Re.: U.S. Appl. No. 09/765,316.
Official Action Dated Mar. 15, 2011 From the US Patent and Trademark Office Re.: U.S. Appl. No. 10/343,792.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Apr. 16, 2012 From the US Patent and Trademark Office Re.: U.S. Appl. No. 10/836,223.
Official Action Dated Dec. 16, 2008 From the US Patent and Trademark Office Re.: U.S. Appl. No. 10/343,792.
Official Action Dated Sep. 16, 2009 From the US Patent and Trademark Office Re.: U.S. Appl. No. 09/727,464.
Official Action Dated Jan. 17, 2006 From the US Patent and Trademark Office Re.: U.S. Appl. No. 11/034,007.
Official Action Dated May 18, 2012 From the US Patent and Trademark Office Re. U.S. Appl. No. 11/989,223.
Official Action Dated May 18, 2012 From the US Patent and Trademark Office Re. U.S. Appl. No. 12/514,785.
Official Action Dated Apr. 19, 2012 From the US Patent and Trademark Office Re. U.S. Appl. No. 11/750,057.
Official Action Dated Jan. 19, 2012 From the US Patent and Trademark Office Re. U.S. Appl. No. 11/667,793.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Official Action Dated Mar. 19, 2010 From the US Patent and Trademark Office Re.: U.S. Appl. No. 10/240,239.
Official Action Dated Apr. 20, 2006 From the US Patent and Trademark Office Re.: U.S. Appl. No. 10/240,239.
Official Action Dated Apr. 20, 2011 From the US Patent and Trademark Office Re. U.S. Appl. No. 11/798,017.
Official Action Dated Apr. 20, 2011 From the US Patent and Trademark Office Re.: U.S. Appl. No. 11/798,017.
Official Action Dated Dec. 20, 2011 From the US Patent and Trademark Office Re. U.S. Appl. No. 12/309,479.
Official Action Dated Jul. 20, 2009 From the US Patent and Trademark Office Re.: U.S. Appl. No. 11/980,617.
Official Action Dated Jun. 21, 2012 From the US Patent and Trademark Office Re. U.S. Appl. No. 12/309,479.
Official Action Dated Mar. 21, 2008 From the US Patent and Trademark Office Re.: U.S. Appl. No. 10/533,568.
Official Action Dated Sep. 21, 2009 From the US Patent and Trademark Office Re. U.S. Appl. No. 11/798,017.
Official Action Dated Sep. 21, 2009 From the US Patent and Trademark Office Re.: U.S. Appl. No. 11/798,017.
Official Action Dated Apr. 23, 2012 From the US Patent and Trademark Office Re. U.S. Appl. No. 11/932,987.
Official Action Dated Dec. 23, 2008 From the US Patent and Trademark Office Re.: U.S. Appl. No. 09/727,464.
Official Action Dated Feb. 23, 2010 From the US Patent and Trademark Office Re.: U.S. Appl. No. 09/641,973.
Official Action Dated Jan. 23, 2012 From the US Patent and Trademark Office Re. U.S. Appl. No. 12/087,150.
Official Action Dated Jun. 23, 2006 From the US Patent and Trademark Office Re.: U.S. Appl. No. 09/727,464.
Official Action Dated May 23, 2011 From the US Patent and Trademark Office Re. U.S. Appl. No. 11/667,793.
Official Action Dated May 23, 2011 From the US Patent and Trademark Office Re. U.S. Appl. No. 11/980,690.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Official Action Dated Nov. 23, 2010 From the US Patent and Trademark Office Re.: U.S. Appl. No. 11/656,548.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Nov. 26, 2008 From the US Patent and Trademark Office Re.: U.S. Appl. No. 10/240,239.
Official Action Dated Oct. 26, 2011 From the US Patent and Trademark Office Re.: U.S. Appl. No. 10/836,223.
Official Action Dated Apr. 27, 2011 From the US Patent and Trademark Office Re.: U.S. Appl. No. 10/836,223.
Official Action Dated Jul. 27, 2010 From the US Patent and Trademark Office Re.: U.S. Appl. No. 10/616,307.
Official Action Dated Oct. 27, 2011 From the US Patent and Trademark Office Re.: U.S. Appl. No. 11/656,548.
Official Action Dated Apr. 28, 2010 From the US Patent and Trademark Office Re.: U.S. Appl. No. 10/616,301.
Official Action Dated Aug. 28, 2009 From the US Patent and Trademark Office Re.: U.S. Appl. No. 10/240,239.
Official Action Dated Dec. 28, 2010 From the US Patent and Trademark Office Re.: U.S. Appl. No. 11/607,075.
Official Action Dated Feb. 28, 2012 From the US Patent and Trademark Office Re.: U.S. Appl. No. 09/641,973.
Official Action Dated Jan. 28, 2011 From the US Patent and Trademark Office Re.: U.S. Appl. No. 09/641,973.
Official Action Dated Jun. 28, 2011 From the US Patent and Trademark Office Re. U.S. Appl. No. 11/628,074.
Official Action Dated Apr. 29, 2009 From the US Patent and Trademark Office Re.: U.S. Appl. No. 11/980,690.
Official Action Dated Jul. 30, 2012 From the US Patent and Trademark Office Re.: U.S. Appl. No. 11/980,683.
Official Action Dated Oct. 30, 2009 From the US Patent and Trademark Office Re.: U.S. Appl. No. 11/980,690.
Official Action Dated Sep. 30, 2008 From the US Patent and Trademark Office Re.: U.S. Appl. No. 10/616,301.
Official Action Dated Sep. 30, 2010 From the US Patent and Trademark Office Re. U.S. Appl. No. 11/798,017.
Official Action Dated Sep. 30, 2010 From the US Patent and Trademark Office Re.: U.S. Appl. No. 11/798,017.
Official Action Dated Jan. 31, 2011 From the US Patent and Trademark Office Re. U.S. Appl. No. 11/667,793.
Restriction Official Action Dated Nov. 8, 2011 From the US Patent and Trademark Office Re. U.S. Appl. No. 12/309,479.
Restriction Official Action Dated Mar. 9, 2012 From the US Patent and Trademark Office Re. U.S. Appl. No. 11/976,852.

(56) References Cited

OTHER PUBLICATIONS

Restriction Official Action Dated Sep. 12, 2011 From the US Patent and Trademark Office Re. U.S. Appl. No. 11/980,653.
Restriction Official Action Dated Apr. 13, 2012 From the US Patent and Trademark Office Re. U.S. Appl. No. 11/989,223.
Restriction Official Action Dated Nov. 15, 2011 From the US Patent and Trademark Office Re. U.S. Appl. No. 11/980,683.
Second International Search Report Dated Jun. 1, 2009 From the International Searching Authority Re.: Application No. PCT/IL07/00918.
Summons to Attend Oral Proceedings Pursuant to Rule 115(1) EPC Dated Jan. 16, 2009 From the European Patent Office Re.: Application No. 03810570.6.
Supplemental Notice of Allowability Dated Oct. 24, 2011 From the US Patent and Trademark Office Re.: U.S. Appl. No. 11/607,075.
Supplemental Response After Interview Dated Aug. 4, 2010 to Official Action of Mar. 2, 2010 From the US Patent and Trademark Office Re.: U.S. Appl. No. 11/980,617.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Supplementary European Search Report and the European Search Opinion Dated Mar. 16, 2011 From the European Patent Office Re. Application No. 05803689.8.
Supplementary European Search Report Dated Dec. 12, 2005 From the European Patent Office Re.: Application No. 03810570.6.
Supplementary Partial European Search Report and the European Search Opinion Dated Dec. 15, 2009 From the European Patent Office Re.: Application No. 06832278.3.
Supplementary Partial European Search Report and the European Search Opinion Dated Oct. 16, 2009 From the European Patent Office Re.: Application No. 06756259.5.
Supplementary Partial European Search Report Dated Sep. 4, 2007 From the European Patent Office Re.: Application No. 0 2716285.8.
Supplementary Partial European Search Report Dated Nov. 11, 2008 From the European Patent Office Re.: Application No. 01951883.6.
Supplementary Partial European Search Report Dated Nov. 20, 2007 From the European Patent Office Re.: Application No. 02716285.8.
Translation of Office Action Dated May 13, 2005 From the Patent Office of the People's Republic of China Re.: Application No. 01817689.5.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Nov. 1, 2007 from the International Searching Authority of the Patent Cooperation Treaty Re.: Application No. PCT/IL06/00840.
Written Opinion Dated Jul. 2, 2007 From the International Searching Authority of the Patent Cooperation Treaty Re.: Application No. PCT/IL2006/001291.
Written Opinion Dated Aug. 3, 2006 From the International Searching Authority of the Patent Cooperation Treaty Re.: Application No. PCT/IL05/001173.
Written Opinion Dated Oct. 10, 2006 From the International Searching Authority of the Patent Cooperation Treaty Re.: Application No. PCT/IL06/00059.
Written Opinion Dated Jul. 11, 2008 from the International Searching Authority of the Patent Cooperation Treaty Re.: Application No. PCT/IL06/01511.
Written Opinion Dated Oct. 15, 2008 From the International Searching Authority Re.: Application No. PCT/IL07/00918.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Berman et al. "Dual-Isotope Myocardial Perfusion SPECT With Rest Thallium-201 and Stress Tc-99m Sestamibi", Nuclear Cardiology, 12(2): 261-270, May 1994.
Bloch et al. "Application of Computerized Tomography to Radiation Therapy and Surgical Planning", Proceedings of the IEEE, 71(3): 351-355, Mar. 1983.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™, Product Sheet, 5 P., Jun. 1995.
Bromiley et al. "Attenuation Correction in PET Using Consistency Conditions and a Three-Dimensional Template", IEEE Transactions on Nuclear Science, 48(4): 1371-1377, 2001. p. 1376, col. 2, § 2.
Brown et al. "Method for Segmenting Chest CT Image Data Using an Anatomical Model: Preliminary Results", IEEE Transactions on Medical Imaging, 16(6): 828-839, Dec. 1997.
Chengazi et al. "Imaging Prostate Cancer With Technetium-99m-7E11-C5.3 (CYT-351)", Journal of Nuclear Medicine, 38: 675-682, 1997.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
DeGrado et al. "Topics in Integrated Systems Physiology. Tracer Kinetic Modeling in Nuclear Cardiology", Journal of Nuclear Cardiology, 7: 686-700, 2000.
Del Guerra et al. "An Integrated PET-SPECT Small Animal Imager: Preliminary Results", Nuclear Science Symposium, IEEE Records, 1: 541-544, 1999.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
Ellestad "Stress Testing: Principles and Practice", XP008143015, 5th Edition, p. 432, Jan. 1, 2003.
Erbil et al. "Use and Limitations of Serum Total and Lipid-Bound Sialic Acid Concentrations as Markers for Colorectal Cancer", Cancer, 55: 404-409, 1985.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Gilland et al. "A 3D Model of Non-Uniform Attenuation and Detector Response for Efficient Iterative Reconstruction in SPECT", Physics in Medicine and Biology, 39(3):547-561, Mar. 1994. p. 549-550, Section 2.3 'Active Voxel Reconstruction', p. 551, Lines 4-8.
Gilland et al. "Long Focal Length, Asymmetric Fan Beam Collimation for Transmission Acquisition With a Triple Camera SPECT System", IEEE Transactions on Nuclear Science, 44(3): 1191-1196, Jun. 1, 1997.

(56) References Cited

OTHER PUBLICATIONS

Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.

Gugnin et al "Radiocapsule for Recording the Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).

Handrick et al. "Evaluation of Binning Strategies for Tissue Classification in Computed Tomography Images", Medical Imaging 2006: Image Processing, Proceedings of the SPIE, 6144: 1476-1486, 2006.

Hassan et al. "A Radiotelemetry Pill for the Measurement of Ionising Radiation Using a Mercuric Iodide Detector", Physics in Medicine and Biology, 23(2): 302-308, 1978.

Hayakawa et al. "A PET-MRI Registration Technique for PET Studies of the Rat Brain", Nuclear Medicine & Biology, 27: 121-125, 2000. p. 121, col. 1.

Herrmann et al. "Mitochondrial Proteome: Altered Cytochtrome C Oxidase Subunit Levels in Prostate Cancer", Proteomics, 3(9): 1801-1810, Sep. 2003.

Hoffman et al. "Intraoperative Probes and Imaging Probes", European Journal of Nuclear Medicine, 26(8): 913-935, 1999.

Huesman et al. "Kinetic Parameter Estimation From SPECT Cone-Beam Projection Measurements", Physics in Medicine and Biology, 43(4): 973-982, 1998.

Jeanguillaume et al. "From the Whole-Body Counting to Imaging: The Computer Aided Collimation Gamma Camera Project (CACAO)", Radiation Projection Dosimetry, 89(3-4): 349-352, 2000. & RSNA 2000 Infosystem, 87th Scientific Assembly and Annual Meeting, Chicago, Illinois, 2000.

Jessup "Tumor Markers—Prognostic and Therapeutic Implications for Colorectal Carcinoma", Surgical Oncology, 7: 139-151, 1998.

Jin et al. "Reconstruction of Cardiac-Gated Dynamic SPECT Images", IEEE International Conference on Image Processing 2005, ICIP 2005, Sep. 11-14, 2005, 3: 1-4, 2005.

Kadrmas et al. "Static Versus Dynamic Teboroxime Myocardial Perfusion SPECT in Canines", IEEE Transactions on Nuclear Science, 47(3): 1112-1117, Jun. 2000.

Kinahan et al. "Attenuation Correction for a Combined 3D PET/CT Scanner", Medical Physics, 25(10): 2046-2053, Oct. 1998.

Kojima et al. "Quantitative Planar Imaging Method for Measurement of Renal Activity by Using a Conjugate Emission Image and Transmission Data", Medical Physics, 27(3): 608-615, 2000. p. 608.

Krieg et al. "Mitochondrial Proteome: Cancer-Altered Metabolism Associated With Cytochrome C Oxidase Subunit Level Variation", Proteomics, 4(9): 2789-2795, Sep. 2004.

Lavallee et al. "Building a Hybrid Patient's Model for Augmented Reality in Surgery: A Registration Problem", Computing in Biological Medicine, 25(2): 149-164, 1995.

Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, 2: 1135-1139, Nov. 10, 2002. p. 1137, First col., 2nd §.

Lin et al. "Improved Sensor Pills for Physiological Monitoring", NASA Technical Brief, JPL New Technology Report, NPO-20652, 25(2), 2000.

Links "Advances in SPECT and PET Imaging", Annals in Nuclear Medical Science, 13(2): 107-120, Jun. 2000.

Mallinckrodt "Kit for the Preparation of Technetium Tc 99m Sestamibi Injection", Mallinckrodt Inc., Product Sheet, 2 P., Sep. 8, 2008.

Mallinckrodt "OctreoScan®: Kit for the Preparation of Indium In-111 Pentetreotide. Diagnostic—for Intravenous Use. Rx Only", Mallinckrodt Inc., Product Sheet, 2 P., Oct. 25, 2006.

Mao et al. "Human Prostatic Carcinoma: An Electron Microscope Study", Cancer Research, 26(5): 955-973, May 1966.

McJilton et al. "Protein Kinase C? Interacts With Bax and Promotes Survival of Human Prostate Cancer Cells", Oncogene, 22; 7958-7968, 2003.

Mettler et al. "Legal Requirements and Radiation Safety", Essentials of Nuclear Medicine Imaging, 2nd Ed., Chap.13: 323-331, 1985.

Meyers et al. "Age, Perfusion Test Results and Dipyridamole Reaction", Radiologic Technology, 73(5): 409-414, May 1, 2002.

Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.

Moore et al. "Quantitative Multi-Detector Emission Computerized Tomography Using Iterative Attenuation Compensation", Journal of Nuclear Medicine, 23(8): 706 714, Aug. 1982. Abstract, p. 707, Section 'The Multi Detector Scanner', First §.

Mori et al. "Overexpression of Matrix Metalloproteinase-7mRNA in Human Colon Carcinomas", Cancer, 75: 1516-1519, 1995.

Ogawa et al. "Ultra High Resoultion Pinhole SPECT", IEEE Nuclear Science Symposium, 2: 1600-1604, 1998.

Pardridge et al. "Tracer Kinetic Model of Blood-Brain Barrier Transport of Plasma Protein-Bound Ligands", Journal of Clinical Investigation, 74: 745-752, 1984.

Pellegrini et al. "Design of Compact Pinhole SPECT System Based on Flat Panel PMT", IEEE Nuclear Science Symposium Conference Record, 3: 1828-1832, 2003.

Pharmalucence "Kit for the Preparation of Technetium Tc99m Sulfur Colloid Injection for Subcutaneous, Intraperitoncal, Intravenous, and Oral Use", Pharmalucence Inc., Reference ID: 2977567, Prescribing Information, 10 P., Jul. 2011.

Piperno et al. "Breast Cancer Screening by Impedance Measurements", Frontiers Med. Biol. Engng., 2(2): 11-17, 1990.

Pluim et al. "Image Registration by Maximization of Combined Mutual Information and Gradient Information", IEEE Transactions on Medical Imaging, 19(8): 1-6, 2000.

Qi et al. "Resolution and Noise Properties of MAP Reconstruction for Fully 3-D PET", IEEE Transactions on Medical Imaging, 19(5): 493-506, May 2000. p. 493, col. 2, Lines 10-21, p. 495, col. 1, Last §.

Quartuccia et al. "Computer Assisted Collimation Gama Camera: A New Approach to Imaging Contaminated Tissues", Radiation Projection Dosimetry, 89(3-4): 343-348, 2000.

Rajshekhar "Continuous Impedence Monitoring During CT-Guided Stereotactic Surgery: Relative Value in Cystic and Solid Lesions", British Journal of Neurosurgery, 6: 439-444, 1992.

Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.

Reutter et al. "Kinetic Parameter Estimation From Attenuated SPECT Projection Measurements", IEEE Transactions on Nuclear Science, 45(6): 3007-3013, 1998.

Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.

Stoddart et al. "New Multi-Dimensional Reconstructions for the 12-Detector, Scanned Focal Point, Single-Photon Tomograph", Physics in Medicine and Biology, 37(3): 579-586, Mar. 1, 1992. p. 582, § 2-p. 585, § 1.

Storey et al. "Tc-99m Sestamibi Uptake in Metastatic Prostate Carcinoma", Clinical Nuclear Medicine, 25(2): 133-134, Feb. 2000.

Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.

Thorndyke et al. "Reducing Respiratory Motion Artifacts in Positron Emission Tomography Through Retrospective Stacking", Medical Physics, 33(7): 2632-2641, Jul. 2006.

Toennies et al. "Scatter Segmentation in Dynamic SPECT Images Using Principal Component Analysis", Progress in Biomedical Optics and Imaging, 4(23): 507-516, 2003.

(56) References Cited

OTHER PUBLICATIONS

Trikha et al. "Monoclonal Antibodies as Therapeutics in Oncology", Current Opinion in Biotechnology, 13: 609-614, 2002.
Volkow et al. "Imaging the Living Human Brain: Magnetic Resonance Imaging and Positron Emission Tomography", Proc. Natl. Acad. Sci. USA, 94: 2787-2788, Apr. 1997.
Wilson et al. "Non-Stationary Noise Characteristics for SPECT Images", Proceedings of the Nuclear Science Symposium and Medical Imaging Conference, Santa Fe, CA, USA, Nov. 2-9, 1991, p. 1736-1740, Nov. 2, 1991. p. 1736, col. 2, Lines 4-6.
Wu et al. "ECG-Gated Pinhole SPECT in Mice With Millimeter Spatial Resolution", IEEE Transactions on Nuclear Science, 47(3): 1218-1221, Jun. 2000.
Xu et al. "Quantitative Expression Profile of Androgen-Regulated Genes in Prostate Cancer Cells and Identification of Prostate-Specific Genes", International Journal of Cancer, 92: 322-328, 2001.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Zhang et al. "An Innovative High Efficiency and High Resolution Probe for Prostate Imaging", The Journal of Nuclear Medicine, 68: 18, 2000. Abstract.
Zhang et al. "Potential of a Compton Camera for High Performance Scintimammography", Physics in Medicine and Biology, 49(4): 617-638, Feb. 21, 2004.
Notice of Allowance Dated Oct. 26, 2012 From the US Patent and Trademark Office Re. U.S. Appl. No. 12/514,785.
Official Action Dated Nov. 30, 2012 From the US Patent and Trademark Office Re. U.S. Appl. No. 12/514,785.
Supplementary European Search Report and the European Search Opinion Dated Nov. 13, 2012 From the European Patent Office Re. Application No. 06728347.3.
Summons to Attend Oral Proceedings Pursuant to Rule 115(1) EPC Dated Nov. 29, 2012 From the European Patent Office Re. Application No. 06756259.5.
Communication Pursuant to Article 94(3) EPC Dated Nov. 12, 2012 From the European Patent Office Re. Application No. 06756258.7.
Notice of Allowance Dated Nov. 15, 2012 From the US Patent and Trademark Office Re.: U.S. Appl. No. 11/980,683.
RJ Ott, "Imaging technologies for radionuclide dosimetry," Phys. Med. Biol. 41: 1885-1894 (1996).
G Sgouros et al., "Patient-Specific, 3-Dimensional Dosimetry in Non-Hodgkin's Lymphoma Patients Treated with 131I-anti-B1 Antibody: Assessment of Tumor Dose-Response," Journal of Nuclear Medicine vol. 44 No. 2 260-268 (2003).
G Sgouros et al., "Patient-Specific Dosimetry for 131I Thyroid Cancer Therapy Using 124I PET and 3-Dimensional-Internal Dosimetry (3D-ID) Software," Journal of Nuclear Medicine vol. 45 No. 8:1366-1372 (2004).
Notice of Allowance Dated Jul. 19, 2013 From the US Patent and Trademark Office Re. U.S. Appl. No. 11/989,223.
Notice of Allowance Dated Jul. 25, 2013 From the US Patent and Trademark Office Re. U.S. Appl. No. 13/345,719.
Official Action Dated Jul. 30, 2013 From the US Patent and Trademark Office Re. U.S. Appl. No. 10/343,792.
Official Action Dated Jul. 31, 2013 From the US Patent and Trademark Office Re. U.S. Appl. No. 11/667,793.
Supplemental Notice of Allowability Dated Aug. 12, 2014 From the US Patent and Trademark Office Re. U.S. Appl. No. 13/345,773.

\* cited by examiner

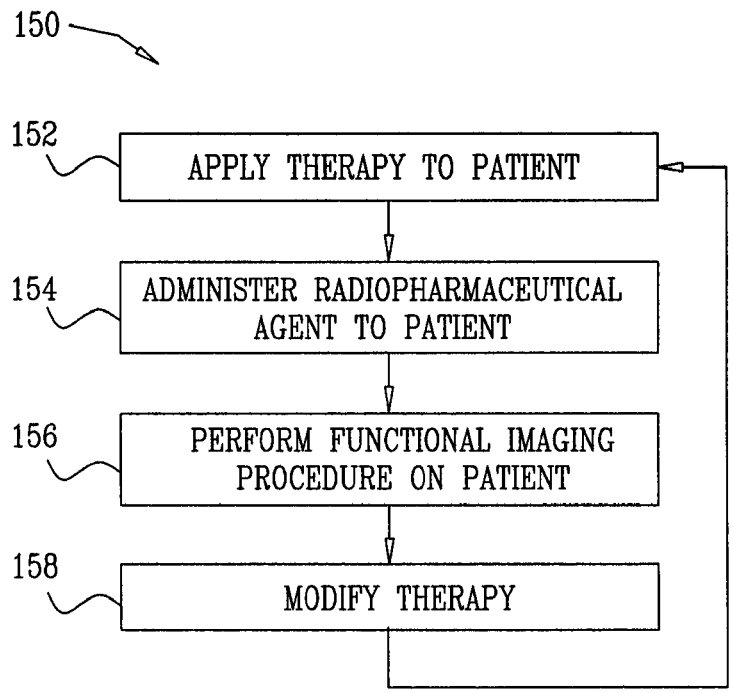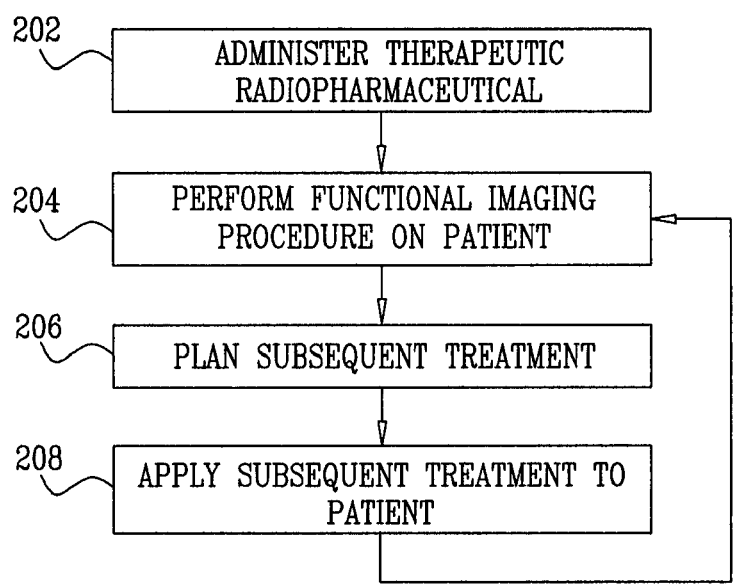

RADIOPHARMACEUTICALS FOR DIAGNOSIS AND THERAPY

CROSS-REFERENCES TO RELATED APPLICATIONS

The present application claims the benefit of U.S. Provisional Application 60/799,688, filed May 11, 2006, entitled, "Imaging protocols," which is incorporated herein by reference.

FIELD OF THE INVENTION

The present invention relates generally to radiological imaging techniques, and specifically to apparatus and methods for optimizing therapy using imaging procedures.

BACKGROUND OF THE INVENTION

PCT Publication WO 06/051531 to Rousso et al., which is assigned to the assignee of the present application and is incorporated herein by reference, describes radioimaging methods, devices and radiopharmaceuticals.

U.S. Pat. No. 6,242,743 to DeVito et al., which is incorporated herein by reference, describes a tomographic imaging system which images ionizing radiation such as gamma rays or x rays. The system is described as being capable of producing tomographic images without requiring an orbiting motion of the detector(s) or collimator(s) around the object of interest, and of observing the object of interest from sufficiently many directions to allow multiple time-sequenced tomographic images to be produced. The system consists of a plurality of detector modules which are distributed about or around the object of interest and which fully or partially encircle it. The detector modules are positioned close to the object of interest thereby improving spatial resolution and image quality. The plurality of detectors view a portion of the patient or object of interest simultaneously from a plurality of positions. These attributes are achieved by configuring small modular radiation detector with high-resolution collimators in a combination of application-specific acquisition geometries and non-orbital detector module motion sequences composed of tilting, swiveling and translating motions, and combinations of such motions. Various kinds of module geometry and module or collimator motion sequences are possible. The geometric configurations may be fixed or variable during the acquisition or between acquisition intervals.

The Bexxar® (GlaxoSmithKline) therapeutic regimen (Tositumomab and Iodine I-131 Tositumomab) is indicated for the treatment of patients with CD20 antigen-expressing relapsed or refractory, low-grade, follicular, or transformed non-Hodgkin's lymphoma, including patients with Rituximab-refractory non-Hodgkin's lymphoma. The Bexxar therapeutic regimen is delivered in two sets of intravenous infusions given 7-14 days apart. A trace amount of radioactive Iodine-131 tositumomab, is initially given to enable evaluation of the clearance of radiation from the patient's body with gamma camera scans. A therapeutic dose, which is given 7-14 days after the dosimetric infusion, is tailored for each patient based on the patient's individualized radiation clearance rates. The therapeutic dose contains tositumomab labeled with the amount of I-131 tositumomab specifically calculated for the patient based on the scans performed following the dosimetric dose.

Following the infusion of the dosimetric dose, counts are taken with a gamma camera to track the elimination of radiation from the body. The patient then returns to the hospital for two more scans, approximately two days apart. These procedures are important because highly individual factors such as tumor size, bone marrow involvement, and spleen size affect how long the radiation remains in the body. Dosimetry, therefore, allows the amount of I-131 radiation administered in the therapeutic dose to be adjusted for each patient so that the optimal target dose of radiation is achieved for maximum effectiveness while minimizing toxicities.

U.S. Pat. No. 6,287,537 to Kaminski et al., which is incorporated herein by reference, describes methods for the treatment of lymphoma by administration of a B cell-specific antibody. The invention includes providing to a patient both unlabeled antibodies and antibodies labeled with a radioisotope. A principal advantage of the method is that tumor responses can be obtained in a radiometric dose range that does not require hematopoietic stem cell replacement as an adjunct therapy. One method described for using B1 antibody includes administering a trace-labeled amount of B1 antibody, followed by imaging of the distribution of the B1 antibody in the patient. After imaging, a therapeutic regime of radiolabeled B1 is administered, designed to deliver a radiometric dose of 25 to 500 cGy, preferably 25 to 150 cGy, to the whole body of the patient.

Van Den Bossche B et al., in "Receptor imaging in oncology by means of nuclear medicine: current status," Journal of Clinical Oncology 22(17):3593-3607 (2004), review available data on the in vivo evaluation of receptor systems by means of PET or SPECT for identifying and monitoring patients with sufficient receptor overexpression for tailored therapeutic interventions, and also for depicting tumor tissue and determining the currently largely unknown heterogeneity in receptor expression among different tumor lesions within and between patients. PET can be used to image and quantify the in vivo distribution of positron-emitting radioisotopes such as oxygen-15, carbon-11, and fluorine-18 that can be substituted or added into biologically relevant and specific receptor radioligands. Similarly, SPECT can be used to image and quantify the in vivo distribution of receptor targeting compounds labeled with indium-111, technetium-99m, and iodine-123. By virtue of their whole-body imaging capacity and the absence of errors of sampling and tissue manipulation as well as preparation, both techniques have the potential to address locoregional receptor status noninvasively and repetitively.

The following patents and patent application publications, which describe gamma cameras and imaging processing techniques, and which are incorporated herein by reference, may be of interest:

US Patent Application Publication 2005/0205792 to Rousso et al.

PCT Publication WO 05/118659 to Dicbterman et al.

PCT Publication WO 05/119025 to Nagler et al.

US Patent Application Publication 2004/0204646 to Nagler et al.

PCT Publication WO 06/054296 to Dickman

PCT Publication WO 04/042546 to Kimchy et al.

US Patent Application Publication 2004/0054248 to Kimchy et al.

US Patent Application Publication 2004/0015075 to Kimchy et al.

US Patent Application Publication 2004/0054278 to Kimchy et al.

US Patent Application Publication 2005/0266074 to Zilberstein et al.

U.S. Pat. Nos. 5,939,724, 5,587,585, and 5,365,069 to Eisen et al.

U.S. Pat. No. 6,943,355 to Shwartz et al.

U.S. Pat. No. 5,757,006 to DeVito et al.
U.S. Pat. No. 6,137,109 to Hayes
U.S. Pat. No. 6,398,258 to Berlad et al.
U.S. Pat. No. 6,429,431 to Wilk
U.S. Pat. No. 6,838,672 to Wagenaar et al.
U.S. Pat. Nos. 6,740,882, 6,545,280, 6,229,145, 5,519,221, 5,252,830, and 6,628,984 to Weinberg
U.S. Pat. No. 6,713,766 to Garrard et al.
U.S. Pat. No. 6,765,981 to Heumann
U.S. Pat. No. 6,664,542 to Ye et al.
U.S. Pat. No. 6,080,984 to Friesenhahn
U.S. Pat. No. 5,818,050 to Dilmanian et al.
U.S. Pat. No. 6,728,583 to Hallett
U.S. Pat. No. 5,481,115 to Hsieh et al.
U.S. Pat. No. 6,723,988 to Wainer
U.S. Pat. No. 6,940,070 to Tumer
U.S. Pat. No. 6,635,879 to Jimbo et al.
U.S. Pat. No. 6,353,227 to Boxen
U.S. Pat. No. 6,184,530 to Hines et al.
US Patent Application Publication 2005/0145797 to Oaknin et al.
US Patent Application Publication 2004/0251419 to Nelson et al.
US Patent Application Publication 2003/0001098 to Stoddart et al.
PCT Publication WO 98/16852 to DeVito et al.
PCT Publication WO 05/059840 to Nielsen et al.
U.S. Pat. No. 5,813,985 to Carroll
U.S. Pat. No. 6,455,043 to Grillo-Lopez The following articles, all of which are incorporated herein by reference, may be of interest:

Yao D et al., "The utility of monoclonal antibodies in the imaging of prostate cancer," Semin Urol Oncol 20(3):211-8 (2002)

van der Laken C J et al., "Technetium-99m-labeled chemotactic peptides in acute infection and sterile inflammation," J Nucl Med 38(8):1310-5 (1997)

Babich J W et al., "Localization of radiolabeled chemotactic peptide at focal sites of *Escherichia coli* infection in rabbits: evidence for a receptor-specific mechanism," J Nucl Med 38(8):1316-22 (1997)

Rao P S et al., "99mTc-peptide-peptide nucleic acid probes for imaging oncogene mRNAs in tumours," Nuclear Medicine Communications 24(8):857-863 (2003)

Fischman A J et al., "Infection imaging with technetium-99m-labeled chemotactic peptide analogs," Semin Nucl Med 24(2):154-68 (1994)

Massoud T F et al., "Molecular imaging in living subjects: seeing fundamental biological processes in a new light," Genes & Development 17:545-580 (2003)

Gambhir S. S, "Molecular imaging of cancer with positron emission tomography," Nature Reviews 2:683-693 (2002).

SUMMARY OF THE INVENTION

In some embodiments of the present invention, the results of one or more radioimaging procedures, such as SPECT or PET imaging procedures, are used to optimize a treatment, a diagnosis, and/or a patient management decision.

In some embodiments of the present invention, a method for optimizing treatment of a patient includes administering a radiolabeled therapeutic agent, typically at a low dose. The radiolabeled therapeutic drug typically comprises a therapeutic drug otherwise known in the art, which is radiolabeled, such as by using techniques of embodiments of the present invention. The known, non-radiolabeled form of the therapeutic agent is typically substantially non-radioactive. A functional imaging procedure, e.g., a SPECT or PET imaging procedure, is performed to acquire information regarding the activity of the therapeutic agent. The information is used to customize (i.e., personalize) a subsequent treatment of the patient. For some applications, customizing the subsequent treatment comprises determining a subsequent, therapeutic dose of the same therapeutic agent administered for the functional imaging procedure. Determining the subsequent dose typically comprises setting the dose at a level that limits the likelihood of serious adverse events (SAEs) or the toxicity of the subsequent administration of the therapeutic agent, and/or generally maximizes an effectiveness of the subsequent administration of the therapeutic agent.

The use of this technique thus enables treatment to be customized (i.e., personalized) per individual patient, rather than relying on textbook curves of bioavailability applicable to large patient populations. This technique may be particularly beneficial for therapeutic agents for which it is difficult to pre-identify responders and non-responders, or to predict side effects. Furthermore, a number of drugs suffer from lack of specificity because they do not sufficiently distinguish target cells from non-target cells when applied to an entire patient population. Customization of the dose of such drugs for a particular patient enables the drugs to sufficiently distinguish target cells from non-target cells. Using these techniques, a precise dose of the drug is determined for the specific patient, which dose is high enough to be therapeutically effective in the specific patient (optionally, even higher than the approved dosage and regimen), but low enough to avoid SAEs, side effects, and toxicity for the specific patient. These techniques also enable earlier cessation of administration of a drug if it is not efficacious in a specific patient. Alternatively or additionally, these techniques are used during drug discovery and/or development processes (for example, in vivo or in human first clinical trials to select which compounds to take to the next development stages), a regulatory approval process, or thereafter to determine recommended doses for segments of a population upon which the drug has differing effects.

For some applications, the first, low dose of the radiolabeled therapeutic agent is less than 10% of a conventional therapeutic dose of the therapeutic agent, or of the therapeutic dose used during the subsequent administration, such as less than 5%, less than 2%, less than 1%, less than 0.5%, less than 0.1%, less than 0.05%, or less than 0.01% of the conventional dose or the dose used during the subsequent administration. For some applications, the radiolabeled therapeutic agent binds to a biological target in the body of the patient having a Molar concentration of less than $10^{-10}$, such as less than $10^{-11}$ or less than $10^{-12}$. A "Molar concentration," as used in the present application, including in the claims, means moles per liter of solution.

In some embodiments of the present invention, a method for treating a patient comprises applying a therapy to the patient (either a drug therapy or a non-drug therapy; if a drug therapy, the drug may or may not comprise a radiopharmaceutical). A radiopharmaceutical imaging agent is administered to the patient, and a functional imaging procedure, such as a SPECT or PET imaging procedure, is performed on the patient to measure a property indicative of biochemical activity of the therapy in at least one tissue of the patient, such as a property indicative of bioavailability of the drug if the therapy comprises a drug therapy. Responsively to the measured biochemical activity, a parameter of the therapy is modified, and the therapy is again applied with the modified parameter. The parameter of the therapy is typically modified to optimize the therapy, such as by modifying a dose or regimen of the therapy, and/or to customize (i.e., personalize) the therapy for the patient, either on a long- or short-term basis. For some applications, these techniques are used to monitor: (a) a therapeutic effect of a therapy (e.g., an anti-inflammatory agent an antibiotic agent, or a chemotherapy agent) on target cells, tissue, or an organ, and/or (b) an undesired effect of the therapy on non-target cells, tissue, or organs.

For some applications, these techniques for determining the efficacy of a therapy are used instead of or in addition to conventional imaging techniques, such as CT or MRS. The functional information provided by the SPECT or PET imaging procedures provides information not provided by such conventional imaging techniques. For example, when determining the efficacy of treatment of a tumor, such functional information enables a more accurate determination to be made regarding whether the tumor is alive, and/or the precise location of the tumor, than is possible by simply determining the tumor's size or general location.

There is therefore provided, in accordance with an embodiment of the present invention, a method for treating a human patient, including:

administering a radiolabeled form of a therapeutic agent to the patient at a first substantially non-therapeutically-effective dose, wherein pharmacological activity of the therapeutic agent is not due to radioactivity of the therapeutic agent;

determining information related to a biodistribution of the radiolabeled form of the therapeutic agent in the patient by performing a radioimaging procedure on the patient;

responsively to the information, making a decision whether or not to treat the patient by administering the therapeutic agent to the patient;

if the decision is made to treat the patient, treating the patient by administering the therapeutic agent to the patient at a second therapeutically-effective dose; and if the decision is made not to treat the patient, withholding treating the patient with the therapeutic agent.

For some applications, making the decision includes making the decision responsively to a likelihood of an occurrence of an adverse advent caused by the therapeutic agent, determined responsively to the information. Alternatively or additionally, making the decision includes making the decision responsively to a likelihood of treatment success by administering the therapeutic agent, determined responsively to the information. Further alternatively or additionally, making the decision includes making the decision responsively to a determination, made responsively to the information, of whether the patient is likely to be a responder to treatment with the therapeutic agent.

In an embodiment, treating the patient includes treating the patient by administering a non-radiolabeled form of the therapeutic agent to the patient at the second dose, which non-radiolabeled form of the therapeutic agent is substantially non-radioactive. Alternatively, treating the patient includes treating the patient by administering the radiolabeled form of the therapeutic agent to the patient at the second dose.

In an embodiment, treating the patient includes setting the second therapeutically-effective dose of the therapeutic agent responsively to the information. For some applications, setting the second dose includes setting the second dose at a level that reduces a likelihood of an occurrence of an adverse advent caused by the administering the therapeutic agent, determined responsively to the information.

In an embodiment, the first dose has a total radioactivity per body mass of the patient that is less than 0.05 mCi/kg.

In an embodiment, the first dose is less than the second dose. For example, the first dose may be less than 10% of the second dose, less than 2% of the second dose, less than 1% of the second dose, less than 0.5% of the second dose, or less than 0.1% of the second dose.

In an embodiment the radiolabeled form of the therapeutic agent binds to a biological target in a body of the patient having a Molar concentration of less than $10^{-10}$, such as less: than $10^{-11}$.

In an embodiment, administering the radiolabeled form of the therapeutic agent includes administering the radiolabeled form formed by replacing a non-radioactive isotope of an element of a non-radiolabeled form of the therapeutic agent with a radioactive isotope. For example, the radioactive isotope may be selected from the group consisting of: iodine-131, iodine-123, In-111, and Ga-67. Alternatively administering the radiolabeled form of the therapeutic agent includes administering the radiolabeled form formed by bonding a radioactive radiotracer to the non-radiolabeled form of the therapeutic agent.

In an embodiment, the therapeutic agent is selected from the group consisting of: a protein, an analgesic, an antibiotic, a cardiac drug, a neurological drug, an anti-inflammatory agent, and a non-steroidal anti-inflammatory agent.

In an embodiment, performing the radioimaging procedure includes performing a functional radioimaging procedure on the patient. For some applications, performing the functional radioimaging procedure includes performing a SPECT imaging procedure on the patient. For some applications, performing the SPECT imaging procedure includes performing the SPECT imaging procedure using a high-definition SPECT camera.

For some applications, determining the information includes determining the information related to a time profile of at least a portion of the biodistribution of the radiolabeled form of the therapeutic agent. Alternatively or additionally, determining the information includes determining the information related to an uptake of the radiolabeled form of the therapeutic agent. Further alternatively or additionally, determining the information includes determining the information related to metabolism of at least one element selected from the group consisting of: the radiolabeled form of the therapeutic agent, a substrate of the radiolabeled form of the therapeutic agent, and an enzyme involved in metabolism of the radiolabeled form of the therapeutic agent.

In an embodiment, administering the radiolabeled form of the therapeutic agent includes administering respective radiolabeled forms of a plurality of therapeutic agents to the patient at respective first substantially non-therapeutically-effective doses, wherein the pharmacological activity of the therapeutic agents is not due to radioactivity of the therapeutic agents, determining the information includes determining the information related to respective biodistributions of the radiolabeled forms of the therapeutic agents in the patient by performing the radioimaging procedure on the patient, making the decision includes making the decision, responsively to the information, whether or not to treat the patient by administering one or more of the plurality of therapeutic agents to the patient, and if the decision is made to treat the patient, treating the patient by administering the one or more of the plurality of therapeutic agents to the patient at respective second therapeutically-effective doses.

For some applications, if the decision is made to treat the patient, treating the patient by administering the one or more of the plurality of therapeutic agents includes withholding administering at least one other of the plurality of therapeutic agents.

For some applications, making the decision includes making the decision to treat the patient by administering the one or more of the plurality of therapeutic agents responsively to a determination that the one or more of the plurality of therapeutic agents are more likely to be effective in treating the patient than at least one other of the plurality of therapeutic agents.

For some applications, two or more of the radiolabeled forms of plurality of therapeutic agents are radiolabeled with a same radiotracer. Alternatively or additionally, two or more of the radiolabeled forms of plurality of therapeutic agents are radiolabeled with different radiotracers.

For some applications, the plurality of therapeutic agents include at least five therapeutic agents, such as at least ten therapeutic agents.

There is further provided, in accordance with an embodiment of the present invention, a method for treating a human patient, including:

administering a radiolabeled form of a therapeutic agent to the patient at a first dose, wherein pharmacological activity of the therapeutic agent is not due to radioactivity of the therapeutic agent;

determining information related to a biodistribution of the radiolabeled form of the therapeutic agent in the patient by performing a radioimaging procedure on the patient responsively to the information, setting a second therapeutically-effective dose of the therapeutic agent; and treating the patient by administering the therapeutic agent to the patient at the second dose.

In an embodiment, the first dose is substantially not therapeutically effective, and administering the radiolabeled form of the therapeutic agent includes administering the radiolabeled form of the therapeutic agent at the substantially non-therapeutically-effective fist dose.

In an embodiment, treating the patient by administering the therapeutic agent includes treating the patient by administering a non-radiolabeled form of the therapeutic agent to the patient at the second dose, which non-radiolabeled form of the therapeutic agent is substantially non-radioactive. Alternatively, treating the patient by administering the therapeutic agent includes treating the patient by administering the radiolabeled form of the therapeutic agent to the patient at the second dose.

In an embodiment, setting the second dose includes setting the second dose at a level that reduces a likelihood of an adverse advent caused by the administering the therapeutic agent, determined responsively to the information.

In an embodiment the first dose has a total radioactivity per body mass of the patient that is less than 0.05 mCi/kg.

In an embodiment, the first dose is less than the second dose. For example, the first dose may be less than 10% of the second dose, less than 2% of the second dose, less than 1% of the second dose, less than 0.5% of the second dose, or less than 0.1% of the second dose.

In an embodiment, the radiolabeled form of the therapeutic agent binds to a biological target in a body of the patient having a Molar concentration of less than $10^{-10}$, such as less than $10^{-11}$.

In an embodiment, administering the radiolabeled form of the therapeutic agent includes administering the radiolabeled form formed by replacing a non-radioactive isotope of an element of a non-radiolabeled form of the therapeutic agent with a radioactive isotope. For example, the radioactive isotope may be selected from the group consisting of: iodine-131, iodine-123, In-111, and Ga-67. Alternatively, administering the radiolabeled form of the therapeutic agent includes administering the radiolabeled form formed by bonding a radioactive radiotracer to the non-radiolabeled form of the therapeutic agent.

In an embodiment, the therapeutic agent is selected from the group consisting of: a protein, an analgesic, an antibiotic, a cardiac drug, a neurological drug, an anti-inflammatory agent, and a non-steroidal anti-inflammatory agent.

In an embodiment, performing the radioimaging procedure includes performing a functional radioimaging procedure on the patient. For some applications, performing the functional radioimaging procedure includes performing a SPECT imaging procedure on the patient. For some applications, performing the SPECT imaging procedure includes performing the SPECT imaging procedure using a high-definition SPECT camera.

For some applications, determining the information includes determining the information related to a time profile of at least a portion of the biodistribution of the radiolabeled form of the therapeutic agent. Alternatively or additionally, determining the information includes determining the information related to an uptake of the radiolabeled form of the therapeutic agent. Further alternatively or additionally, determining the information includes determining the information related to metabolism of at least one element selected from the group consisting of: the radiolabeled form of the therapeutic agent, a substrate of the radiolabeled form of the therapeutic agent, and an enzyme involved in metabolism of the radiolabeled form of the therapeutic agent.

There is still further provided, in accordance with an embodiment of the present invention, a method including:

providing a radiolabeled form of a therapeutic agent that binds to a biological target in a body of a human patient having a Molar concentration of less than $10^{-10}$;

administering the radiolabeled form of the therapeutic agent to the patient at a non-therapeutic dose; and performing a radioimaging procedure on the patient in conjunction with the administering (i.e., during and/or after the administering).

In an embodiment, pharmacological activity of the therapeutic agent is not due to radioactivity of the therapeutic agent.

For some applications, the biological target has a Molar concentration of less than $10^{-11}$, such as less than $10^{-12}$.

In an embodiment, administering the radiolabeled form of the therapeutic agent includes administering the radiolabeled form of the therapeutic agent having a total radioactivity per body mass of the patient that is less than 0.05 mCi/kg. For some applications, the biological target is selected from the group consisting of: a protein of the patient, and an mRNA of the patient.

In an embodiment, providing the radiolabeled form of the therapeutic agent includes replacing a non-radioactive isotope of an element of a non-radiolabeled form of the therapeutic agent with a radioactive isotope. For example, the radioactive isotope may be selected from the group consisting of: iodine-131, iodine-123, In-111, and Ga-67. Alternatively, providing the radiolabeled form of the therapeutic agent includes bonding a radioactive radiotracer to a non-radiolabeled form of the therapeutic agent.

In an embodiment, the therapeutic agent is selected from the group consisting of: a protein, an analgesic, an antibiotic, a cardiac drug, a neurological drug, an anti-inflammatory agent, and a non-steroidal anti-inflammatory agent.

In an embodiment, performing the radioimaging procedure includes performing a functional radioimaging procedure on die patient. For some applications, performing the functional radioimaging procedure includes performing a SPECT imaging procedure on the patient. For some applications, performing the SPECT imaging procedure includes performing the SPECT imaging procedure using a high-definition SPECT camera.

There is additionally provided, in accordance with an embodiment of the present invention, a method for treating a human patient, including:

applying a therapy to the patient;

administering a radiopharmaceutical agent to the patient;

performing a functional imaging procedure on the patient to measure a property indicative of biochemical activity of the therapy in at least one tissue of the patient; and modifying at least one parameter of the therapy responsively to the measured biochemical activity.

In an embodiment, the radiopharmaceutical agent includes a radiolabeled form of a therapeutic agent, wherein pharmacological activity of the therapeutic agent is not due to radioactivity of the therapeutic agent, and administering the radiopharmaceutical agent includes administering the radiolabeled form of the therapeutic agent.

In an embodiment applying the therapy includes applying a non-drug therapy to the patient.

In an embodiment, applying the therapy includes administering a drug to the patient. For some applications, performing the functional imaging procedure includes measuring a property indicative of bioavailability of the drug in the at least one tissue. For some applications, the drug is selected from the group consisting of: a protein, an analgesic, an antibiotic, a cardiac drug, a neurological drug, an anti-inflammatory agent, and a non-steroidal anti-inflammatory agent. For some applications, administering the drug includes administering a plurality of drugs at respective doses, and modifying the at least one parameter of the therapy includes modifying the respective doses.

In an embodiment, moping the at least one parameter includes ceasing to apply the therapy responsively to the measured biochemical activity. For some applications, the at least one parameter includes at least one parameter selected from the group consisting of: a dose of the therapy, a regimen of the therapy, and a timing parameter of the therapy.

For some applications, the measured biochemical activity is indicative of a therapeutic effect of the therapy, and performing the functional imaging procedure includes measuring the property indicative of the therapeutic effect. Alternatively or additionally, the measured biochemical activity is indicative of a undesired effect of the therapy, and performing the functional imaging procedure includes measuring the property indicative of the undesired effect.

For some applications, applying the therapy includes applying the therapy before administering the radiopharmaceutical agent, and applying the therapy after modifying the at least one parameter of the therapy.

For some applications, performing the functional imaging procedure includes performing the functional imaging procedure while applying, the therapy to the patient.

For some applications, administering the radiopharmaceutical agent and performing the functional imaging procedure include administering the radiopharmaceutical agent and performing the functional imaging procedure at least four times during a one-month period.

For some applications, administering the radiopharmaceutical agent and performing the functional imaging procedure include administering the radiopharmaceutical agent performing the functional imaging period during a first day, and administering the radiopharmaceutical agent performing the functional imaging period during a second day immediately following the first day.

For some applications, administering the radiopharmaceutical agent and performing the functional imaging procedure include administering the radiopharmaceutical agent performing the functional imaging period during a first hour, and administering the radiopharmaceutical agent performing the functional imaging period during a second hour immediately following the first hour.

For some applications, administering the radiopharmaceutical agent and performing the functional imaging procedure include administering the radiopharmaceutical agent performing the functional imaging period during a plurality of consecutive minutes.

For some applications, the property includes at least one property selected from the group consisting of: a size, a perfusion, a marker of viability or apoptosis, an inflammatory process, metabolism, an expression of a specific protein, an expression of a specific mRNA, and a indication of cancer-specific activity, and performing the functional imaging procedure includes measuring the selected property.

For some applications, the radiopharmaceutical agent includes a tracer associated with mitochondrial activity, and performing the functional imaging procedure includes measuring mitochondrial activity in the at least one tissue.

In an embodiment, performing the imaging procedure includes performing a SPECT imaging procedure on the patient. For some applications, performing the SPECT imaging procedure includes performing the SPECT imaging procedure using a high-definition SPECT camera.

There is yet additionally provided, in accordance with an embodiment of the present inventions a method for treating a human patient, including:

administering, to the patient, a radioactive therapeutic agent at a therapeutically-effective dose;

determining a bioclearance of the therapeutic agent by performing a radioimaging procedure on the patient; and responsively to the bioclearance, setting at least one parameter of a subsequent administration of the therapeutic agent to the patient.

In an embodiment, pharmacological activity of the therapeutic agent is not due to radioactivity of the therapeutic agent. Alternatively, pharmacological activity of the therapeutic agent is due at least in part to radioactivity of the therapeutic agent.

For some applications, the at least one parameter includes a period of time between the administering the agent and the subsequent administration of the agent.

In an embodiment, performing the imaging procedure includes performing a SPECT imaging procedure on the patient. For some applications, performing the SPECT imaging procedure includes performing the SPECT imaging procedure using a high-definition SPECT camera There is also provided, in accordance with an embodiment of the present invention, a method for treating a human patient, including:

administering, to the patients a radioactive therapeutic agent at a therapeutically-effective dose;

repeatedly determining a concentration of the therapeutic agent in at least one tissue of the patient by repeatedly performing a radioimaging procedure on the patient; and upon finding that the concentration has fallen below a threshold level in the at least one tissue, again administering the radioactive therapeutic agent to the patient.

In an embodiment, administering and again administering include maintaining the concentration of the therapeutic agent in the at least one tissue at a generally constant level.

In an embodiment, administering and again administering include maintaining the concentration of the therapeutic agent in the at least one tissue according to a desired time curve of concentration.

In an embodiment, pharmacological activity of the therapeutic agent is due at least in part to radioactivity of the therapeutic agent. Alternatively, pharmacological activity of the therapeutic agent is not due to radioactivity of the therapeutic agent.

In an embodiment, administering includes administering the radioactive therapeutic agent at least four times during a one-month period.

In an embodiment, performing the imaging procedure includes performing a SPECT imaging procedure on the patient. For some applications, performing the SPECT imaging procedure includes performing: the SPECT imaging procedure using a high-definition SPECT camera.

There is further provided, in accordance with an embodiment of the present invention, a method including:
providing a diagnostic radiopharmaceutical agent that includes a therapeutic agent bound to a radiotracer;
administering, to a human patient, a non-therapeutic dose of the radiopharmaceutical agent that has a total radioactivity per body mass of the patient that is less than 0.05 mCi/kg; and
performing an imaging procedure on the patient in conjunction with the administering.

In an embodiment, the method includes administering, to the patient, a drug other than the radiopharmaceutical agent, at a therapeutic dose, and setting at least one parameter of the administering at least in part responsively to a result of the imaging procedure.

In an embodiment, pharmacological activity of the therapeutic agent is not due to radioactivity of the therapeutic agent. Alternatively, pharmacological activity of the therapeutic agent is due at least in part to radioactivity of the therapeutic agent.

There is still further provided, in accordance with an embodiment of the present invention, a method including:
providing a diagnostic radiopharmaceutical agent that includes a therapeutic agent bound to a radiotracer;
administering, to a human patient, a non-therapeutic dose of the radiopharmaceutical agent at least four times during a one-month period; and
performing an imaging procedure on the patient in conjunction with each administration.

In an embodiment, performing the imaging procedure includes detecting organ dysfunction of the patient. Alternatively or additionally, performing the imaging procedure includes detecting an abnormality in a region of interest of the patient.

In an embodiment administering includes administering the non-therapeutic dose of the radiopharmaceutical agent at least ten times during the one-month period. In an embodiment, administering includes administering the non-therapeutic dose of the radiopharmaceutical agent at least once per day during the one-month period.

There is additionally provided, in accordance with an embodiment of the present invention, a method including:
providing a radiopharmaceutical agent that includes a therapeutic agent bound to a radiotracer;
administering, to a human patient, a dose of the radiopharmaceutical agent that has a total radioactivity per body mass of the patient that is less than 0.05 mCi/kg, and includes a therapeutic dosage of the therapeutic agent; and
performing an imaging procedure on the patient in conjunction with the administering.

In an embodiment, the method includes optimizing a therapeutic effect of the therapeutic agent at least in part responsively to a result of the imaging procedure.

In an embodiment, the method includes withholding subsequent administration of the therapeutic agent at least in part responsively to a result of the imaging procedure.

There is yet additionally provided, in accordance with an embodiment of the present invention, a method including:
administering a therapeutic drug at a therapeutic dose;
administering a radiopharmaceutical agent;
performing an imaging procedure in conjunction with the administering of the radiopharmaceutical agent; and
using a result of the imaging procedure to monitor one or more intermediary steps of at least one metabolism selected from the group consisting of: metabolism of the therapeutic drug, and metabolism of a substrate of the therapeutic drug.

There is also provided, in accordance with an embodiment of the present invention, a drug that has been optimized for a human patient or a patient group responsively to imaging of physiological processes using a high-definition SPECT camera.

There is further provided, in accordance with an embodiment of the present invention, a kit including at least:
a first radiolabeled therapeutic agent that has a radiopharmaceutical sensitivity of less than 50% and a radiopharmaceutical specificity of less than 50%; and
a second radiolabeled therapeutic agent that has a radiopharmaceutical sensitivity of less than 50%, and a radiopharmaceutical specificity of less than 50%, wherein the first and second agents are different from one another.

In an embodiment, pharmacological activity of the first radiolabeled therapeutic agent is not due to radioactivity of the first radiolabeled therapeutic agent.

For some applications, the kit includes a third radiolabeled therapeutic agent that has a radiopharmaceutical sensitivity of less than 50%, and a radiopharmaceutical specificity of less than 50%, wherein the first, second, and third agents are different from one another.

The present invention will be more fully understood from the following detailed description of embodiments thereof taken together with the drawings, in which:

BRIEF DESCRIPTION OF THE DRAWINGS

FIG. 3 is a flow chart illustrating a method for treating a patient, in accordance with an embodiment of the present invention; and FIG. 4 is a flow chart illustrating another method for optimizing treatment of a patient, in accordance with an embodiment of the present invention.

DETAILED DESCRIPTION OF EMBODIMENTS

Figure 1:
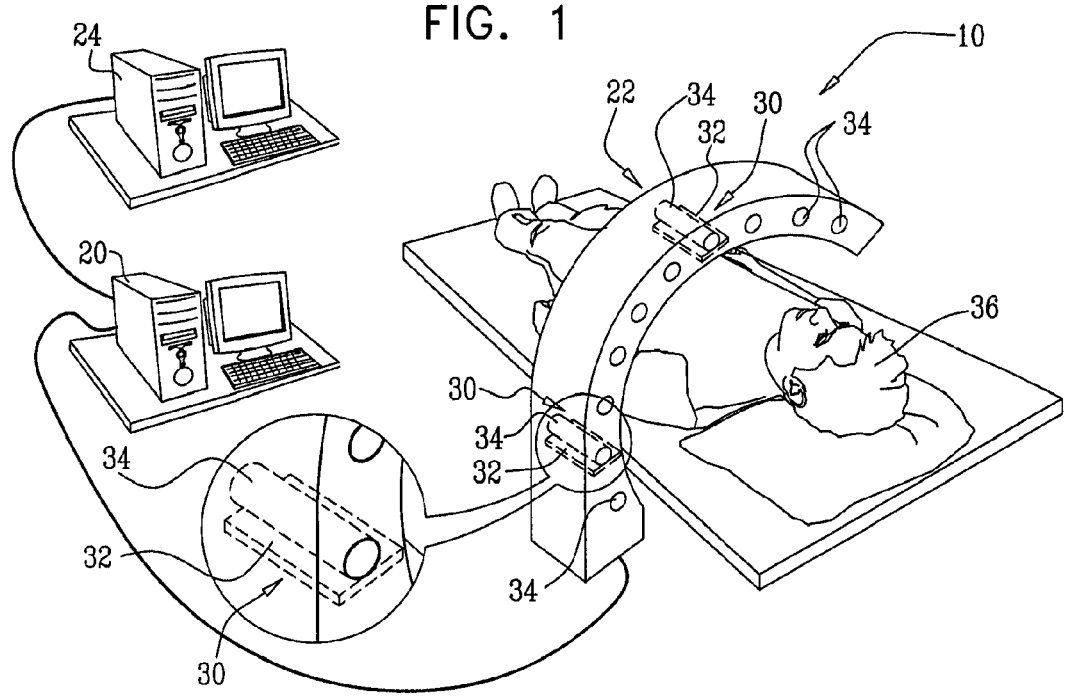
FIG. 1 is a schematic illustration of an imaging system, in accordance with an embodiment of the present invention.

FIG. 1 is a schematic illustration of an imaging system 10, in accordance with an embodiment of the present invention. Imaging system 10 comprises a control unit 20, a camera 22, and imaging workstation 24. Typically, control unit 20 and imaging workstation 24 comprise one or more standard personal computers or servers with appropriate memory, communication interfaces and software for carrying out the functions prescribed by relevant embodiments of the present invention. This software may be downloaded to the control unit and imaging workstation in electronic form over a network, for example, or it may alternatively be supplied on tangible media, such as CD-ROM.

Control unit 20 typically comprises: (a) image acquisition functionality, which is configured to drive camera 22 to perform image acquisition of the patient; (b) image reconstruction functionality, which is configured to perform an image reconstruction procedure on the acquired image; (c) image analysis functionality, which is configured to perform an image analysis procedure on the reconstructed image; and (d) diagnosis functionality, which is configured to perform a diagnostic procedure using the results of the image analysis procedure. It will be appreciated that control unit 20 may comprise a plurality of personal computers or servers, each of which performs one or more of these procedures, and that one or more of these computers or servers may be located remotely from camera 22. Imaging workstation 24 displays the reconstructed images and allows the attending healthcare worker to view and manipulate the images.

For some applications, camera 22 utilizes techniques described in the above-mentioned PCT Publications WO 06/051531 and/or WO 05/119025, and/or in the other co-assigned patent applications and/or patent application publications incorporated herein by reference.

In an embodiment of the present invention, camera 22 comprises a plurality of detector assemblies 30, each of which comprises a detector 32 coupled to an angular orientator 34. Each of the detectors comprises a plurality of gamma ray sensors, such as a pixelated array of crystals, e.g., CZT crystals, and at least one collimator. For example, the array may comprise 16×64 pixels, arranged in sub-arrays of 16×16 pixels. Detector assemblies 30 are arranged at least partially around a region of interest (ROI) of a patient 36.

Figure 2:
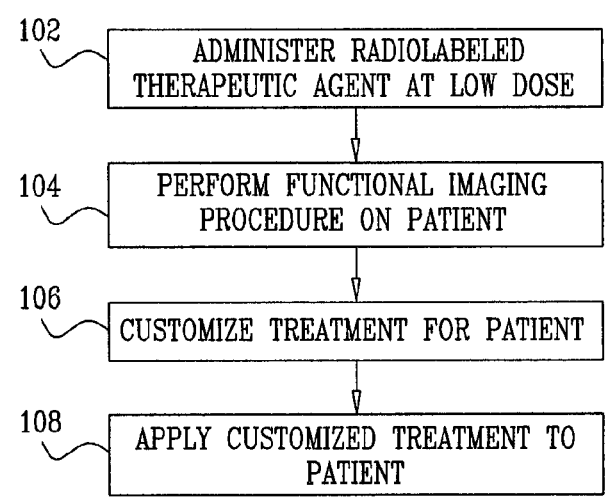
FIG. 2 is a flow chart illustrating a method for optimizing treatment of a patient, in accordance with an embodiment of the present invention.

Reference is made to FIG. 2, which is a flow chart illustrating a method 100 for optimizing treatment of a patient, in accordance with an embodiment of the present invention. At a low dose administration step 102, a radiolabeled therapeutic agent is administered to the patient, typically at a low dose. The low dose is typically lower than a therapeutic dose of the therapeutic agent. Alternatively, the radiopharmaceutical therapeutic agent is administered at a therapeutic dose.

As described in more detail hereinbelow, the radiolabeled therapeutic agent typically comprises a therapeutic agent otherwise known in the art, which is radiolabeled using techniques of embodiments of the present invention. The known, non-radiolabeled form of the therapeutic agent is typically substantially non-radioactive. In other words, the pharmacological activity of the therapeutic agent is typically not due to radioactivity thereof. The phrase "substantially non-radioactive," as used in the present application, including in the claims, means non-radioactive, except for trace levels of radioactivity that are present in some naturally-occurring isotopes. The scope of the present invention includes therapeutic agents known as of the filing date of the present application, as well as therapeutic agents developed or discovered in the future.

At a functional imaging step 104, a functional imaging procedure, e.g., a SPECT or PET imaging procedure, is performed, such as by using the imaging techniques described herein or in the co-assigned applications incorporated herein by reference, to acquire information regarding the activity of the therapeutic agent, such as: the bioactivity of the agent, the uptake of the agent, e.g., areas in the body at which the radiolabeled therapeutic agent concentrates (including desired locations and undesired locations); levels of concentration of the radiolabeled therapeutic agent; actual bioavailability of the radiolabeled therapeutic agent; kinetic information regarding the agent; and/or metabolism of the agent, of a substrate thereof, and/or an enzyme involved in the metabolism of the agent.

At a customize treatment step 106, the information obtained at step 104 is used to customize (i.e., personalize) a subsequent treatment of the patient. The customized subsequent treatment is applied to the patient, at a subsequent treatment step 108.

In an embodiment of the present invention, customizing the subsequent treatment at step 106 comprises determining a subsequent, therapeutic dose of the same therapeutic agent administered at step 102, for therapeutic administration at step 108. For some applications, at step 108 the therapeutic agent is administered in its conventional, non-labeled form. The subsequent, therapeutic dose is typically higher than the low dose administered at step 102. Determining the subsequent dose typically comprises setting the dose at a level that: (a) reduces a likelihood of serious adverse events (SAEs) and/or limits the toxicity of the subsequent administration of the therapeutic agent at the higher, therapeutic dose at step 108; and/or (b) generally maximizes an effectiveness of the subsequent administration of the therapeutic agent. For example, software may calculate the maximum dose of the therapeutic agent that can be delivered without exceeding the maximum accumulation of the therapeutic agent in sensitive organs and/or tissue, and/or the minimum dose of the therapeutic agent necessary to cause sufficient accumulation of the therapeutic agent at one or more desired sites in the body. Alternatively or additionally, customizing the subsequent treatment at step 106 comprises changing a cycle of the treatment, and/or changing a timing of the treatment.

The use of this technique thus enables treatment to be customized (i.e., personalized) per patient, rather than relying on textbook curves of bioavailability applicable to large patient populations. This technique may be particularly beneficial for therapeutic agents for which it is difficult to pre-identity responders and non-responders, or to predict side effects. The information obtained at step 104 may include affinity and/or location information, which is used at step 106 to prevent ineffectiveness, SAEs, and/or toxicity of the agent.

Alternatively, the radiolabeled form of the therapeutic agent administered at low dose step 102 is also administered at subsequent treatment step 108. Such subsequent administration is safe because the level of radiation emitted from the radiolabeled form is so low as to not represent a significant risk to the patient. The pharmacological activity of the therapeutic agent is due to biological and/or chemical properties thereof, and not to the radioactivity thereof.

For some applications, customizing the treatment at step 106 comprises making a decision whether or not to administer the particular therapeutic agent to this particular patient. For example, a decision not to administer the agent may be made because of a high predicted likelihood of SAEs and/or toxicity, and/or a low predicted likelihood of treatment success. For some applications, the information obtained at step 104 is used to determine when the particular patient is likely to be a responder or a non-responder to treatment with the therapeutic agent. Optionally, customizing the treatment includes deciding to perform an additional complementary diagnostic test, and modifying at least one parameter of the treatment at least in part responsively the results of the test.

In an embodiment of the present invention, at low dose administration step 102, a plurality of radiopharmaceutical therapeutic agents are administered at the patient, such as at least five, at least ten, or at least 20 radiopharmaceutical therapeutic agents, each at a low, typically non-therapeutic, dose, as described hereinabove. For some applications, two or more (e.g., all) of the radiopharmaceutical therapeutic agents are labeled with the same tracer. For some applications, the sensitivity of the imaging procedure enables the simultaneous imaging of the two or more agents even thought they are labeled with the same tracer by analyzing the differing kinetics (e.g., uptake time profiles) of the agents. Alternatively, two or more (e.g., all) of the radiopharmaceutical therapeutic agents are labeled with different tracers.

At functional imaging step 104, the functional imaging procedure is performed to acquire information regarding the activity of the therapeutic agents, such as respective bioactivities of the agents, respective uptakes of the agents, respective levels of concentration of the radiolabeled therapeutic agents; respective actual bioavailabilities of the radiolabeled therapeutic agents; respective kinetic information regarding the agents; and/or respective metabolisms of the agents, of respective substrates thereof, and/or respective enzymes involved in the metabolisms of the agents. Customizing the treatment at step 106 comprises selecting one or more of the agents for subsequent administration at respective therapeutic doses at step 108, using the information obtained at step 104, and, typically, deciding not to administer one or more of the other agents at step 108, based on the information obtained at step 104. This method thus allows a physician to determine which of a plurality of potentially beneficial therapeutic agents is likely to be most effective in a particular patient, thereby personalizing the therapeutic agent treatment for the patient.

In an embodiment of the present invention, a kit is provided that comprises a plurality of radiopharmaceutical therapeutic agents, such as at least five, at least 10, or at least 20 radiopharmaceutical therapeutic agents, each at a low, typically non-therapeutic, dose, as described hereinabove. For some applications, all of the radiopharmaceutical therapeutic agents are labeled with the same tracer. Alternatively, at least two of the radiopharmaceutical therapeutic agents are labeled with different tracers.

Alternatively or additionally, at customize treatment step 106, the information obtained at functional imaging step 104 is used to predict leakages or migration to surrounding healthy tissues, and/or risks of serious adverse events (SAEs), and/or to support a decision to administer: other therapeutic agents, such as infusion of an isotonic solution or diuretic if the therapeutic agent has a metabolism through the urinary tract, in order to quickly reduce the predicted SAEs.

For some applications, method 100 is repeated one or more times for the same patient.

For some applications, the techniques of method 100 are combined with the techniques of method 150, described hereinbelow with reference to FIG. 3, and/or with the techniques of method 200, described hereinbelow with reference to FIG. 4.

In an embodiment of the present invention, the therapeutic agent administered at steps 102 and 108 comprises a therapeutic agent that is not ordinarily radioactive, to which a radioactive radiotracer has been bound (e.g., conjugated), in order to label the therapeutic agent. For applications in which the imaging procedure performed at step 104 comprises a SPECT imaging procedure performed using the imaging techniques described herein or in the co-assigned applications incorporated herein by reference, the high sensitivity of the imaging procedure enables the use of radiolabels having even very low specific activity. Conventional SPECT cameras typically are able to detect up to about $10^{-9}$ molar concentration, while SPECT cameras using the imaging techniques described herein or in the co-assigned applications incorporated herein by reference typically are able to detect up to between about $10^{-10}$ and about $10^{-12}$ Molar concentrations.

For some applications, the low dose of the radiolabeled therapeutic agent used at step 102 is less than 10% of a conventional therapeutic dose of the therapeutic agent, or of the therapeutic dose used at step 108, such as less than 5%, less than 2%, less than 1%, less than 0.5%, less than 0.1%, less than 0.05%, or less than 0.01% of the conventional dose or the dose used at step 108. For some applications, the radiolabeled therapeutic agent binds to a biological target in the body of the patient having a molar concentration of less than $10^{-10}$, such as less than $10^{-11}$ or less than $10^{-12}$. For example, the biological target may be a protein (e.g., a cytoplasmic protein or a membrane protein), mRNA, or any other target to which the therapeutic agent binds in vivo.

In an embodiment of the present invention, a kit is provided for radiolabeling a therapeutic agent, typically a therapeutic agent otherwise known in the art. For some applications, the kit comprises a radioisotope of one or more molecules of the therapeutic agent, typically in a fluid. The therapeutic agent is mixed with the radioisotope such that the radioisotope replaces a portion of the non-radioactive isotope of the molecule of the therapeutic agent, over a period of time (e.g., between about one and about two hours). For example, the radioisotope may comprise iodine-131, iodine-123, indium-111, Ga-67 or another beta-emitting isotope, which replaces a portion (e.g., between about 1% and about 5%) of the non-radioactive iodine in the therapeutic agent. Alternatively, the isotope may comprise an isotope appropriate for PET imaging, such as iodine-124. The non-radioactive iodine freed from the therapeutic agent is typically filtered from the therapeutic agent. This labeling process generally does not affect the pharmacological or chemical properties of the therapeutic agent; other than becoming radioactive, the therapeutic agent molecule retains the same structure and biochemical properties. For other applications, chelation is used in order to radiolabel a therapeutic agent otherwise known in the art, for example a therapeutic agent comprising a peptide and/or an anti-body, using a radioisotope or other tracer, such as 99 mTc.

For example, assume that a known therapeutic agent has a recommended dose of x mg for a particular patient. At low dose administration step 102 of method 150, a radiolabeled form of the therapeutic agent is administered at a dose of x/100 or x/1000. Such a low dose substantially avoids any potential toxicity associated with the imaging procedure performed at step 104, both from the bioactivity of the therapeutic agent itself, and from the radiation emitted from the tracer, because only about 1% to 5% of the therapeutic agent molecules are typically radiolabeled. For some applications, the biodistribution analysis performed at imaging step 104 comprises calculating the number of radiolabeled molecules administered at step 102 based on the molecular weight of the therapeutic agent molecule, and determining how many labeled molecules are expected to arrive at each organ and tissue of interest.

For some applications, the therapeutic agent administered at steps 102 and/or 108 comprises a therapeutic agent that targets cancer cells (e.g., at least one of the chemotherapeutic agents listed below in Table 1), a protein, an analgesic, an antibiotic (e.g., one of those listed below in Table 2), a cardiac drug, a neurological drug, an anti-inflammatory agent (e.g., one of those listed below in Table 2), a non-steroidal anti-inflammatory agent (e.g., one of those listed below in Table 2), and any other agent listed below in Table 2.

In an embodiment of the present invention, the therapeutic agent administered at steps 102 and 108 of method 150 comprises a radioactive element configured to treat a condition of the patient, such as cancer. For example, the radiopharmaceutical agent may comprise chromic phosphate P 32, sodium iodide I 131, strontium chloride Sr 89, samarium Sm 153 lexidronam, or sodium phosphate P 32.

In an embodiment of the present invention, a therapeutic agent otherwise known in the art is radiolabeled, such as using the radiolabeling techniques described hereinabove. The radiolabeled therapeutic agent is administered to a patient, typically at a low, non-therapeutic dose, and a radioimaging procedure is performed for diagnostic purposes. The techniques of this embodiment thus provide numerous radiotracers that target specific tissues, organs, and/or biological processes. The high sensitivity of SPECT imaging procedures performed using the techniques described herein or in the co-assigned applications incorporated herein by reference enables the use of radiolabels having even very low specific activity. Conventional SPECT cameras typically are able to detect up to about $10^{-9}$ molar concentration, while SPECT cameras using the imaging techniques described herein or in the co-assigned applications incorporated herein by reference typically are able to detect up to between about $10^{-10}$ and about $10^{-12}$ molar concentrations.

In an embodiment of the present invention, the radiolabeled therapeutic agent binds to a biological target in the body of the patient having a molar concentration of less than $10^{-10}$, such as less than $10^{-11}$ or less than $10^{-12}$. For example, the biological target may be a protein (e.g., a cytoplasmic protein or a membrane protein), mRNA, or any other target to which the therapeutic agent binds in vivo. For example, SPECT tracers for imaging using this technique may have a specific activity on the order 10,000 Ci/mmole and may bind to the biological target in the body at 10% or less, and thus may result in Molar concentration of about $10^{-11}$. Such Molar concentrations are imaged using the techniques hereof to distinguish between target tissue and non-target tissue. Furthermore, imaging using the techniques hereof is possible even at lower binding percentages, such as 1% or less, and/or even with lower specific activities, such as less than 10,000 Ci/mmole or less than 1,000 Ci/mmole. Such lower binding percentages or lower specific activities may avoid toxicity, or occur in the case of limited biological stability of the tracer.

In an embodiment of the present invention, a cocktail of radiolabeled therapeutic agents is provided, which comprises two or more of such agents. For some applications, techniques for analysis are used that are described in International Patent Application PCT/IL2005/001173, filed Nov. 9, 2005, and/or International Patent Application PCT/IL2006/000059, filed Jan. 15, 2006, both of which are assigned to the assignee of the present application and are incorporated herein by reference.

A number of drugs suffer from lack of specificity because they do not sufficiently distinguish target cells from non-target cells when applied to an entire patient population. Customization of the dose of such drugs for a particular patient, using the techniques described herein, enables the drugs to sufficiently distinguish target cells from non-target cells. For example, if a certain drug binds to target cells on average ten times more than it does to non-target cells, but the patient-to-patient variability is 50 times, it may be impossible to determine a single recommended dose that would apply to all patients, and the drug thus may not receive regulatory approval. Using the techniques of method 100 described hereinabove, a precise dose of the drug is determined for the specific patient, which dose is high enough to be therapeutically effective in the specific patient (optionally, even higher than the approved dosage and regimen), but low enough to avoid serious adverse events (SAEs) and side effects for the specific patient. These techniques also earlier cessation of administration of a drug if it is not efficacious in a specific patient. Alternatively or additionally, these techniques are used during drug discovery and/or development processes (for example, in vivo or in human first clinical trials to select which compounds to take to the next development stages), a regulatory approval process, or thereafter to determine recommended doses for segments of a population upon which the drug has differing effects.

In an embodiment of the present invention, a method for performing functional radioimaging comprises administering to a patient a plurality of radiopharmaceutical agents (either as a cocktail, or separately), at least one of which, when administered separately, has low sensitivity and/or low specificity, such that clinically-meaningful diagnostic information cannot be derived using the agent. For some applications, each of the radiopharmaceutical agents, when administered separately, has low sensitivity and/or low specificity.

At least one functional imaging procedure is performed to acquire information regarding the respective activities of the radiopharmaceutical agents, such as: the respective bioactivities of the agents, respective uptakes of the agents, respective levels of concentration of the radiolabeled agents; respective actual bioavailabilities of the radiolabeled agents; respective kinetic information regarding the agents; and/or respective metabolisms of the agents, of respective substrates thereof, and/or respective enzymes involved in the metabolisms of the agents.

The information derived from imaging the plurality of radiopharmaceutical agents is analyzed in combination to enable specific and sensitive detection of a biological target, thereby generating a: clinically-meaningful diagnosis of a condition of the patient.

Typically, each of the radiopharmaceutical agents, if administered alone, has a sensitivity and/or a specificity insufficient to yield high-quality clinical information. For example, if the radiopharmaceutical agent has a low specificity, there is a high likelihood of false identification of a biological target because the agent binds non-specifically to non-target sites. If the radiopharmaceutical agent has a low sensitivity, there is a high likelihood of false negatives, because the agent fails to sufficiently bind to a biological target. However, the combined imaging of a plurality of such low sensitivity and/or low specificity radiopharmaceutical agents allows the generation of imaging information that does not suffer from the lack of specificity and/or sensitivity that each of the agents suffers from alone.

The functional imaging procedure is typically a high-sensitivity imaging procedure, e.g., a SPECT or PET imaging procedure, which is typically performed using the imaging techniques described herein or in the co-assigned applications incorporated herein by reference, to generate a clinically-valuable image of an intra-body region of interest (ROI), as defined hereinbelow. Typically, the plurality of radiopharmaceutical agents are imaged during a single functional imaging procedure; alternatively, the plurality of radiopharmaceutical agents are imaged during one or more functional imaging procedures.

For some applications, one or more of the radiopharmaceutical agents has a sensitivity less than 70%, such as less than 50% or less than 30%, and/or a specificity of less than 70%, such as less than 50% or less than 30%. For some applications, the plurality of radiopharmaceutical agents comprises at least three agents, such as at least four agents, at least five agents, or at least ten agents.

For some applications, each of two or more of the radiopharmaceutical agents has a low specificity, and the three-dimensional images of the distributions of the two or more agents are combined to identify areas in the patient's body that contain a plurality of the two or more agents. Such overlapping areas may be determined, for example, by finding the intersection of the areas containing two or more of the agents (i.e., performing a logical AND operation), by finding the intersection of areas each of which contains a threshold amount of its respective agent, or by using other techniques known in the art for finding intersections of spaces, such as multiplication For some applications, each of two or more of the radiopharmaceutical agents has a low sensitivity, and the three-dimensional images of the distributions of the two or more agents are combined to identify areas in the patients body that contain any of the two or more agents. Such a combination of areas may be determined, for example, by joining the areas containing two or more of the agents (i.e., performing a logical OR operation), by finding the combination of areas each of which contains a threshold amount of its respective agent or by using other techniques known in the art for finding combinations of spaces.

For some applications, at least a first one of the radiopharmaceutical agents has a low sensitivity and a high specificity, and at least a second one of the radiopharmaceutical agents has a low specificity and a high sensitivity. The three-dimensional images of the distributions of the two or more agents are combined to identify areas in the patient's body that contain both of the agents, or, alternatively, at least one of the agents. Which combination technique is used typically depends on the specific levels of sensitivity and specificity of the agents.

For some applications, at least a first one of the radiopharmaceutical agents has a high sensitivity, and at least a second one of the radiopharmaceutical agents has a low sensitivity. Alternatively or additionally, at least a first one of the radiopharmaceutical agents has a high specificity, and at least a second one of the radiopharmaceutical agents has a low specificity.

For some applications, at least one of the radiopharmaceutical agents comprises a therapeutic agent otherwise known in the art, which is radiolabeled using techniques of embodiments of the present invention. The known, non-radiolabeled form of the therapeutic agent is typically substantially non-radioactive. In other words, the pharmacological activity of the therapeutic agent is typically not due to radioactivity thereof. Techniques for performing such radiolabeling are described hereinabove with reference to FIG. 2. Such a drug typically does not have sufficient specificity and/or sensitivity for performing a diagnostic imaging procedure when not used in combination with at least one other radiopharmaceutical agent (which may also be a radiolabeled therapeutic agent), as described above. Typically, the labeled drug is administered at a low, non-therapeutic dose.

For some applications, two or more of the plurality of radiopharmaceutical agents are labeled with different radiotracers. Alternatively or additionally, two or more of the plurality of radiopharmaceutical agents are labeled with the same radiotracer. For some applications, the sensitivity of the imaging procedure enables the simultaneous imaging of the two or more agents even thought they are labeled with the same radiotracer by analyzing the differing kinetics (e.g., uptake time profiles) of the agents.

For some applications, at least one of the radiopharmaceutical agents comprises a known SPECT or PET radiopharmaceutical. Such known SPECT radiopharmaceuticals include, but are not limited to, Tc-99mDTPA, O-15 water, Tc-99 mHWPAO, Tc-99 mSCO, Tc-99mMDP, Tc-99 mM, Xe-133, Tc-99 mMAG3, Ga-67, Tc-99 msestimibi, Tc-99mpertechnetate, thallium-201 chloride, Tc-99mtetrofosmi, F-18FDG, Tc-99mECD, I-123-MIBG, In-111-invitrolabeledleucocytes, In-111-PEG-Anx5, Tc-99m-(Arg-11)CCMSH, I-124/I-125-11-1F4MAb, Tc-99m-WT4185, [I-123]TPCNE, Tc-99m-HYNIC-EGF, [I-123]IL-2, Tc-99m-IL-2, Tc-99m-HYNIC-IL-8, Radioiodine-NP4F(ab')2, [I-123]ITIC, In-111-DTPA-OC, [I-123]Me2Pyr, RP748, In-111-humAb4D5-8, In-111-humAb49D5-8Fab, [I-123]VEGF165, 5-[I-123]IA, R-[I-123]AM2233, [I-123]AM281, Tc-99m-AP39, RadiolabeledAnti-CD105MAb, I-123-Anx5, Tc-99m-IMMU-4, In-111-DTPA-folate, Tc-99m-EC-C225, Tc-99m-EC-folate, In-111-DTPA-Ahx-Lys-40-exendin-4, Tc-99m-HYNIC-annexinV, In-111-2B8MAb, [I-123]IMZ, In-111-CYT-356, Tc-99m-EC-endostatin, I-131-NP-4MAb, [I-123,125]IMPY, [I-124]FIAU, [I-125]TZDM, I-131-B1MAb, [I-123]FP-CIT, Ga-66/67/68-γ-DF-folate, and other SPECT radiopharmaceuticals mentioned in the patent and non-patent references incorporated herein by reference, including in the co-assigned patent applications incorporated herein by reference. Such known PET radiopharmaceutical include, but are not limited to, FDG-PET, C-11-deoxyglucose, O-15 water, C-11 or O-15 carbon monoxide, F-18-FLT, N-13 ammonia, C-11-acetate, C-11-palmitate, [Br-76]deoxyuridine, [I-131,124]deoxyuridine, C-11-methylmethionine, C-11- or F-18-N-methylspiperone, C-11-flumazenil, C-11-carfentanil, and other PET radiopharmaceuticals mentioned in the patent and non-patent references incorporated herein by reference, including in the co-assigned patent applications incorporated herein by reference.

In an embodiment of the present invention, a kit is provided that comprises a plurality of radiopharmaceutical agents each of which, when administered separately, has low sensitivity and/or low specificity, as described above. For some applications, one or more of the radiopharmaceutical agents has a sensitivity less than 70%, such as less than 50% or less than 30%, and/or a specificity of less than 70%, such as less than 50% or less than 30%. For some applications, the plurality of radiopharmaceutical agents comprises at least three agents, such as at least four agents, at least five agents, or at least ten agents.

For some applications, at least one of the radiopharmaceutical agents comprises a therapeutic drug otherwise known in the art which is radiolabeled using techniques of embodiments of the present invention. The known, non-radiolabeled form of the therapeutic agent is typically substantially non-radioactive. In other words, the pharmacological activity of the therapeutic agent is typically not due to radioactivity thereof. Techniques for performing such radiolabeling are described hereinabove with reference to FIG. 2. Such a drug typically does not have sufficient specificity and/or sensitivity for performing a diagnostic imaging procedure when not used in combination with at least one other radiopharmaceutical agent (which may also be a radiolabeled therapeutic agent), as described above. Typically, the labeled drug is administered at a low, non-therapeutic dose.

For some applications, two or more of the plurality of radiopharmaceutical agents are labeled with different radiotracers. Alternatively or additionally, two or more of the plurality of radiopharmaceutical agents are labeled with the same radiotracer. For some applications, the sensitivity of the imaging procedure enables the simultaneous imaging of the two or more agents even thought they are labeled with the same radiotracer by analyzing the differing kinetics (e.g., uptake time profiles) of the agents.

For some applications, at least one of the radiopharmaceutical agents comprises a known SPECT or PET radiopharmaceutical, such as those mentioned above.

For some applications, the multi-agent diagnostic techniques of this embodiment are used in combination with method 100 described hereinabove with reference to FIG. 2, method 150 described hereinbelow with reference to FIG. 3, method 200 described hereinbelow with reference to FIG. 4, or with other diagnostic and/or therapeutic techniques described herein or in the patent or non-patent references incorporated herein by references, including the co-assigned patent applications incorporated herein by reference.

Reference is made to FIG. 3, which is a flow chart illustrating a method 150 for treating a patient, in accordance with an embodiment of the present invention. Method 150 begins at a therapy application step 152, at which a therapy is applied to the patient (either a drug therapy or a non-drug therapy; if a drug therapy, the drug may or may not comprise a radiopharmaceutical). A radiopharmaceutical imaging agent is administered to the patient, at a radiopharmaceutical administration step 154. For some applications in which the therapy includes a drug therapy, the drug is different from the radiopharmaceutical imaging agent, i.e., the drug is not itself radiolabeled for administration at step 154. Alternatively, the drug administered at step 152 is radiolabeled for administration at step 154, such as using techniques described hereinabove with reference to method 100 of FIG. 2. Further alternatively, the radiopharmaceutical imaging agent administered at step 154 comprises another therapeutic agent radiolabeled, such as using the techniques described hereinabove with reference to FIG. 2. Still farther alternatively, the radiopharmaceutical imaging agent comprises a known SPECT or PET radiotracer, such as those mentioned hereinabove with reference to FIG. 2.

At a functional imaging step 156, a functional imaging procedure is performed on the patient to measure a property indicative of biochemical activity of the therapy in at least one tissue of the patient, such as a property indicative of bioavailability of the drug if the therapy comprises a drug therapy.

Responsively to the measured biochemical activity, at least one parameter of the therapy is modified, at a therapy modification step 158. Typically, the method returns to step 152, at which the therapy is again applied with the modified parameter. Alternatively, modifying the therapy comprises ceasing to apply the therapy, responsively to the measured biochemical activity.

At therapy modification step 158, the at least one parameter of the therapy is typically modified to optimize the therapy, such as by modifying a dose or regimen of the therapy, and/or to customize (i.e., personalize) the therapy for the patient, either on a long- or short-term basis. Optionally, modifying the therapy includes deciding to perform an additional complementary diagnostic test, and modifying at least one parameter of the therapy at least in part responsively the results of the test.

For some applications, the techniques of method 150 are used to monitor: (a) a therapeutic effect of a therapy (e.g., an anti-inflammatory agent, an antibiotic agent, or a chemotherapy agent) on target cells, tissue, or an organ, and/or (b) an undesired effect of the therapy on non-target cells, tissue, or organs.

For some applications, functional imaging step 156 (and, optionally, radiopharmaceutical administration step 154) is performed while the therapy is applied to the patient at therapy application step 152. For these applications, application of the therapy may begin: (a) before administration of the radiopharmaceutical, as shown in FIG. 3; (b) after administration of the radiopharmaceutical, but before performing the imaging procedure; or (c) after beginning performance of the imaging procedure. For some applications, radiopharmaceutical administration step 154 and functional imaging step 156 are repeated at least once per day (e.g., for at least two consecutive days, such at least 3, 4, or 5 consecutive days), such as at least once per hour (e.g., for at least two consecutive hours, such at least 3, 4, or 5 consecutive hours), at least once per minute (e.g., for at least two consecutive minutes, such at least 3, 5, 10, 100, or 1000 consecutive minutes), at least once per ten second period (e.g., for at least two consecutive ten-second periods, such at least 3, 5, 10, 100, 1000, or 10,000 consecutive 10-second periods), or substantially continuously during administration of the therapy. For some applications, functional imaging step 156 is performed both before and after applying the therapy at step 152, in order to assess an effect of the therapy.

For some applications, the drug includes a therapeutic agent that targets cancer cells (e.g., at least one of the chemotherapeutic agents listed below in Table 1), a protein, an analgesic, an antibiotic (e.g., one of those listed below in Table 2), a cardiac drug, a neurological drug, an anti-inflammatory agent (e.g., one of those listed below in Table 2), a non-steroidal: anti-inflammatory agent (e.g., one of those listed below in Table 2), and any other agent listed below in Table 2.

The property of the tissue measured at step 156 may include, for example, size, perfusion, a marker of viability or apoptosis, an inflammatory process, metabolism, expression of specific proteins and/or mRNA, or cancer-specific activity. For example, the radiopharmaceutical imaging agent administered at step 154 may comprise a tracer associated with mitochondrial activity, and the measured mitochondrial activity may be used to predict effect of an antibiotic (the effectiveness of which is better predicted by functional imaging than by biodistribution imaging).

Modifying the parameter of the therapy at step 158 may include, for example, increasing or decreasing dose, changing a cycle of the therapy, or changing a timing of the therapy. Alternatively or additionally, modifying the therapy comprises requiring the performance of an additional diagnostic analysis before deciding how to modify the therapy, or not performing the originally intended therapy. For some applications, the method comprises keeping records of the measured properties.

For some applications, at least one parameter of the imaging process is customized (i.e., personalized), such as a parameter of the radiopharmaceutical (e.g., a dose), a parameter of image acquisition (e.g., timing), a parameter of administration of the radiopharmaceutical agent (e.g., timing of administration), or a parameter of image analysis.

For some applications, the radiopharmaceutical imaging agent comprises a radiolabeled therapeutic agent (which, for some applications, comprises a radiolabeled form of the therapeutic drug administered at step 152) that targets the tissue being treated, but is administered at a non-therapeutic dose for imaging purposes. The tissue is typically treated by another drug or non-drug therapy.

For some applications, these techniques for determining the efficacy of a therapy are used instead of or in addition to conventional imaging techniques, such as CT or MRI. The functional information provided by the SPECT imaging procedures provides information not provided by such conventional imaging techniques. For example, when determining the efficacy of treatment of a tumor, such functional information enables a more accurate determination to be made regarding whether the tumor is alive, and/or the precise location of the tumor, than is possible by simply determining the tumor's size or general location.

The functional imaging procedure performed at step 156 is typically a high-sensitivity imaging procedure, e.g., a SPECT or PET imaging procedure, which is typically performed using the imaging techniques described herein or in the co-assigned applications incorporated herein by reference, to generate a clinically-valuable image of an intra-body region of interest (ROI), as defined hereinbelow. Such high sensitivity enables prediction of the efficacy of the therapy in a specific patient, the observation of the effect of the therapy on the target tissue, and the observation of adverse side effects of the therapy on non-target tissue. In addition, such high sensitivity enables the use of a low dose of the radiopharmaceutical agent, which allows the imaging procedure to be safely repeated a plurality of times, if necessary, without exceeding maximum radiation exposure limits. For some applications, the imaging procedure is repeated at least two times during a one-month period, such as at least four times, e.g., at least ten times, or every day or more than once per day during a one-month period, such as for monitoring phenomena that change acutely, such as perfusion, changes in inflammation, or changes in infectious processes. For some applications, the use of such high-sensitivity imaging procedures enables the monitoring of long-term processes ordinarily not detectable using cameras having conventional resolutions.

In an embodiment of the present invention, applying the therapy at step 152 includes administering a cocktail of drugs having differing respective therapeutic benefits and side effects. The techniques of method 150 are used to determine doses and/or relative doses of the plurality of drugs in the cocktail, in order to achieve an optimized, customized balance between the benefits and side-effects of each of the drugs, for a specific patient or group of patients. In contrast, the relative doses of drugs in conventional cocktail therapies are typically pre-defined for all patients, rather than customized for each individual patient or group of patients. For some applications, at least one of the drugs includes a therapeutic agent that targets cancer cells (e.g., at least one of the chemotherapeutic agents listed below in Table 1), a protein, an analgesic, an antibiotic (e.g., one of those listed below in Table 2), a cardiac drug, a neurological drug, an anti-inflammatory agent (e.g., one of those listed below in Table 2), a non-steroidal anti-inflammatory agent (e.g., one of those listed below in Table 2), and any other agent listed below in Table 2.

Reference is made to FIG. 4, which is a flow chart illustrating a method 200 for optimizing treatment of a patient in accordance with an embodiment of the present invention. At an administration stop 202, a radioactive therapeutic agent is administered at a therapeutically-effective dose. At a functional imaging step 204, an imaging procedure, e.g., a SPECT or PET imaging procedure, is performed, such as by using the imaging techniques described herein or in the co-assigned applications incorporated herein by reference, to determine the personalized pharmacodynamics, half life, metabolism features, and/or bioclearance of the radioactive therapeutic agent in general or in a given patient. For some applications, such parameters are determined using the SPECT or PET imaging procedure alone, or using a combination of the SPECT or PET imaging procedure with other means. At a subsequent treatment planning step 206, one or more parameters subsequent treatment sessions are planned based on the determined bioclearance or other drug-related information determined at step 204. Such parameters may include, for example, timing or dosing parameters. The planned subsequent treatment is applied to the patient, at a subsequent treatment step 208. For some applications, after or during the subsequent treatment at step 208, the method returns to step 204, for evaluating the subsequent treatment and planning future treatment. For some applications, at planning step 206, a determination is made to discontinue the treatment.

For some applications, the radioactive therapeutic drug comprises a therapeutic drug otherwise known in the art, which is radiolabeled using techniques of embodiments of the present invention. The known, non-radiolabeled form of the therapeutic agent is typically substantially non-radioactive. In other words, the pharmacological activity of the therapeutic agent is typically not due to radioactivity thereof. Alternatively, the pharmacological activity of the therapeutic agent is due at least in part to radioactivity of the therapeutic agent.

For example, a subsequent administration of the therapeutic radiopharmaceutical may be performed once the concentration of the initially administered dose falls below a threshold level, e.g., in particular sensitive organs and/or tissues, and/or in the target organ and/or tissue. For example, the therapeutic radiopharmaceutical agent may be administered continuously in a closed loop at a rate determined responsively to the bioclearance of the radiopharmaceutical, as determined periodically or substantially continuously by imaging at step 204. For some applications, such continuous administration is configured to maintain a generally constant level of the radiopharmaceutical in the target organ or tissue, or another desired time curve of concentration in the target organ or tissue.

The functional imaging procedure performed at step 204 is typically a high-sensitivity imaging procedure, e.g., a SPECT or PET imaging procedure, which is typically performed using the imaging techniques described herein or in the co-assigned applications incorporated herein by reference, to generate a clinically-valuable image of an intra-body region of interest (ROI), as defined hereinbelow. Such high sensitivity enables prediction of the efficacy of the therapy in a specific patient, the observation of the effect of the therapy on the target tissue, and the observation of adverse side effects of the therapy on non-target tissue. In addition, such high sensitivity enables the use of a low dose of the radiolabeled therapeutic agent, which allows the imaging procedure to be safely repeated a plurality of times, if necessary, without exceeding maximum radiation exposure limits. For some applications, the imaging procedure is repeated at least two times during a one-month period, such as at least four times, e.g., at least ten times, or every day or more than once per day during a one-month period, such as for monitoring phenomena that change acutely, such as perfusion, changes in inflammation, or changes in infectious processes. For some applications, the use of such high-sensitivity imaging procedures enables the monitoring of long-term processes ordinarily not detectable using cameras having conventional resolutions.

For some applications, the radiopharmaceutical administered at steps 202 and/or 208 comprises a radiolabeled drug that is not ordinarily radioactive, as described hereinabove with reference to FIG. 2. Alternatively or additionally, the radiopharmaceutical administered at steps 202 and/or 208 comprises a radioactive element configured to treat a condition of the patient, such as described hereinabove with reference to FIG. 2. For some applications, the drug administered at steps 202 and/or 208 comprises a therapeutic agent that targets cancer cells (e.g., at least one of the chemotherapeutic agents listed below in Table 1), a protein, an analgesic, an antibiotic (e.g., one of those listed below in Table 2), a cardiac drug, a neurological drug, an anti-inflammatory agent (e.g., one of those listed below in Table 2), a non-steroidal anti-inflammatory agent (e.g., one of those listed below in Table 2), and any other agent listed below in Table 2.

In an embodiment of the present invention, a method is provided that comprises providing a diagnostic radiopharmaceutical agent that comprises a therapeutic agent bound to (e.g., conjugated to) a radiotracer. A non-therapeutic dose of the radiopharmaceutical agent is administered to the human patient, which dose has a total radioactivity per body mass of the patient that is less than 0.15 mCi/kg, e.g., less than 0.05 mCi/kg, less than 0.01 mCi/kg, less than 0.005 mCi/kg, or less than 0.001 mCi/kg, or is less than 15 mCi, such as less than 5 mCi, less than 1 mCi, less than 0.5 mCi, or less than 0.1 mCi for a human patient. An imaging procedure is performed on the patient. For some applications, the techniques of this embodiment are performed at step 102 of method 100, described hereinabove with reference to FIG. 2; at step 154 of method 150, described hereinabove with reference to FIG. 3; and/or at step 202 of method 200, described hereinabove with reference to FIG. 4.

Typically, the radiotracer comprises a SPECT radiotracer, and performing the imaging procedure comprises performing a SPECT imaging procedure. Typically, performing the SPECT imaging procedure comprises generating a clinically-valuable image of an intra-body region of interest (ROI), as defined hereinbelow. For some applications, the imaging procedure includes a three-dimensional dynamic imaging study.

Alternatively, for some applications, the radiotracer comprises a PET radiotracer, and performing the imaging procedure comprises performing a PET imaging procedure.

For some applications, the radiotracer is specific to cancer metabolism, or a drug process of the therapeutic agent, of one of its substrates, or of one of the enzymes involved in its metabolism. For example, the radiotracer may comprise an antibody-based tracer, such as Prostate-Specific Membrane Antigen (PSMA).

For some applications, the therapeutic agent comprises a therapeutic agent that has a therapeutic effect when administered at a therapeutic dosage and not bound to a radiotracer. For example, the therapeutic agent may comprise substantially any drug, whether currently known or developed in the future, that can be bound to the radiotracer without changing the molecular structure of the drug sufficiently to render the drug therapeutically ineffective. For some applications, to bound the therapeutic agent to the radiotracer, only a single atom of the therapeutic agent is replaced with the radiotracer (e.g., replacing I-127 with I-123, I-124, or I-131), or replacing more than one occurrence of the same atom with radiotracer atoms. For some applications, the therapeutic agent comprises a radio-therapeutic agent, to which the radiotracer is bound (in other words, the agent is bound to a first radiotracer for therapy, and a second radiotracer for the imaging procedure).

For some applications, the total radioactivity per body mass of the dose of the radiopharmaceutical agent is less than 0.15 mCi/kg, e.g., less than 0.05 mCi/kg, less than 0.01 mCi/kg, less than 0.005 mCi/kg, or less than 0.001 mCi/kg. For some applications, the total radioactivity per body mass of the dose of the radiopharmaceutical agent is greater than 0.0001 mCi/kg, such as greater than 0.0005 mCi/kg, greater than 0.001 mCi/kg, greater than 0.005 mCi/kg, or greater than 0.015 mCi/kg.

For some applications, the radiopharmaceutical agent comprises the therapeutic agent bound to a plurality of SPECT or PET radiotracers, and performing the imaging procedure comprises separately imaging each of the plurality of radiotracers (typically, but not necessarily, simultaneously). Alternatively, for some applications, the radiopharmaceutical agent comprises a plurality of radiopharmaceutical agents, each of which is bound to the same radiotracer or to respective different radiotracers.

For some applications, the method further comprises administering, to the patient, a drug other than the radiopharmaceutical agent, at a therapeutic dose, and setting at least one parameter of the administering at least in part responsively to a result of the imaging procedure. For example, a dosage of the drug may be set at least in part responsively to the result of the imaging procedure. Such administering may occur prior to, simultaneously with, or after administering the radiopharmaceutical agent.

For some applications, administering, the radiopharmaceutical agent comprises administering the radiopharmaceutical agent at least four times, e.g., at least ten times, or every day or more than once per day during a one-month period, such as for monitoring phenomena that change acutely, such as perfusion, changes in inflammation, or changes in infectious processes, and performing the imaging procedure comprises performing the imaging procedure in conjunction with each administration (i.e., during and/or after each administration).

For some applications, the therapeutic agent is selected from the group consisting of: a therapeutic agent that targets cancer cells (e.g., at least one of the chemotherapeutic agents listed below in Table 1), a protein, an analgesic, an antiviral, an antibiotic (e.g., one of those listed below in Table 2), a cardiac drug, a neurological drug, an ant-inflammatory agent (e.g., one of those listed below in Table 2), a non-steroidal anti-inflammatory agent (e.g., one of those listed below in Table 2), vaccines, genetic therapy based therapeutics and any other agent listed below in Table 2.

For some applications, the radiotracer is selected from the group consisting of Tc-99m, I-121, I-123, I-124, Indium-111, Ga-67, and thallium-201.

In an embodiment of the present invention, any of the radiopharmaceutical administration and/or imaging procedures described herein are performed in conjunction with another therapeutic effect, such as stress induced by exercise or pharmacologically, cardiac pacing, changes in blood gasses, such as by inhalation of gasses (e.g., oxygen), body cooling, or body heating. In an embodiment, adenosine injection is administered before administering Tc99m-sestamibi.

In an embodiment of the present invention, a method is provided that comprises providing a diagnostic radiopharmaceutical agent that comprises a therapeutic agent bound to (e.g., conjugated to) a radiotracer. A non-therapeutic dose of the radiopharmaceutical agent is administered to the human patient at least four times during a one-month period, such as at least ten times, e.g., at least once per day. An imaging procedure is performed on the patient in conjunction with each administration (i.e., during and/or after each administration). Alternatively, the agent is administered at least two times per day, such as at least 10 times per day, or at least 21 times per week.

For some applications, this method is performed in conjunction with one or more of the techniques described immediately hereinabove with reference to the previous method.

In an embodiment of the present invention, a method is provided that comprises:
providing a radiopharmaceutical agent that comprises a therapeutic agent bound (e.g., conjugated) to a radiotracer;
administering, to a patient, a dose of the radiopharmaceutical agent that has a total radioactivity per body mass of the patient that is less than 0.15 mCi/kg (such as less than 0.05 mCi/kg, less than 0.01 mCi/kg, less than 0.005 mCi/kg, or less than 0.001 mCi/kg), and includes a therapeutic dosage of the therapeutic agent; and performing an imaging procedure on the patient in conjunction with the administering.

Typically, the radiotracer comprises a SPECT radiotracer, and performing the imaging procedure comprises performing a SPECT imaging procedure. Typically, performing the SPECT imaging procedure comprises generating a clinically-valuable image of an intra-body region of interest (ROI), as defined hereinbelow. For some applications, the imaging procedure includes a three-dimensional dynamic imaging study.

Alternatively, for some applications, the radiotracer comprises a PET radiotracer, and performing the imaging procedure comprises performing a PET imaging procedure.

Typically, a result of the imaging procedure is used to optimize a therapeutic effect of the therapeutic agent. For example, the dosage of the therapeutic agent may be modified at least in part responsively to the result, or a decision may be made to continue or discontinue treatment with the therapeutic agent at least in part responsively to the result. For some applications, the administration and imaging procedure may be repeated a plurality of times, in order to repeatedly optimize the therapeutic effect of the therapeutic agent, such as at least four times, e.g., at least ten times, or every day or more than once per day during a one-month period, such as for monitoring phenomena that change acutely, such as perfusion, changes in inflammation, or changes in infectious processes.

For some applications, the radiopharmaceutical agent comprises a plurality of radiopharmaceutical agents, at least one of which comprises a radiotracer.

In an embodiment of the present invention, an imaging procedure is performed to monitor one or more intermediary steps of metabolism of a therapeutic drug, i.e., steps of a metabolic pathway of the drug. A radiopharmaceutical agent is administered that binds to and/or is uptaken by cells that are targeted by a drug. As a result, the agent serves as a marker for metabolism of the drug, rather than of general cell activity. For some applications, the monitored drug comprises a chemotherapy drug. For some applications, the radiopharmaceutical agent is administered separately from the drug, while for other applications, the therapeutic drug is radiolabeled such that the drug itself serves as the radiopharmaceutical agent, in addition to serving as a therapeutic agent.

In some embodiments of the present invention, the therapeutic agent is selected from the list consisting of: an anti-cancer drug, such as 5-FU, Doxyrubicin, Taxol, Avastin® (Genentech), Gleevec (Novartis) or Gleevec-resistant inhibitors, angiogenesis inhibitors, nucleoside inhibitors, Melphalan; a nucleoside inhibitor; a protease inhibitor; a polymerase inhibitor; an alpha interferon; a beta interferon; a beta blocker; a vasodilator; an anti-hypertension drug; an serotonergic agent, such as an anti-depressive drug; a drug for the treatment of Alzheimer's disease, a drug for the treatment of multiple sclerosis; and a drug for the treatment of Parkinson's disease.

In some embodiments of the present invention, the therapeutic agent is selected from the following chemotherapeutic agents listed in Table 1:

TABLE 1

Abarelix, aldesleukin, Aldesleukin, Alemtuzumab, alitretinoin, allopurinol, altretamine, amifostine, amifostine, amifostine, anastrozole, anastrozole, arsenic trioxide, asparaginase, Asparaginase, azacitidine, BCG Live, bevacizumab, bexarotene TABLE 1-continued capsules, bexarotene gel, bleomycin, bortezomib, busulfan intravenous, busulfan oral, calusterone, capecitabine, carboplatin, carmustine, carmustine, carmustine with Polifeprosan 20 Implant, celecoxib, cetuximab, chlorambucil, cisplatin, cladribine, clofarabine, cyclophosphamide, cytarabine, dacarbazine, dactinomycin, actinomycin D, Darbepoetin alfa, dasatinib, daunorubicin liposomal, daunorubicin, daunomycin, decitabine, denileukin, Denileukin diftitox, dexrazoxane, dexrazoxane, docetaxel, doxorubicin, doxorubicin liposomal, dromostanolone propionate, Elliott's B Solution, epirubicin, epirubicin hcl, Epoetin alfa, erlotinib, estramustine, etoposide phosphate, etoposide, VP-16, exemestane, exemestane, fentanyl citrate, Filgrastim, floxuridine (intraarterial), fludarabine, fluorouracil, 5-FU, fulvestrant, gefitinib, gemcitabine, gemcitabine, gemcitabine hcl, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine, 6-MP, mesna, methotrexate, methoxsalen, mitomycin C, mitotane, mitoxantrone, nandrolone phenpropionate, nelarabine, Nofetumomab, Oprelvekin, oxaliplatin, paclitaxel, palifermin, pamidronate, panitumumab, pegademase, pegaspargase, Pegfilgrastim, pemetrexed disodium, pentostatin, pipobroman, plicamycin, mithramycin, porfimer sodium, procarbazine, quinacrine, Rasburicase, rituximab, sargramostim, Sargramostim, sorafenib, streptozocin, sunitinib maleate, talc (Sclerosol), tamoxifen, temozolomide, teniposide, testolactone, thalidomide, thioguanine, 6-TG, thiotepa, topotecan, topotecan hcl, toremifene, Tositumomab, Tositumomab/I-131 tositumomab, trastuzumab, tretinoin, ATRA, Uracil Mustard, valrubicin, vinblastine, vincristine, vinorelbine, vorinostat, zoledronate, and zoledronic acid.

| Regimen | Chemotherapeutic Agent(s) |
|---|---|
| | Breast Cancer Regimens |
| | Combination Regimens |
| AC | Doxorubicin 40-45 mg/m.sup.2 i.v., day 1 |
| | WITH |
| | Cyclophosphamide 200 mg/m.sup.2 PO, days 3-6 |
| | Repeat cycle every 21 days |
| | OR |
| | Cyclophosphamide 500 mg/m.sup.2 i.v., day 1 |
| | Repeat cycle every 28 days |
| CAF (FAC) | Cyclophosphamide 600 mg/m.sup.2 i.v., day 1 |
| | Doxorubicin 60 mg/m.sup.2 i.v., day 1 |
| | Fluorouracil 600 mg/m.sup.2 i.v., days 1, 8 |
| | Repeat cycle every 28 days |
| | OR |
| | Cyclophosphamide 500 mg/m.sup.2 i.v., day 1 |
| | Doxorubicin 50 mg/m.sup.2 i.v., day 1 |
| | Fluorouracil 500 mg/m.sup.2 i.v., days 1 |
| | Repeat cycle every 21 days and day 8 (FAC) |
| CFM (CNF, FNC) | Cyclophosphamide 600 mg/m.sup.2 i.v., day 1 |
| | Fluorouracil 600 mg/m.sup.2 i.v., day 1 |
| | Mitoxentrone 12 mg/m.sup.2 i.v., day 1 |
| | Repeat cycle every 21 days |
| CMF | Cyclophosphamide 100 mg/m.sup.2 PO, days 1-14 or 600 mg/m.sup.2 i.v., days 1, 8 |
| | Methotrexate 40 mg/m.sup.2 i.v., days 1, 8 |
| | Fluorouracil 600 mg/m.sup.2 i.v., days 1, 8 |
| | Repeat cycle every 28 days |
| | OR |
| | Cyclophosphamide 600 mg/m.sup.2 i.v., day 1 |
| | Methotrexate 40 mg/m.sup.2 i.v., day 1 |
| | Fluorouracil 600 mg/m.sup.2 i.v., day 1 |
| | Repeat cycle every 21 days |
| NFL | Mitoxantrone 12 mg/m.sup.2 i.v., day 1 |
| | Fluorouracill 350 mg/m.sup.2 i.v., days 1-3, after Leucovorin |
| | Leucovorin 300 mg i.v., over 1 hour, days 1-3 |
| | OR |
| | Mitoxantrone 10 mg/m.sup.2 i.v., day 1 |
| | Fluorouracil 1,000 mg/m.sup.2/d CI, days 1-3, after leucovorin |
| | Leucorvorin 100 mg/m.sup.2 i.v., over 15 minutes, days 1-3 |
| | Repeat cycle every 21 days |

TABLE 1-continued

| | |
|---|---|
| Sequential Dox-CFM | Doxorubicin 75 mg/m.sup.2 i.v., every 21 days, for 4 cycles followed by 21- or 280 day CMF for 8 cycles |
| VATH | Vinblastine 4.5 mg/m.sup.2 i.v., day 1<br>Doxorubicin 4.5 mg/m.sup.2 i.v., day 1<br>Thiotepa 12 mg/m.sup.2 i.v., day 1<br>Fluoxymesterone 20 or 30 mg/d PO<br>Repeat cycle every 21 days |
| Vinorelbine Doxorubicin | Vinorelbine 25 mg/m.sup.2 i.v., days 1, 8<br>Doxorubicin 50 mg/m.sup.2 i.v., day 1<br>Repeat cycle every 21 days |

Single-Agent Regimens

| | |
|---|---|
| Anastrozole | Anastrozole 1 mg/d PO |
| Capecitabine | Capecitabine 1,250 mg/m.sup.2 PO bid, days 1-14<br>Repeat cycle every 21 days |
| CFM (CNF, FNC) | Cyclophosphamide 600 mg/m.sup.2 i.v., day 1<br>Fluorouracil 600 mg/m.sup.2 i.v., day 1<br>Mitoxentrone 12 mg/m.sup.2 i.v., day 1<br>Repeat cycle every 21 days |
| Docetaxel | Docetaxel 60-100 mg/m.sup.2 i.v, over 1 hour, every 21 days |
| Gemcitabine | Gemcitabine 725 mg/m.sup.2 i.v, over 30 minutes weekly for 3 weeks, followed by 1 week rest<br>Repeat cycle every 28 days |
| Letrozole | Letrozole 2.5 mg/d PO |
| Megestrol | Megestrol 40 mg PO bid |
| Paclitaxel | Paclitaxel 250 mg/m.sup.2 i.v, over 3 or 24 hours every 21 days<br>OR<br>Paclitaxel 175 mg/m.sup.2 i.v., over 3 hours, every 21 days |
| Tamoxifen | Tamoxifen 10 or 20 mg twice daily or 20 mg/d PO |
| Toremifene citrate | Toremifene citrate 60 mg/d PO |
| Vinorelbine | Vinorelbine 30 mg/m.sup.2 i.v, every 7 days |

Prostrate Cancer Regimens
Combination Regimens

| | |
|---|---|
| Estramustine | Estramustine 200 mg/m.sup.2 PO, tid, days 1-42 |
| Vinblastine | Vinblastine 4 mg/m.sup.2 i.v., weekly for 6 weeks, begin day 1<br>Repeat cycle every 8 weeks |
| FL | Flutamide 250 mg PO, tid<br>WITH<br>Leuprolide acetate 1 mg/d SQ<br>OR<br>Leuprolide acetate depot 7.5 mg IM, every 28 days i.v, day 1 |
| FZ | Flutamide 250 mg PO, tid<br>WITH<br>Goserelin acetate 3.6 mg implant SQ, every 28 days<br>OR<br>Goserelin acetate 10.8 mg implant SQ every 12 weeks<br>Begin regimen 2 months prior to radiotherapy |
| Mitoxantrone Prednisone | Mitoxantrone 12 mg/m.sup.2 i.v., day 1<br>Prednisone 5 mg PO, bid<br>Repeat cycle every 21 days |
| N/A | Bloatutamide 50 mg/d PO<br>WITH<br>Leuprolide acetate depot 7.5 mg IM, every 28 days<br>OR<br>Goserelin acetate 3.6 mg implant SQ, every 28 days |
| PE | Paclitaxel 120 mg/m.sup.2 by 96-hour i.v. infusion, days 1-4<br>Estramustine 600 mg/d PO, qd, 24 hours before paclitaxel<br>Repeat cycle every 21 days |

Single Regimens

| | |
|---|---|
| Estramustine | Estramustine 14 mg/kg/d PO, in 3 or 4 divided doses |
| Goserelin | Goserelin acetate implant 3.6 mg implant SQ 8 weeks before radiotherapy, followed by 28 days by 10.8 mg implant SQ, every 12 weeks |
| Nilutamide | Nilutamide 300 mg PO, days 1-30, then 150 mg PO/d in combination with surgical castration; begin on same day or day after castration |

Multiple Myeloma Regimens
Combination Regimens

| | |
|---|---|
| M2 | Vincristine 0.03 mg/kg i.v., day 1<br>Carmustine 0.5-1 mg/kg i.v., day 1<br>Cyclophosphamide 10 mg/kg i.v., day 1<br>Melphalan 0.25 mg/kg PO, days 1-4<br>OR<br>Melphalan 0.1 mg/kg PO, days 1-7 or 1-10<br>Prednisone 1 mg/kg/d PO, days 1-7<br>Repeat cycle every 35-42 days |
| MP | Melphalan 8-10 mg/m.sup.2 PO, days 1-4<br>Prednisone 60 mg/m.sup.2 PO, days 1-4<br>Repeat cycle every 28-42 days |
| VBMCP | Vincristine 1.2 mg/m.sup.2 i.v., day 1<br>Carmustine 20 mg/m.sup.2 i.v., day 1<br>Melphalan 8 mg/m.sup.2 PO, days 1-4<br>Cyclophosphamide 400 mg/m.sup.2 i.v., day 1<br>Prednisone 40 mg/m.sup.2 PO, days 1-7 all cycles, and 20 mg/m.sup.2 PO, days 8-14 first 3 cycles only<br>Repeat cycle every 35 days |

Single-Agent Regimens

| | |
|---|---|
| Dexamethasone | Dexamethasone 20 mg/m.sup.2 PO, for 4 days beginning on days 1-4, 9-12 and 17-20<br>Repeat cycle every 14 days |
| Interferon alfa-2b | Interferon alfa-2b 2 million units/m.sup.2 SQ 3 times a week for maintenance therapy in selected patients with significant response to initial chemotherapy treatment |
| Melphalan | Melphalan 90-140 mg/m.sup.2 i.v. Administer one cycle |

In some embodiments of the present invention, the therapeutic agent is selected from the following agents listed in Table 2:

TABLE 2

Neurology and other drugs

Invega (paliperidone), Rozerem (ramelteon), Apokyn (apomorphine hydrochloride), Lunesta (eszopiclone), Lyrica (pregabalin), TYSABRI (natalizumab), Cialis (tadalafil), Levitra (vardenafil), Namenda (memantine HCl), Avinza (morphine sulfate), Neurontin (gabapentin), Rebif (interferon beta-1a), Relpax (eletriptan hydrobromide), Strattera (atomoxetine HCl), Xyrem (sodium oxybate), Axert (almotriptan malate), Focalin (dexmethylphenidate HCl), Aspirin, Frova (frovatriptan succinate), Metadate CD, Reminyl (galantamine hydrobromide), Ultracet (acetaminophen and tramadol HCl), Zomig-ZMT (zolmitriptan), Depakote ER (divalproex sodium), Exelon (rivastigmine tartrate), Myobloc, Neurontin (gabapentin), Novantrone (mitoxantrone hydrochloride), Trileptal (oxcarbazepine), Zonegran (zonisamide), Aggrenox, Cenestin, Comtan, Keppra, TABLE 2-continued Lamictal (lamotrigine), Lidoderm Patch (lidocaine patch 5%), Sonata, Topamax, Amerge, Clonazepam, Cylert, Excedrin Migraine, Lamictal, Maxalt, Naltrexone Hydrochloride, Oxycodone and Aspirin, Tasmar, Bromfenac, Carbatrol, Copaxone, Galzin (zinc acetate), Imitrex (sumatriptan), Imitrex Nasal Spray, Migranal, Mirapex, NORCO tablets (Hydrocodone Bitartrate/Acetaminophen 10 mg/325 mg), Oxycodone with Acetaminophen 5 mg/325 mg, Pramipexole, Quadramet (Samarium Sm 153 Lexidronam Injection), Requip (ropinirole hydrochloride), Selegiline tablets, Topamax (topiramate), VERSED (midazolam HCl), ZOMIG, Anexsia, ARICEPT (donepezil hydrochloride), Depakote (Divalproex Sodium), Iontocaine, Kadian, Merrem I.V. (meropenem), Redux (dexfenfluramine hydrochloride), Tegretol (carbamazepine USP), Tegretol-XR (carbamazepine extended-release tablets), UltraJect, Zanaflex (tizanidine hydrochloride), Avonex (Interferon Beta 1-A), and Rilutek (riluzole).

Non-steroidal anti-inflammatory agents (NSAIDs)

detoprofen, diclofenac, diflunisal, etodolac, fenoprofen, flurbiprofen, ibuprofen, indomethacin, ketoprofen, meclofenamate, mefenamic acid, meloxicam, nabumeone, naproxen sodium, oxaprozin, piroxicam, sulindac, tolmetin, celecoxib, rofecoxib, aspirin, choline salicylate, salsalate, sodium salicylate, magnesium salicylate, paracetamol, acetaminophen, and pseudoephedrine Steroids cortisone, dexamethasone, hydrocortisone, methylprednisolone, prednisolone, prednisone, triamcinolone, fluprednisolone, triamcinolone, betamethasone, fluocinolone acetonide, flurandrenolone acetonide, and fluorometholone Antibacterial agents azithromycin, clarithromycin, erythromycin, gatifloxacin, levofloxacin, amoxicillin, and metronidazole Platelet aggregation inhibitors abciximab, aspirin, cilostazol, clopidogrel, dipyridamole, eptifibatide, ticlopidine, and tirofiban Anticoagulants dalteparin, danaparoid, enoxaparin, heparin, tinzaparin, and warfarin Cardiovascular drugs Inotropic agents, beta blockers (e.g., metoprolol, carvedilol), calcium antagonists, organic nitrates, anti-arrhythmics, ACE inhibitors, ATII (=AT1) antagonists, diuretics (e.g. furosemide plus amiloride), cholesterol lowering drugs, clot-busters, anti-coagulants, anti-platelet drugs, diuretics, vasodilators, inotropic agents, loop diuretics (frusemide), potassium-sparing diuretics (amiloride), aldosterone antagonists (spironolactone), beta-blockers, ACE inhibitors, angiotensin receptor antagonists, nitroglycerine, polyol nitrates, calcium channel antagonists, b adrenergic blocking agents, abciximab, calcium channel blocker (e.g. nifedipine, verapamil, other dihydropyridines), lipid lowering and anti-clotting drugs, aspirin, clopidogrel, digitalis, heparin, a clot-dissolving enzyme (e.g., tissue plasminogen activator, streptokinase, urokinase), cholesterol reduction drugs (e.g., HMG-CoA reductase inhibitors (lovastatin)), antiarrhythmic drugs, catecholamines (e.g., dopamine), dobutamine, proteases (e.g., lovastatin), warfarin, abciximab, amiloride, frumilm, amiodarone, COX inhibitors, atropine, captopril, clopidogrel, digitalis, ouabain, dipyridamole, furosemide (=frusemide), isoprenaline (and other adrenaline analogues), losartan, lovastatin, morphine, an organic nitrate, propranolol, quinidine, novocaine, class I anti-arrhythmics, spironolactone, urokinase, streptokinase, vitamin K antagonist, captopril, Vasoactive peptides, angiotensin, atrial natriuretic, B-natriuretic, C-natriuretic, bradykinin, endothelin, vasopressin, VIP, adenosine, adrenaline, aldosterone, histamine, leukotriene LTC4, noradrenaline, nitric oxide, prostacyclin PGI2, prostaglandin PGE1/E2, thromboxane TXA2, selective aldosterone receptor antagonists, calcium sensitizers, cytokine inhibitors, endothelin receptor antagonists, growth hormone releasers, natriuretic peptides, neutral endopeptidase inhibitors, vasopeptidase inhibitors and vasopressin antagonists, levosimendan, bosentan, ghrelin, nesiritide, thiorphan, eplerenone, omapatrilat, vasopressin antagonist, Adrenomedullin, Spironolactone, Eplerenone, Brain natriuretic peptide (BNP, nesiritide), Calcium sensitisers, and Levosimendan.

Lipid-lowering agents cholestyramine, colestipol, nicotinic acid, gemfibrozil, probucol, ezetimibe, and statins such as atorvastatin, rosuvastatin, lovastatin simvastatin, pravastatin, cerivastatin, and fluvastatin Anesthetics benzocaine, butamben picrate, tetracaine, dibucaine, prilocaine, etidocaine, mepivacaine, bupivicaine, and lidocaine Zinc salts zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate TABLE 2-continued

| Other acids |
| --- |
| Organic acids, such as acetic, lactic, pamoic, maleic, citric, malic, ascorbic, succinic, benzoic, palmitic, suberic, salicylic, tartaric, methanesulfonic, toluenesulfonic, and trifluoroacetic acid; polymeric acids, such as tannic acid, carboxymethyl, and cellulose; and inorganic acids, such as hydrochloric acid, hydrobromic acid, sulfuric acid, and phosphoric acid |
| Metal complexes |
| zinc and iron |
| Antimicrobial agents |
| amoxillin, erythromycin, azithromycin, clarithromycin, gentamicin, tobramycin, Quinolones, ciprofloxaxin, norfloxacin, gatifloxacin, ofloxacin, levofloxacin, moxifloxacin, metronidazole, lomefloxacin, ciprofloxacin, natamycin, neomycin, polymyxin B, gentamycin, trovafloxacin, grepafloxacin, sulfacetamide, tetracycline, gramicidin, chloremphenicol, bacitracin, and gramicidin |
| Antibiotics |
| aminoglycosides, such as amikacin, apramycin, arbekacin, bambermycins, butirosin, dibekacin, dihydrostreptomycin, fortimicin(s), fradiomycin, gentamicin, ispamicin, kanamycin, micronomicin, neomycin, neomycin undecylenate, netilmicin, paromomycin, ribostamycin, sisomicin, spectinomycin, streptomycin, streptonicozid, and tobramycin; amphenicols, such as azidamfenicol, chloramphenicol, chloramphenicol palmirate, chloramphenicol pantothenate, florfenicol, and thiamphenicol; ansamycins, such as rifampin, rifabutin, rifapentine, and rifaximin; β-Lactams, such as amidinocillin, amdinocillin, pivoxil, amoxicillin, ampicillin, aspoxicillin, azidocillin, azlocillin, bacampicillin, benzylpenicillinic acid, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzhydrylamine, penicillin G calcium, penicillin G hydragamine, penicillin G potassium, penicillin G, procaine, penicillin N, penicillin O, penicillin V, penicillin V benzathine, penicillin V hydrabamine, penimepicycline, phenethicillin, piperacillin, pivapicillin, propicillin, quinacillin, sulbenicillin, talampicillin, temocillin and ticarcillin; carbapenems, such as imipenem; cephalosporins, such as 1-carba (dethia) cephalosporin, cefactor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpirimide, cefpodoxime proxetil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin, cephalothin, cefaclor, cefotetan, cefprozil, loracarbef, cefetamet, and cefepime; cephamycins such as cefbuperazone, cefmetazole, cefminox, cefetan, and cefoxitin; monobactams such as aztreonam, carumonam, and tigemonan; oxacephems such as flomoxef and moxolactam; lincosamides such as clindamycin and lincomycin; macrolides such as azithromycin, carbomycin, clarithromycin, erythromycin(s) and derivatives, josamycin, leucomycins, midecamycins, miokamycin, Oleandomycin, primycin, rokitamycin, rosaramicin, roxithromycin, spiramycin and troleandomycin; polypeptides such as amphomycin, bacitracin, capreomycin, colistin, enduracidin, enylomycin, fusafungine, gramicidin(s), gramicidin S, mikamycin, polymyxin, polymyxin. β-methanesulfonic acid, pristinamycin, ristocetin, teicoplanin, thiostrepton, tuberactinomycin, tyrocidine, tyrothricin, vancomycin, viomycin(s), virginiamycin and zinc bacitracin; tetracyclines such as spicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin and tetracycline; and 2,4-diaminopyrimidines such as brodimoprim, tetroxoprim and trimethoprim; nitrofurans such as furaltadone, furazolium, nifuradene, nifuratel, nifurfoline, nifurpirinol, nifurprazine, nifurtoinol and nitrofurantoin; quinolones such as amifloxacin, cinoxacin, ciprofloxacin, difloxacin, enoxacin, fleroxacin, flumequine, lomefloxacin, miloxacin, nalidixic acid, norfloxacin, ofloxacin, oxolinic acid, perfloxacin, pipemidic acid, piromidic acid, rosoxacin, temafloxacin, and tosufloxacin; sulfonamides such as acetyl sulfamethoxypyrazine, acetyl sulfisoxazole, azosulfamide, benzylsulfamide, chloramine-β, chloramine-T, dichloramine-T, formosulfathiazole, $N_2$-formyl-sulfisomidine, $N_4$-β-D-glucosylsulfanilamide, mafenide, 4'-(methyl-sulfamoyl)sulfanilanilide, p-nitrosulfathiazole, noprylsulfamide, phthalysulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicyclic acid, $N_4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine and sulfisoxazole; sulfones, such as acedapsone, acediasulfone, acetosulfone, dapsone, diathymosulfone, glucosulfone, solasulfone, succisulfone, sulfanilic acid, p-sulfanilylbenzylamine, p,p'-sulfonyldianiline-N,N'digalactoside, sulfoxone and thiazolsulfone; lipopeptides such as daptomycin; oxazolidones such as linezolid; |

TABLE 2-continued ketolides such as telithromycin; and miscellaneous antibiotics such as clofoctol, hexedine, magainins, methenamine, methenamine anhydromethylene-citrate, methenamine hippurate, methenamine mandelate, methenamine sulfosalicylate, nitroxoline, squalamine, xibornol, cycloserine, mupirocin, and tuberin. Class of Zyvox/linezolid (Pfizer)

Formulations for oral use include tablets containing the active ingredients) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

In an embodiment of the present invention, any of the therapeutic agents administered in any embodiment of the present invention described herein is administered orally.

Analgesics

Metamizol, Actaminophen, Ibuprofen, Indomethacin, Fenoprofen, Meclofenamate, Naproxen, Naproxen sodium, Piroxicam, Sulindac, Salsalate, Chol sal/magnesium salicylate, Diflunisal, Etodolac, Flubiprofen, Ketorolac, Tolmetin, Diclofenac sodium, Indomethacin SR Ketoprofen, Celecoxib, Rofecoxib, Baclofen, Chlorzoxazone, Cyclobenzaprine, Methocarbamol, Methocarbamol/aspirin, Orphenadrine, Orphenadrine/aspirin/caffeine, Dantrolene, Propoxyphene hcl, Proproxyphene hcl/acetaminophen, Propoxyphene napsylate/apap, Pentazocine/naloxone, Codeine phosphate/apap, Codeine phosphate/aspirin, Hydrocodone bitartrate/apap, Hydrocodone bitartrate/apap, Hydrocodone bitartrate/aspirin, Meperidine, Meperidine/promethazine, Oxycodone/acetaminophen, Hydromorphone, Oxycodone, Codeine phosphate, Morphine, Fentanyl, Morphine, and Oxycodone.

Other Drugs

Bevacizumab (Avastin®; Genentech), Cetuximab (Erbitux®; ImClone), Erlotinib (Tarceva®; Genentech), Gefitinib (Iressa®; AstraZeneca), Sunitinib (Sutent®; Pfizer), Sorafenib (Nexavar®; Bayer), Bortezomib (Velcade®, Millennium), Bexarotene (Targretin®; Ligand), Panitumumab (Amgen), Vatalanib Novartis/Schering AG), AMG706 (Amgen), AZD2171 (AstraZeneca), ZD6474 (Zactima; AstraZeneca), TGFβAS Vaccine (Lucanix; NovaRx), Paclitaxel+ (/) carboplatin±bevacizumab, Paclitaxel, Carboplatin, cisplatin/vinorelbine±cetuximab (vinorelbine is mentioned but not in this combination), cisplatin, Paclitaxel/Carboplatin+Cetuximab, Paclitaxel/Carboplatin, Bortezomib+Gemcitabine/Carboplatin, ABI-007, AMG706/panitumumab, Erlotinib+Bevacizumab, and Chemotherapy±Bevacizumab.

In respective embodiments of the present invention, all of the imaging protocols described herein and/or in the co-assigned patent applications incorporated herein by reference are enabled to generate clinically-valuable images. A "clinically-valuable image" is an image of an intra-body ROI containing the labeled radiopharmaceutical agent(s)$_5$ which image fulfills one or more of the following criteria:

the image is generated according to a protocol, including at the radiopharmaceutical dose specified by the protocol, using a high-definition SPECT camera, for example, camera 22 of imaging system 10, described hereinabove with reference to FIG. 1, which camera, during the imaging of the ROI, is capable of acquiring at least one of 5000 photons emitted from the ROI during the image acquisition procedure, such as at least one of 4000, 3000, 2500, 2000, 1500, 1200, 1000, 800, 600, 400, 200, 100, or 50 photons emitted from the ROI. In one particular embodiment, the camera is capable of acquiring at least one of 2000 photons emitted from the ROI during the image acquisition procedure;

the image is generated according to a protocol, including at the radiopharmaceutical dose and image acquisition duration specified by the protocol, using a high-definition SPECT camera, for example, camera 22, which, during the imaging of the ROI, is capable of acquiring at least 200,000 photons, such as at least 500,000, 1,000,000, 2,000,000, 3,000,000, 4,000,000, 5,000,000, 8,000,000, or 10,000,000 photons, emitted from a portion of the ROI having a volume of no more than 500 cc, such as a volume of no more than 500 cc, 400 cc, 300 cc, 200 cc, 150 cc, 100 cc, or 50 cc. In one particular embodiment the camera is capable of acquiring at least 1,000,000 photons emitted from a volume of the ROI having a volume of no more than 200 cc;

the image has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the labeled radiopharmaceutical agent as distributed within the ROI has a range of emission-intensities R (which is measured as emitted photons/unit time/volume), and wherein at least 50% of the voxels of the reconstructed three-dimensional emission-intensity image of the ROI have inaccuracies of less than 30% of range R, such as less than 25%, 20%, 15%, 10%, 5%, 2%, 1%, or 0.5% of range R. For example, the agent may emit over a range from 0 photons/second/cc to 10$^5$ photons/second/cc, such that the range R is 10$^5$ photons/second/cc, and at least 50% of the voxels of the reconstructed three-dimensional intensity image of the ROI have inaccuracies of less than 15% of range R, i.e., less than 1.5×10$^4$ photons/second/cc. For some applications, the study produce a parametric image related to a physiological process occurring in each voxel. In one particular embodiment, the image has a resolution of at least 5×5×5 mm, and at least 50% of the voxels have inaccuracies of less than 15% of range R;

the image is generated according to a protocol, including at the radiopharmaceutical dose and image acquisition duration specified by the protocol, and the image has a resolution of at least 7×7×7 mm, such as at least 6×6×6 mm, 5×5×5 mm, 4×4×4 mm, 4×3×3 mm, or 3×3×3 mm, in at least 500% of the reconstructed volume, wherein the labeled radiopharmaceutical agent as distributed within the ROI has a range of emission-intensities R (which is measured as emitted photons/unit time/volume), and wherein at least 50% of the voxels of the reconstructed three-dimensional emission-intensity image of the ROI have inaccuracies of less than 30% of range R, such as less than 25%, 20%, 15%, 10%, 5%, 2%, 1%, or 0.5% of range R. For example, the agent may emit over a range from 0 photons/second/cc to 10$^5$ photons/second/cc, such that the range R is 10^5 photons/second/cc, and at least 50% of the voxels of the reconstructed three-dimensional intensity image of the ROI have inaccuracies of less than 15% of range R, i.e., less than 1.5×10^4 photons/second/cc. For some applications, the study produces a parametric image related to a physiological process occurring in each voxel. In one particular embodiment, the image has a resolution of at least 5×5×5 mm, and at least 50% of the voxels have inaccuracies of less than 15% of range R;

the image has a resolution of at least 20×20×20 mm, such as at least 15×15×15 mm, 10×10×10 mm, 7×7×7 mm, 5×5×5 mm, 4×4×4 mm, 4×3×3 mm, or 3×3×3 mm, wherein values of parameters of a physiological process modeled by a parametric representation have a range of physiological parameter values R, and wherein at least 50% of the voxels of the reconstructed parametric three-dimensional image have inaccuracies less than 100% of range R, such as less than 70%, 50%, 40%, 30%, 25%, 20%, 15%, 10%, 5%, 2%, 1%, or 0.5% of range R. For example, the physiological process may include blood flow, the values of the parameters of the physiological process may have a range from 0 to 100 cc/minute, such that the range R is 100 cc/minute, and at least 50% of the voxels of the reconstructed parametric three-dimensional image have inaccuracies less than 25% of range R, i.e., less than 25 cc/minute. In one particular embodiment, the image has a resolution of at least 5×5×5 mm, and at least 50% of the voxels have inaccuracies of less than 25% of range R; and/or the image is generated according to a protocol, including at the radiopharmaceutical dose and image acquisition duration specified by the protocol, and the image has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein if the labeled radiopharmaceutical agent is distributed substantially uniformly within a portion of the ROI with an emission-intensity I+/−10% (which is defined as emitted photons/unit time/volume), and wherein at least 85% of the voxels of the reconstructed three-dimensional emission-intensity image of the portion of the ROI have inaccuracies of less than 30% of intensity I, such as less than 15%, 10%, 5%, 2%, 10%, 0.5%, 20%, or 25% of intensity I. For example, the agent may be distributed within a volume with a uniform emission-intensity I of 10^5 photons/second/cc, and at least 85% of the voxels of the reconstructed three-dimensional intensity image of the volume have inaccuracies of less than IS % of intensity I, i.e., less than 1.5×10^4 photons/second/cc. For some applications, the same definition may apply to a study which produces a parametric image related to a physiological process occurring in each voxel. In one particular embodiment, the image has a resolution of at least 5×5×5 mm, and at least 50% of the voxels have inaccuracies of less than 15% of intensity I.

The scope of the present invention includes embodiments described in the following applications, which are assigned to the assignee of the present application and are incorporated herein by references. In an embodiment, techniques and apparatus described in one or more of the following applications are combined with techniques and apparatus described herein:

an international patent application filed May 11, 2006, entitled, "Unified management of radiopharmaceutical dispensing, administration, and imaging";

International Patent Application PCT/IL2005/001173, filed Nov. 9, 2005, which published as PCT Publication WO 06/051531;

International Patent: Application PCT/IL2005/000572, filed Jun. 1, 2005, and U.S. patent application Ser. No. 11/628,074 in the national stage thereof;

International Patent Application PCT/IL2005/000575, filed Jun. 1, 2005;

International Patent Application PCT/IL2005/001215, filed Nov. 16, 2005, which published as PCT Publication WO 06/054296;

U.S. Provisional Patent Application 60/625,971, filed Nov. 9, 2004;

U.S. Provisional Patent Application 60/628,105, filed Nov. 17, 2004;

U.S. Provisional Patent Application 60/630,561, filed Nov. 26, 2004;

U.S. Provisional Patent Application 60/632,236, filed Dec. 2, 2004;

U.S. Provisional Patent Application 60/632,515, filed Dec. 3, 2004;

U.S. Provisional Patent Application 60/635,630, filed Dec. 14, 2004;

U.S. Provisional Patent Application 60/636,088, filed Dec. 16, 2004;

U.S. Provisional Patent Application 60/640,215, filed Jan. 3, 2005;

U.S. Provisional Patent Application 60/648,385, filed Feb. 1, 2005;

U.S. Provisional Patent Application 60/648,690, filed Feb. 2, 2005;

U.S. Provisional Patent Application 60/675,892, filed Apr. 29, 2005;

U.S. Provisional Patent Application 60/691,780, filed Jun. 20, 2005;

U.S. Provisional Patent Application 60/700,318, filed Jul. 19, 2005;

U.S. Provisional Patent Application 60/700,299, filed Jul. 19, 2005;

U.S. Provisional Patent Application 60/700,317, filed Jul. 19, 2005;

U.S. Provisional Patent Application 60/700,753, filed Jul. 20, 2005;

U.S. Provisional Patent Application 60/700,752, filed Jul. 20, 2005;

U.S. Provisional Patent Application 60/702,979, filed Jul. 28, 2005;

U.S. Provisional Patent Application 60/720,034, filed Sep. 26, 2005;

U.S. Provisional Patent Application 60/720,652, filed Sep. 27, 2005;

U.S. Provisional Patent Application 60/720,541, filed Sep. 27, 2005;

U.S. Provisional Patent Application 60/750,287, filed Dec. 13, 2005;

U.S. Provisional Patent Application 60/750,334, filed Dec. 15, 2005;

U.S. Provisional Patent Application 60/750,597, filed Dec. 15, 2005;

U.S. Provisional Patent Application 60/799,688, filed May 11, 2006;

U.S. Provisional Patent Application 60/800,845, filed May 17, 2006, entitled, "Radioimaging camera for dynamic studies";

U.S. Provisional Patent Application 60/800,846, filed May 17, 2006, entitled, "Radioimaging protocols";

U.S. Provisional Patent Application 60/763,458, filed Jan. 31, 2006;

U.S. Provisional Patent Application 60/741,440, filed Dec. 2, 2005;

U.S. Provisional patent application Ser. No. 11/034,007, filed Jan. 13, 2005, which issued as U.S. Pat. No. 7,176,466;

U.S. Provisional patent application Ser. No. 09/641,973, filed Aug. 21, 2000;

U.S. Provisional Patent Application 60/750,294, filed Dec. 13, 2005 (this application has not been assigned to the assignee of the present application; an assignment is in the process of being executed and filed);

U.S. Provisional Patent Application 60/816,970, filed Jun. 28, 2006;

International Patent Application PCT/IL2006/000059, filed Jan. 15, 2006;

International Patent Application PCT/IL2005/000048, filed Jan. 13, 2005;

International Patent Application PCT/IL03/00917, filed Nov. 4, 2003;

Israel Patent Application 172349, filed Nov. 27, 2005; and

Israel Patent Application 171346, filed Oct. 10, 2005.

International Patent Application PCT/IL2006/000562, filed May 11, 2006;

U.S. Provisional Patent Application 60/799,688, filed May 11, 2006;

U.S. Provisional Patent Application 60/816,970, filed Jun. 28, 2006;

International Patent Application PCT/IL2006/001511, filed Dec. 28, 2006;

International Patent Application PCT/IL2006/001291, filed Nov. 29, 2006;

International Patent Application PCT/IL2006/000834, filed Jul. 19, 2006;

International Patent Application PCT/IL2006/000840, filed Jul. 19, 2006;

U.S. Provisional Patent Application 60/754,199, filed Dec. 28, 2005;

U.S. patent application Ser. No. 11/607,075, filed Dec. 1, 2006;

U.S. patent application Ser. No. 11/656,548 filed Jan. 13, 2005; and

U.S. patent application Ser. No. 10/533,568, filed Nov. 4, 2003.

Embodiments of the present invention are typically used for treating and/or diagnosing human patients. The terms "therapeutic agent" and "drug" are used interchangeably in the present application, including in the claims.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
    administering respective radiolabeled forms of a plurality of therapeutic agents to a patient, wherein two or more of the radiolabeled forms of the plurality of therapeutic agents are radiolabeled with a same radiotracer;
    determining information related to respective biodistributions of the respective radiolabeled forms of the plurality of therapeutic agents in the patient by performing simultaneous functional imaging of the respective radiolabeled forms of the plurality of therapeutic agents during a radioimaging procedure on the patient after administering the respective radiolabeled forms of the plurality of therapeutic agents, wherein performing simultaneous functional imaging of the respective radiolabeled forms of the plurality of therapeutic agents comprises analyzing differing kinetics of the respective radiolabeled forms of the plurality of therapeutic agents; and
    treating the patient by administering the one or more of the plurality of therapeutic agents to the patient at respective therapeutically-effective doses and withholding administering at least one other of the plurality of therapeutic agents.

2. The method according to claim 1, wherein treating the patient by administering the one or more of the plurality of therapeutic agents to the patient at the respective therapeutically-effective doses comprises treating the patient by administering non-radiolabeled forms of the one or more of the plurality of therapeutic agents to the patient at the respective therapeutically-effective doses, which non-radiolabeled forms of the therapeutic agent are substantially non-radioactive.

3. The method according to claim 1, wherein treating the patient by administering the one or more of the plurality of therapeutic agents to the patient at the respective therapeutically-effective doses comprises treating the patient by administering the radiolabeled forms of the one or more of the plurality of therapeutic agents to the patient at the respective therapeutically-effective doses.

4. The method according to claim 1, wherein administering the respective radiolabeled forms of the plurality of therapeutic agents comprises administering the respective radiolabeled forms of the therapeutic agents at respective first doses each of which has a total radioactivity per body mass of the patient that is less than 0.05 mCi/kg.

5. The method according to claim 1, wherein administering the respective radiolabeled forms of the plurality of therapeutic agents comprises administering the respective radiolabeled forms of the plurality of therapeutic agents at respective first doses that are less than the respective therapeutically-effective doses.

6. The method according to claim 5, wherein the respective first doses are less than 10% of the respective therapeutically-effective doses.

7. The method according to claim 6, wherein the respective first doses are less than 1% of the respective therapeutically-effective doses.

8. The method according to claim 7, wherein the respective first doses are less than 0.1% of the respective therapeutically-effective doses.

9. The method according to claim 1, wherein administering the respective radiolabeled forms of the plurality of therapeutic agents comprises administering each of the radiolabeled forms formed by replacing a non-radioactive isotope of an element of a non-radiolabeled form of the therapeutic agent with a radioactive isotope.

10. The method according to claim 1, wherein administering the respective radiolabeled forms of the plurality of therapeutic agents comprises administering each of the radiolabeled forms formed by bonding a radioactive radiotracer to the non-radiolabeled form of the therapeutic agent.

11. The method according to claim 1, wherein each of the therapeutic agents is selected from the group consisting of: a protein, an analgesic, an antibiotic, a cardiac drug, a neurological drug, an anti-inflammatory agent, and a non-steroidal anti-inflammatory agent.

12. The method according to claim 1, wherein performing the radioimaging procedure comprises performing a SPECT imaging procedure on the patient.

13. The method according to claim 1, wherein analyzing differing kinetics of the respective radiolabeled forms of the plurality of therapeutic agents comprises determining a time profile of the respective biodistributions of the respective radiolabeled forms of the plurality of therapeutic agents.

14. The method according to claim 13, wherein time profile is an uptake time profile.

15. The method according to claim 1, wherein the plurality of therapeutic agents comprise at least five therapeutic agents.

16. The method according to claim 1, wherein administering the respective radiolabeled forms of the plurality of therapeutic agents comprises administering the respective radiolabeled forms of the plurality of therapeutic agents at therapeutic doses.

17. The method according to claim 1, wherein administering the respective radiolabeled forms of the plurality of therapeutic agents comprises administering the respective radiolabeled forms of the plurality of therapeutic agents at respective substantially non-therapeutically-effective doses.

18. The method according to claim 1, wherein administering the respective radiolabeled forms of the plurality of therapeutic agents comprises administering the respective radiolabeled forms of the plurality of therapeutic agents wherein pharmacological activity of the therapeutic agents is not due to radioactivity of the therapeutic agents.

19. The method according to claim 4, wherein administering the respective radiolabeled forms of the therapeutic agents comprises administering the respective radiolabeled forms of the therapeutic agents at respective first doses each of which has a total radioactivity per body mass of the patient that is less than 0.01 mCi/kg.

20. The method according to claim 11, wherein one of the therapeutic agents comprises bevacizumab.

21. The method according to claim 11, wherein one of the therapeutic agents comprises cetuximab.

* * * * *